US011541125B2

(12) United States Patent
Maynard et al.

(10) Patent No.: US 11,541,125 B2
(45) Date of Patent: Jan. 3, 2023

(54) NONCRUSHABLE PILL FORMULATIONS

(71) Applicant: THE REGENTS OF THE UNIVERSITY OF CALIFORNIA, Oakland, CA (US)

(72) Inventors: Heather D. Maynard, Los Angeles, CA (US); Natalie Boehnke, Los Angeles, CA (US); Samantha J. Paluck, Los Angeles, CA (US)

(73) Assignee: The Regents of The University of California, Oakland, CA (US)

( * ) Notice: Subject to any disclaimer, the term of this patent is extended or adjusted under 35 U.S.C. 154(b) by 172 days.

(21) Appl. No.: 16/469,786

(22) PCT Filed: Dec. 19, 2017

(86) PCT No.: PCT/US2017/067285
§ 371 (c)(1),
(2) Date: Jun. 14, 2019

(87) PCT Pub. No.: WO2018/118903
PCT Pub. Date: Jun. 28, 2018

(65) Prior Publication Data
US 2020/0085964 A1 Mar. 19, 2020

Related U.S. Application Data

(60) Provisional application No. 62/436,147, filed on Dec. 19, 2016, provisional application No. 62/436,149, filed on Dec. 19, 2016, provisional application No. 62/558,566, filed on Sep. 14, 2017.

(51) Int. Cl.
*A61K 47/65* (2017.01)
*A61K 47/69* (2017.01)
*A61K 47/60* (2017.01)
*A61K 47/59* (2017.01)
*A61K 9/20* (2006.01)
*A61K 31/485* (2006.01)

(52) U.S. Cl.
CPC ............ *A61K 47/65* (2017.08); *A61K 9/2036* (2013.01); *A61K 31/485* (2013.01); *A61K 47/59* (2017.08); *A61K 47/60* (2017.08); *A61K 47/6943* (2017.08); *C12Y 304/11* (2013.01); *C12Y 304/21004* (2013.01)

(58) Field of Classification Search
CPC .... A61K 31/485; A61K 9/2036; A61K 47/59; A61K 47/60; A61K 47/6943; A61K 47/65
See application file for complete search history.

(56) References Cited

U.S. PATENT DOCUMENTS

| 5,037,883 A | 8/1991 | Kopecek |
|---|---|---|
| 5,466,479 A | 11/1995 | Frye |
| 5,760,116 A | 6/1998 | Kilgour |
| 6,060,546 A | 5/2000 | Powell |
| 8,497,237 B2 | 7/2013 | Jenkins et al. |
| 8,920,836 B2 | 12/2014 | Hayes |
| 8,969,369 B2 | 3/2015 | Caruso |
| 8,980,291 B2 | 3/2015 | Oshlack |
| 9,084,816 B2 | 7/2015 | McKenna |
| 2004/0116348 A1 | 6/2004 | Chau |
| 2004/0202719 A1 | 10/2004 | Zion |
| 2005/0119762 A1 | 6/2005 | Zilla |
| 2005/0272677 A1 | 12/2005 | Friesen |
| 2007/0123468 A1 | 5/2007 | Jenkins |
| 2009/0004267 A1 | 1/2009 | Arkenau-Maric |
| 2009/0269405 A1 | 10/2009 | Windsor |
| 2012/0183948 A1 | 7/2012 | Howitz |
| 2013/0210854 A1 | 8/2013 | Jenkins |
| 2013/0330409 A1 | 12/2013 | Mohammad |
| 2014/0121152 A1 | 5/2014 | Jenkins |
| 2014/0162935 A1 | 6/2014 | Jenkins |
| 2015/0005332 A1 | 1/2015 | Rariy |
| 2016/0022590 A1 | 1/2016 | Odidi |
| 2016/0136153 A1 | 5/2016 | Jenkins |
| 2018/0369236 A1 | 12/2018 | Rariy |
| 2019/0262335 A1 | 8/2019 | Rariy |

FOREIGN PATENT DOCUMENTS

| WO | 1992001477 A1 | 2/1992 |
|---|---|---|
| WO | 2000064486 A2 | 11/2000 |
| WO | 2004027045 A2 | 4/2004 |
| WO | 2006121552 A2 | 11/2006 |
| WO | 2016115234 A1 | 7/2016 |

(Continued)

OTHER PUBLICATIONS

European Patent Office. Extended European Search Report for application 17883381.0 dated Jul. 17, 2020.
McBride, M. C., et al. "Persistence of antimicrobial activity through sustained release of triclosan from pegylated silicone elastomers." Biomaterials 30.35 (2009): 6739-6747.
Morgan, S. M., et al. "Alginates as drug carriers: covalent attachment of alginates to therapeutic agents containing primary amine groups." International journal of pharmaceutics 122.1-2 (1995): 121-128.
Alexander, L., et al. "Development and impact of prescription opioid abuse deterrent formulation technologies." Drug and alcohol dependence 138 (2014): 1-6.

(Continued)

*Primary Examiner* — Genevieve S Alley
(74) *Attorney, Agent, or Firm* — Quarles & Brady LLP

(57) ABSTRACT

Non-crushable pill formulations and methods of using the formulations are disclosed. A non-crushable pill formulation for preventing unintended use of a drug, comprising a polymer, the polymer forming a polymer backbone of the complex; cross-linkers, the cross-linkers connecting the polymer backbone through covalently bonding to form at least one inner cavity within the complex; and the drug, the drug being trapped either covalently or non-covalently in the at least one inner cavity within the complex, wherein the drug is protected from releasing outside of the complex.

18 Claims, 30 Drawing Sheets

(56) References Cited

FOREIGN PATENT DOCUMENTS

WO 2016142290 A1 9/2016

OTHER PUBLICATIONS

Burns, L. H.; et al. In Opiate Receptors and Antagonists: From Bench to Clinic; Dean, R. L., Bilsky, E. J., Negus, S. S., Eds. 2009, p. 247-261.

Cicero, T. J., et al. "Abuse-deterrent formulations and the prescription opioid abuse epidemic in the United States: lessons learned from OxyContin." JAMA psychiatry 72.5 (2015): 424-430.

Dowling, J., et al. "Population pharmacokinetics of intravenous, intramuscular, and intranasal naloxone in human volunteers." Therapeutic drug monitoring 30.4 (2008): 490-496.

Finch, J. W., et al. "Two-year experience with buprenorphine-naloxone (Suboxone) for maintenance treatment of opioid dependence within a private practice setting." Journal of Addiction Medicine 1.2 (2007): 104-110.

Hale, M. E., et al. "Efficacy and safety of OPANA ER (oxymorphone extended release) for relief of moderate to severe chronic low back pain in opioid-experienced patients: a 12-week, randomized, double-blind, placebo-controlled study." The Journal of Pain 8.2 (2007): 175-184.

Hyung Park, J., et al. "Hydrogels based on poly (ethylene oxide) and poly (tetramethylene oxide) or poly (dimethyl siloxane). III. In vivo biocompatibility and biostability." Journal of Biomedical Materials Research Part A. 64.2 (2003): 309-319.

International Searching Authority, International Search Report & Written Opinion for application PCT/US2017/067285, dated Mar. 9, 2018.

Jovanovic, J. D., et al. "The thermogravimetric analysis of some polysiloxanes." Polymer Degradation and Stability 61.1 (1998): 87-93.

Kunøe, N., et al. "Retention in naltrexone implant treatment for opioid dependence." Drug and alcohol dependence 111.1-2 (2010): 166-169.

Munshi, O. "The role of Embeda (morphine sulfate-naltrexone hydrochloride) in opioid abuse: a systematic review of literature." The Journal of Pain 14.4 (2013): S11.

Orman, J. S., et al. "Buprenorphine/naloxone." Drugs 69.5 (2009): 577-607.

Raffa, R. B., et al. "Opioid formulations designed to resist/deter abuse." Drugs 70.13 (2010): 1657-1675.

Signature Therapeutics. Bio-MD™ Opioids: Abuse-Resistant Opioids. [Online Early Access]. http://www.signaturerx.com/view.cfm/59/Abuse-Resistant-Opioids. Accessed on Feb. 21, 2015.

Stanos, S. P., et al. (Jul. 2012). Strategies to reduce the tampering and subsequent abuse of long-acting opioids: potential risks and benefits of formulations with physical or pharmacologic deterrents to tampering. In Mayo Clinic Proceedings (vol. 87, No. 7, pp. 683-694) Elsevier.

The Medical letter on drugs and therapeutics. Abuse-Deterrent Opioid Formulations. 2015, 57, 71-72.

The Medical letter on drugs and therapeutics. Extended-Release Hydromorphone (Exalgo) for Pain. 2011, 53, 62-63.

The Medical letter on drugs and therapeutics. Tapentadol (Nucynta)—A New Analgesic. 2009, 51, 61-62.

Van Dorp, Ela, et al. "Naloxone treatment in opioid addiction: the risks and benefits." Expert opinion on drug safety 6.2 (2007): 125-132.

Webster, L. R. "Oxytrex®: an oxycodone and ultra-low-dose naltrexone formulation." Expert opinion on investigational drugs 16.8 (2007): 1277-1283.

Wen, J., et al. "Controlled protein delivery based on enzyme-responsive nanocapsules." Advanced materials 23.39 (2011): 4549-4553.

Yanbing, W., et al. "Mechanical and thermal properties of polysiloxanes and NBR blend elastomer." Journal of Wuhan University of Technology-Mater. Sci. Ed. 21.4 (2006): 92-94.

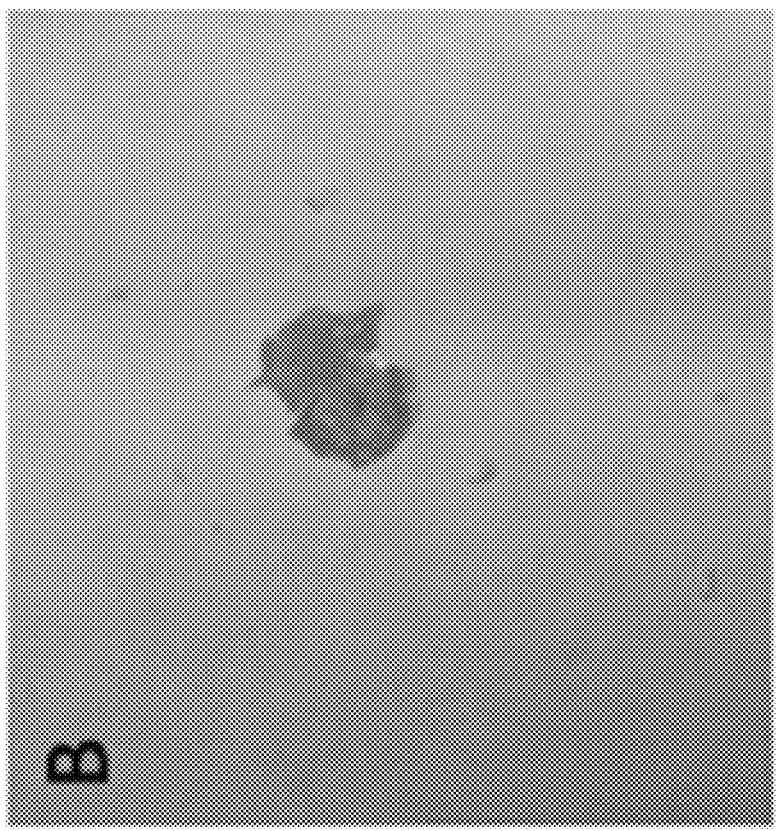
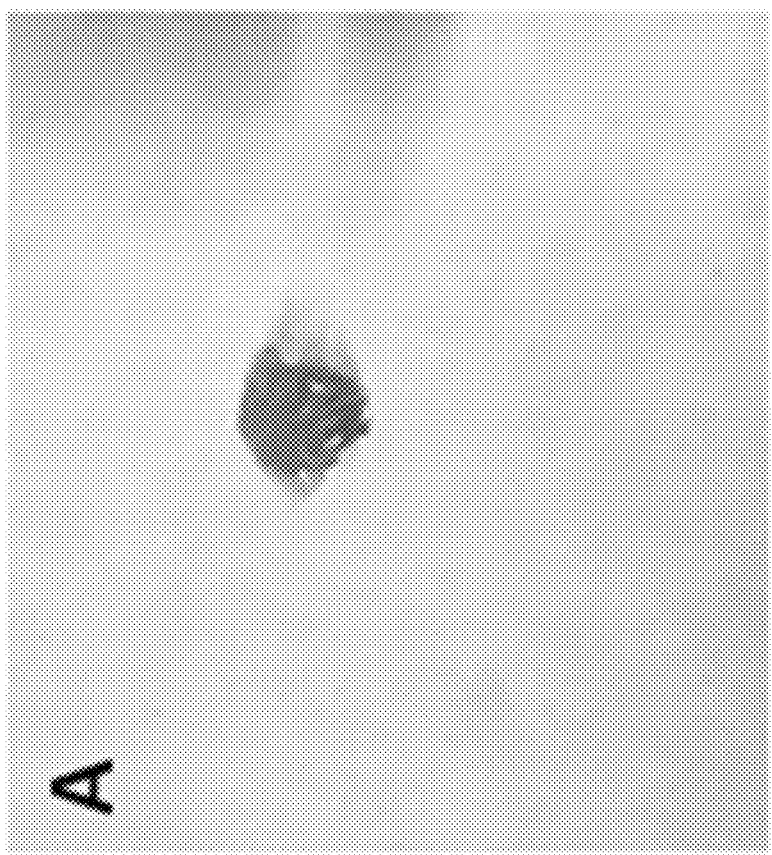
FIGS. 6A-B

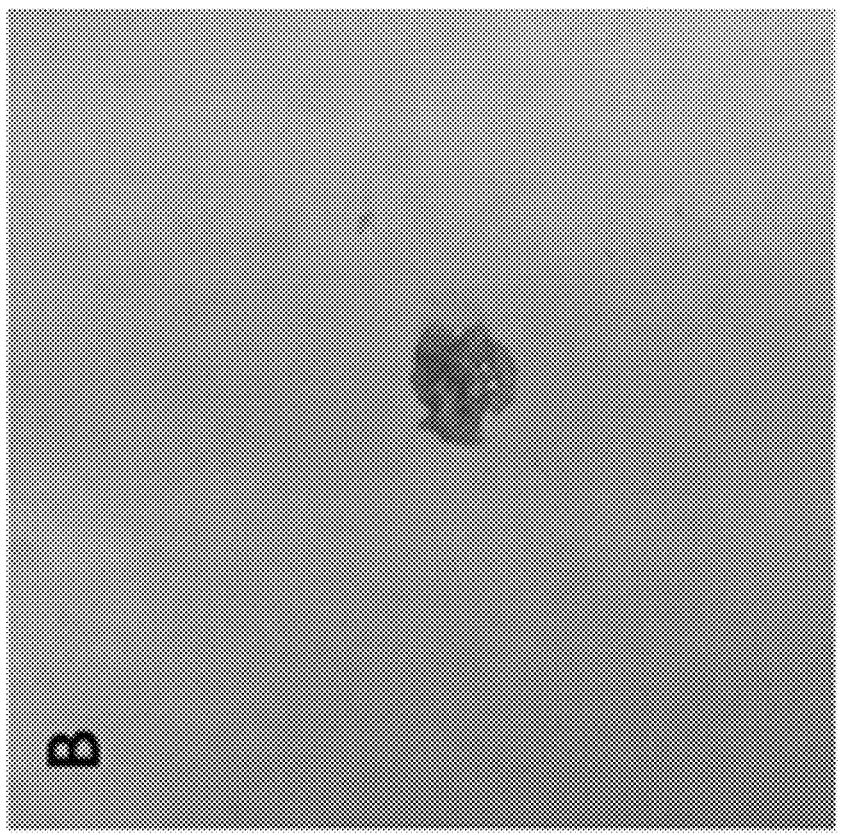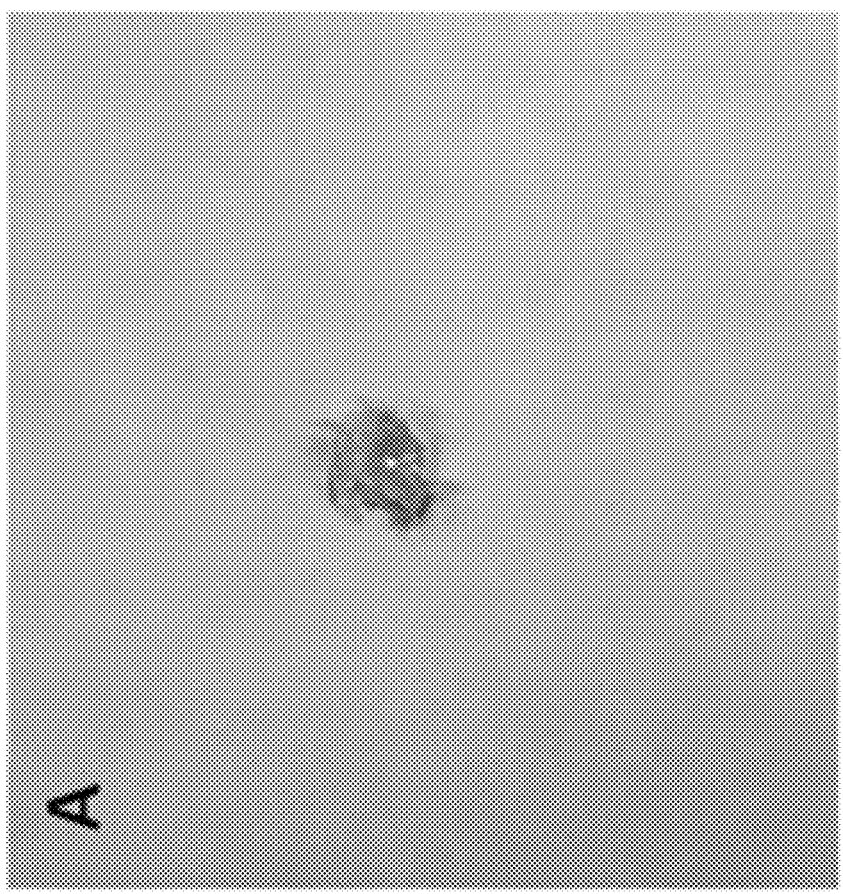
FIG. 8A-B

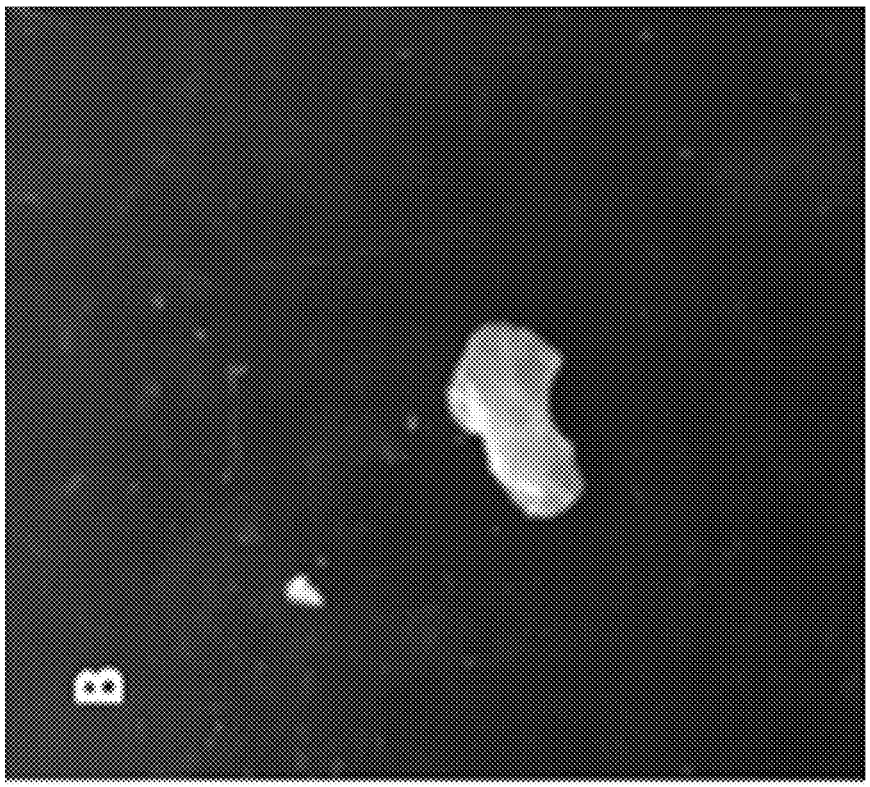
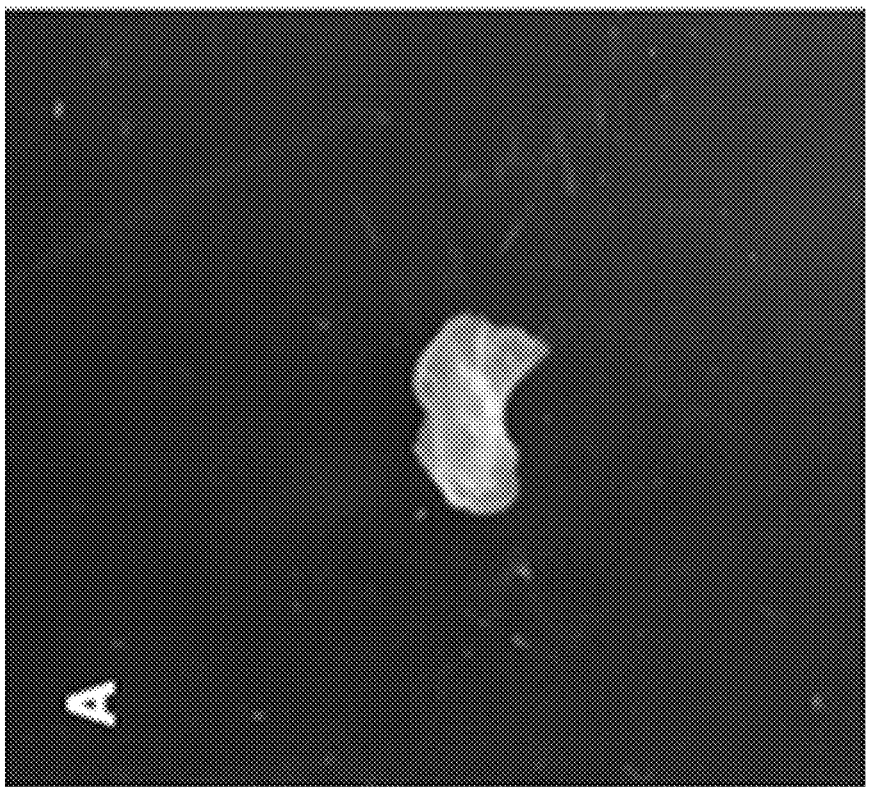
FIGS. 9A-B

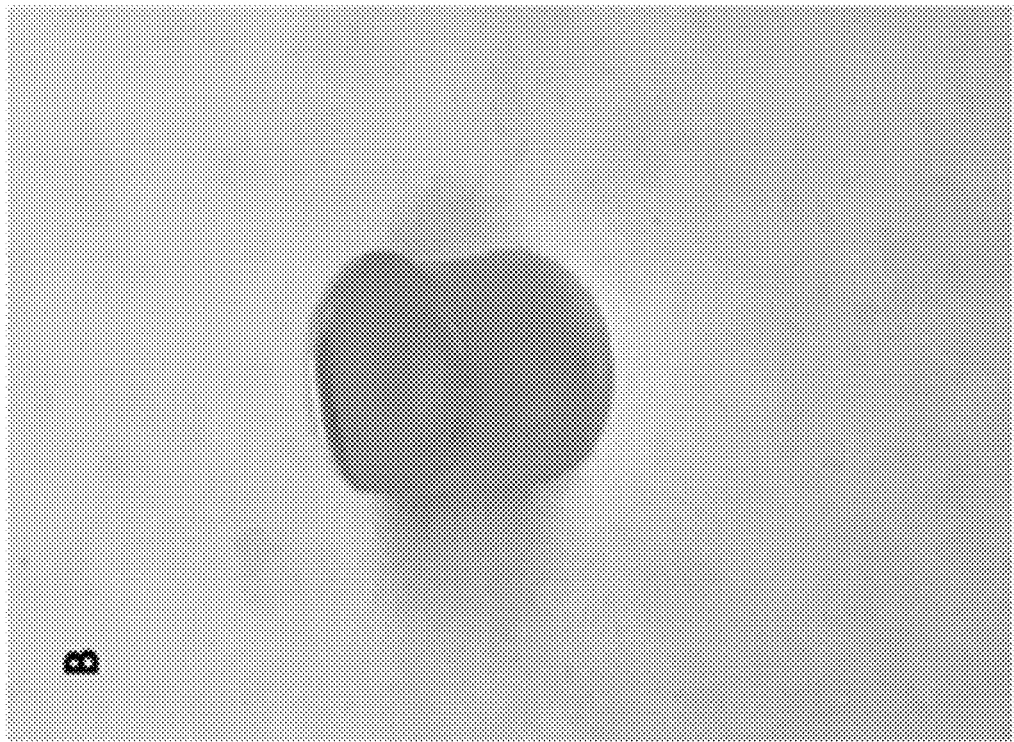
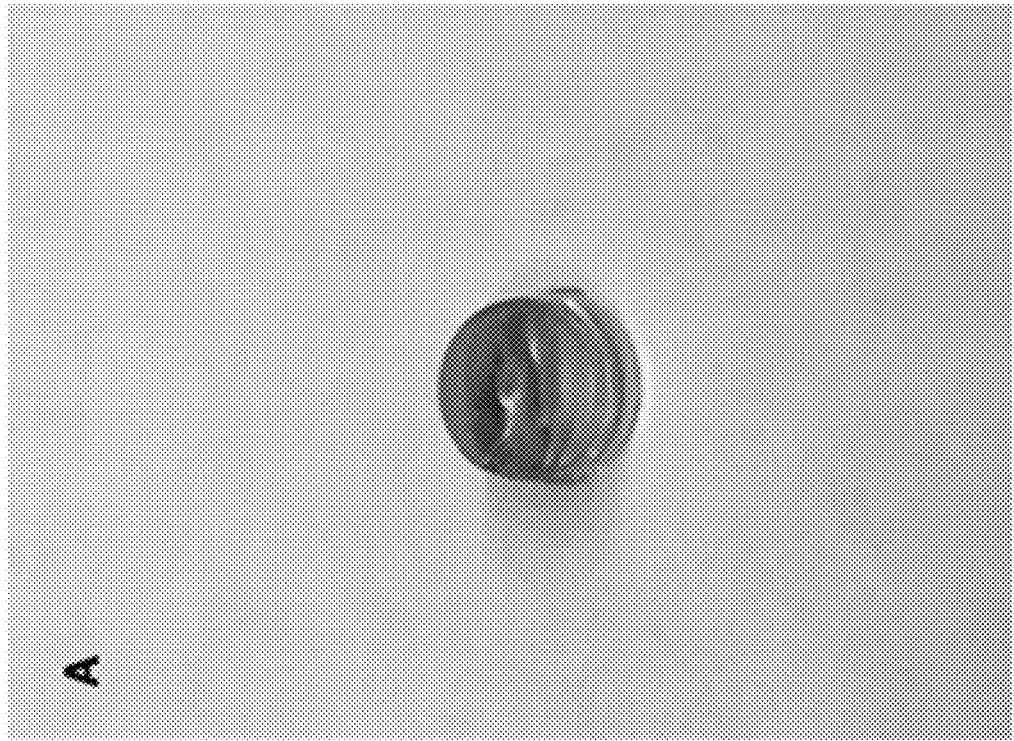
FIGS. 10A-B

Dual enzyme cross-linker:
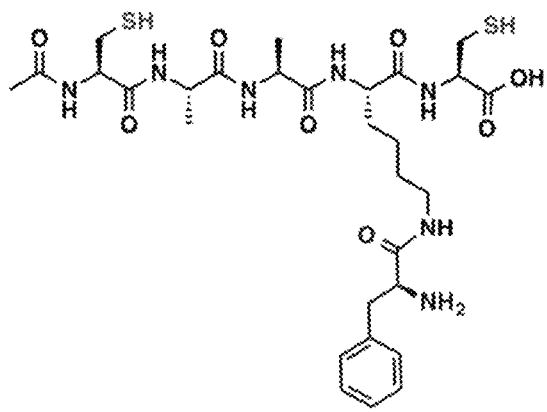
Dual enzyme one cysteine:
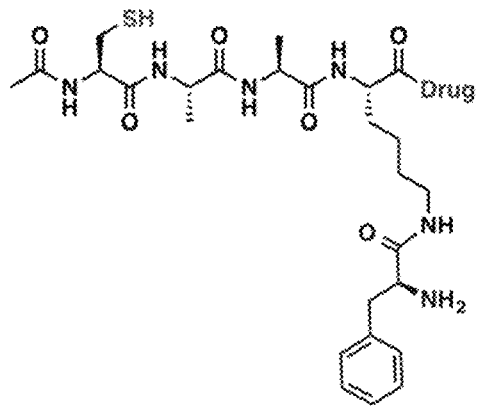
Trypsin only cross-linker:
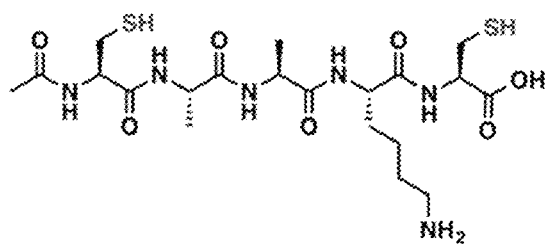
Trypsin only one cysteine:
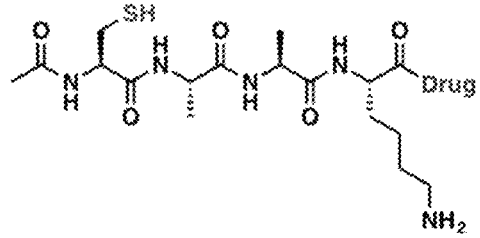
Chymotrypsin only cross-linkers:
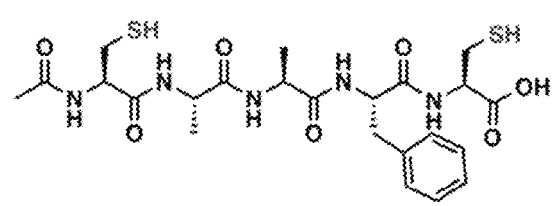
Chymotrypsin only one cysteine:
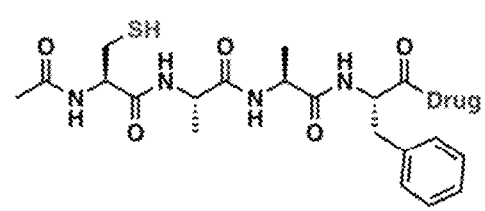
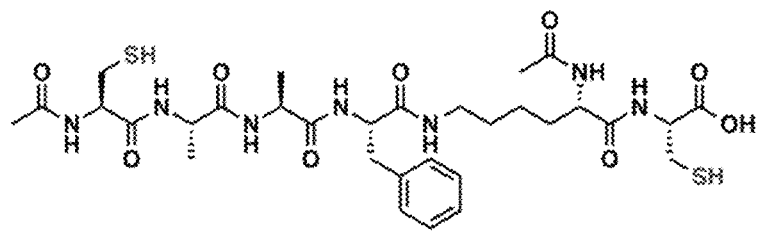
FIG. 11

| Condition | Time Subjected | Pass/Fail |
|---|---|---|
| General Test (24°C) | | Pass |
| Microwave | 1 | Pass |
| Microwave | 5 | Pass |
| Microwave | 10 | Burned |
| Microwave | 20 | Burned |
| Oven Heating (260°C) | 15 | Pass |
| Oven Heating (260°C) | 30 | Pass |
| Oven Heating (260°C) | 60 | Pass |
| Cooling (4°C) | 12h | Pass |
| Cooling (4°C) | 24h | Pass |
| Cooling (18°C) | 12h | Pass |
| Cooling (18°C) | 24h | Pass |

R = H, Acetamide, Protecting Group, Amino Acid, Peptide

Scheme 9. Noncrushable cross-linked polymer for non-abusable formulations.

Scheme 13. Synthesis of CAAK(F)-diamino-Naltrexone thionocarbamate (FIG 27) and CAAK(F)-diamino-Naltrexone carbamate.

Scheme 14. Crosslinking of the PDMS-CAAK(F)-diamino-Naltrexone-polysiloxane conjugate with 4-arm PEG-SH.

NONCRUSHABLE PILL FORMULATIONS

CROSS-REFERENCE TO RELATED APPLICATION(S)

This application represents the National Phase Entry of International Application PCT/US2017/067285, filed Dec. 19, 2017; which claims benefit of U.S. Provisional Application 62/436,147 filed Dec. 19, 2016, U.S. Provisional Application 62/436,149, filed Dec. 19, 2016, and U.S. Provisional Application 62/558,566 filed Sep. 14, 2017, all of which are incorporated herein by reference for all purposes. This application relates to International Application PCT/US2017/067284, filed Dec. 19, 2017 entitled, "DualEnzyme Responsive Peptides" with inventors Heather D. Maynard and Natalie Boehnke, which is hereby incorporated herein by reference for all purposes.

STATEMENT REGARDING FEDERALLY SPONSORED RESEARCH OR DEVELOPMENT

This invention was made with government support under Grant Number HL119893, awarded by the National Institutes of Health. The government has certain rights in the invention.

BACKGROUND

Abuse of opioid analgesic alkaloids such as oxycodone is a major societal problem. It is estimated that nearly a third of people who abuse drugs started with prescription medicines; 2.4 million Americans used prescription drugs recreationally in 2010 and 15,000 people in the U.S. alone died in 2009 because of overdose from prescription pain relievers; many more burdened hospitals and medical facilities.[1,2] Misuse of drugs like oxycodone is carried out by crushing the pills for immediate burst release, typically by nasal insufflation, or by liquefying the pills for intravenous injection. In both cases the immediate dosage is higher, causing euphoria, which perpetuates abuse. Thus, there is a strong impetus to develop formulations that prevent and deter misuse. For example, the U.S. Food and Drug Administration has made preventing abuse a priority, the Centers for Disease Control and Prevention have determined that prescription drug abuse is an epidemic, and the Obama administration released a Prescription Drug Abuse Prevention Plan in 2011.[2] Despite strong efforts, abusers have found ways around new non-crushable and non-dissolvable pills by dissolving in solutions found in the home or subjecting the pills to extreme temperatures in microwaves to melt the materials. We disclose in this invention a method to prevent abuse of drugs such as oxycodone, a commonly prescribed opioid, through the use of a non-crushable and non-dissolvable elastomeric polymer formulation. Oxycodone will be physically trapped or covalently bound inside elastomeric polymer micro particles too large to syringe via linkages that can only be degraded by enzymes in the stomach or intestine. We anticipate that the drug delivery vehicles described herein could replace current formulations for these patients since the drug itself is the same, but the formulation is superior to current formulations in preventing misuse of the product.

Needed in the art are drug delivery vehicles and non-crushable pill formulations which are specifically designed to avoid misuse of the drug such as opioid.

SUMMARY OF THE INVENTION

In one aspect, the present disclosure is a complex for preventing unintended use of a drug. The complex comprises a polymer, the polymer forming a polymer backbone of the complex; cross-linkers, the cross-linkers connecting the polymer backbone through covalently bonding to form at least one inner cavity within the complex; and the drug, the drug being trapped either covalently or non-covalently in the at least one inner cavity within the complex, wherein the drug is protected from releasing outside of the complex.

In one embodiment, the polymer forms an elastomer.

In one embodiment, the polymer has a glass transition temperature (Tg) lower than 23° C.

In one embodiment, the elastomer has a glass transition temperature (Tg) lower than 4° C.

In one embodiment, the elastomer has a glass transition temperature (Tg) lower than −18° C.

In one embodiment, the polymer is a polysiloxane.

In one embodiment, the polysiloxane has a glass transition temperatures (Tg) in the range of −140° C. to −20° C.

In one embodiment, the drug is non-covalently encapsulated in at least one inner cavity within the complex by a cross-linked elastomeric network.

In one embodiment, the cross-linkers further comprise a polymer dithiol or a polymer multithiol such as a star polymer multithiol.

In one embodiment, the polymer dithiol or a polymer multithiol is a polyethylene glycol (PEG) dithiol or multithiol. In one embodiment, the polymer multithiol is 4-arm star PEG tetrathiol.

In one embodiment, the enzyme responsive peptide comprises an amino acid having an α-amino group, an α-carboxylic acid group and an ε-amine group, wherein the α-amino group is covalently bonded with a second amino acid or a peptide, and the α-carboxylic acid is covalently bonded with a first group.

In one embodiment, the ε-amine is a free amine.

In one embodiment, the ε-amine is covalently bonded with a second group.

In one embodiment, the second group is an enzyme substrate.

In one embodiment, the enzyme substrate is a protease substrate cleavable under digestion of an enzyme of chymotrypsin or other enzyme found in the stomach or intestine.

In one embodiment, the amino acid is a lysine.

In one embodiment, the second amino acid or the peptide comprises a free thiol group.

In one embodiment, the peptide comprises a cysteine.

In one embodiment, the first group comprises a free thiol cysteine.

In one embodiment, the first group comprises a cysteine.

In one embodiment, the first group comprises the drug. In one embodiment, the drug is attached to the complex through a self-immolative linker.

In one embodiment, the enzyme responsive peptide requires digestion by at least one enzyme to cleave the bond between the α-carboxylic acid and the first group or the bond between the α-amino group and the second amino acid or the peptide.

In one embodiment, the enzyme responsive peptide requires digestion by at least one enzyme to cleave the bond between the α-carboxylic acid and the first group.

In one embodiment, the enzyme responsive peptide requires digestion by two separate enzymes to cleave the bond between the α-carboxylic acid and the first group.

In one embodiment, the enzyme responsive peptide is cleavable under the digestion of an enzyme selected from the group consisting of trypsin, chymotrypsin, and any other enzyme found in the stomach or intestine.

In one embodiment, the enzyme responsive peptide is cleavable under the digestion of two enzymes selected from the group consisting of trypsin, chymotrypsin, gastric lipase, pepsin, aminopeptidase, carboxypeptidase, deoxyribonuclease, dipeptidase, elastase, enterokinase, lactase, maltase, pancreatic amylase, pancreatic lipase, sucrase, dextrinase, nucleosidases, phosphatases, and any other enzyme found in the stomach or intestine.

In one embodiment, the enzyme responsive peptide is cleavable under the digestion of two enzymes selected from the enzyme pair group of trypsin/chymotrypsin or any combination of gastric lipase, pepsin, aminopeptidase, carboxypeptidase, chymotrypsin, trypsin, deoxyribonuclease, dipeptidase, elastase, enterokinase, lactase, maltase, pancreatic amylase, pancreatic lipase, sucrase, dextrinase, nucleosidases, phosphatases, or any other enzyme found in the stomach or intestine.

In one embodiment, the enzyme responsive peptide comprises an amino acid having an α-amino group, an α-carboxylic acid group and a hydrophobic group, wherein the α-amino group is covalently bonded with a second amino acid or a peptide, and the α-carboxylic acid is covalently bonded with a first group.

In one embodiment, the hydrophobic group is an aromatic group.

In one embodiment, the hydrophobic group is a phenyl or its derivatives, a benzyl or its derivatives, or an indole or its derivatives.

In one embodiment, the hydrophobic group is a benzyl group.

In one embodiment, the amino acid is phenylalanine.

In one embodiment, the second amino acid or the peptide comprises a free thiol group.

In one embodiment, the peptide comprises a cysteine.

In one embodiment, the first group comprises a free thiol group.

In one embodiment, the first group comprises a cysteine.

In one embodiment, the first group comprises the drug. In one embodiment, the drug is attached to the complex through a self-immolative linker.

In one embodiment, the enzyme responsive peptide requires digestion by at least one enzyme to cleave the bond between the α-amino group and the second amino acid or the peptide or the bond between the α-carboxylic acid and the first group.

In one embodiment, the enzyme responsive peptide requires digestion by at least one enzyme to cleave the bond between the α-carboxylic acid and the first group.

In one embodiment, the enzyme responsive peptide is cleavable under the digestion of an enzyme selected from the group consisting of trypsin, chymotrypsin, gastric lipase, pepsin, aminopeptidase, carboxypeptidase, chymotrypsin, trypsin, deoxyribonuclease, dipeptidase, elastase, enterokinase, lactase, maltase, pancreatic amylase, pancreatic lipase, sucrase, dextrinase, nucleosidases, phosphatases, and any other enzyme found in the stomach or intestine.

In one aspect, the disclosure relates to a polymeric formulation for controlled releasing an active ingredient and the formulation comprises any of the complex as discussed above.

BRIEF DESCRIPTION OF THE DRAWINGS

FIGS. 6A-B are a set of photos showing pictures of the elastomer obtained from PMVS with PEG dithiol and peptide (20% cross-linking in total) showing non-crushable property before crushing test (FIG. 6A) and after crushing test (FIG. 6B). The elastomer was left in a −20° C. freezer overnight before the crushing test using a hammer.

FIGS. 8A-B are a set of photos showing the elastomer obtained from PMVS0.2-co-PDMS0.8 with PEG dithiol and peptide (20% cross-linking in total) showed non-crushable property (FIG. 8A: before crushing test, FIG. 8B: after crushing test). The elastomer was left in a −20° C. freezer overnight before the crushing test using a hammer.

FIGS. 9A-B are a set of photos showing the elastomer obtained from PMVS with peptide (10% cross-linking) showing reduced shattering/cracking property upon induced stress (FIG. 9A: before crushing test, FIG. 9B: after crushing test). The elastomer was left in a −20° C. freezer overnight before the crushing test using a hammer.

FIGS. 10A-B are a set of photos showing elastomer obtained from PMVS with PEG dithiol containing naltrexone (FIG. 10A) and naltrexone HCl (FIG. 10B).

FIG. 11 is a graph showing chemical structures of some exemplary peptides according to certain embodiments of the present invention.

DETAILED DESCRIPTION OF THE INVENTION

In General

Figure 1:
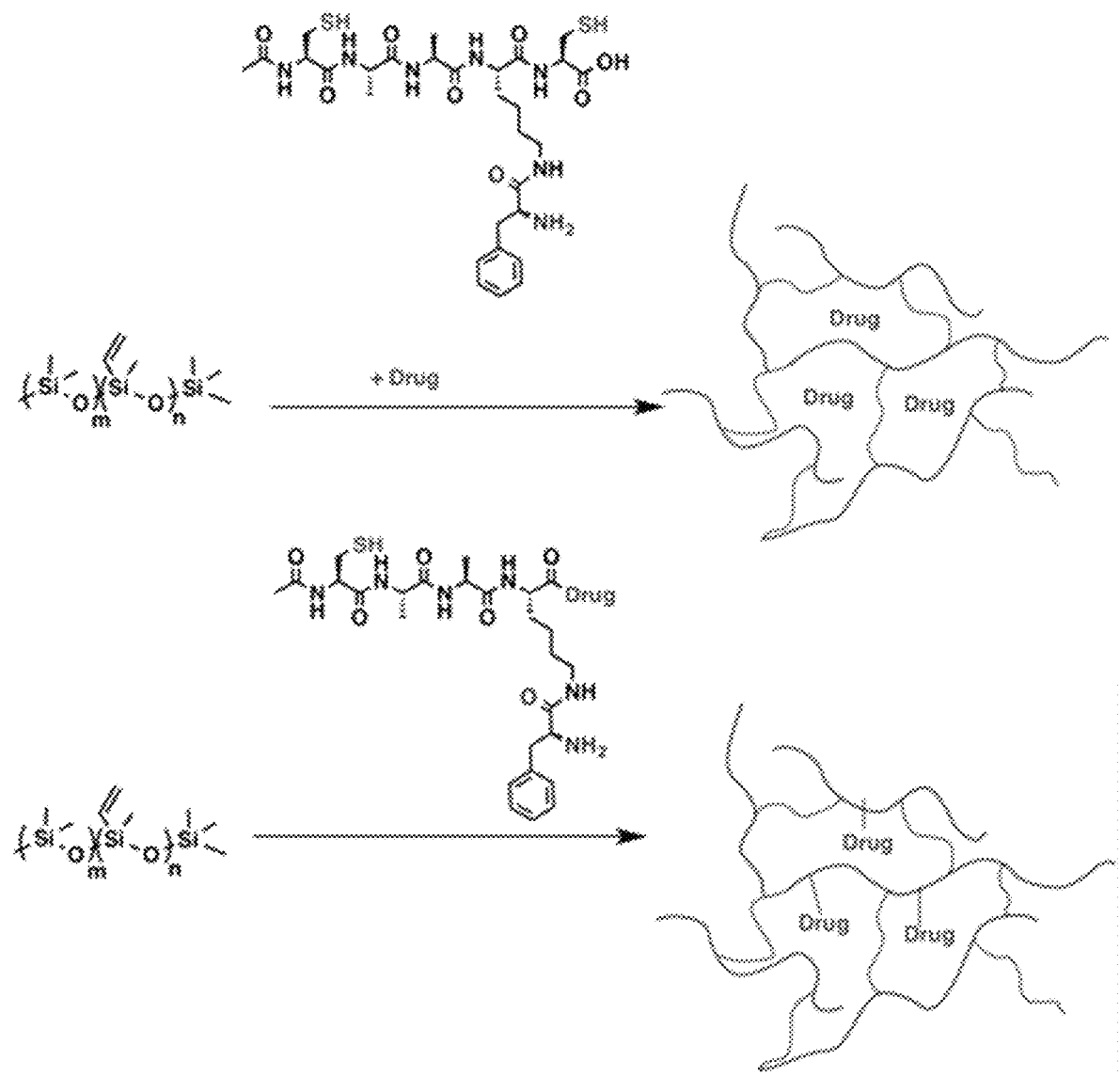
FIG. 1 is a set of diagrams showing synthesis and design of siloxane elastomers with drug entrapped or covalently attached using a representative example dual-enzyme responsive peptide as the cross-linker.
Figure 2:
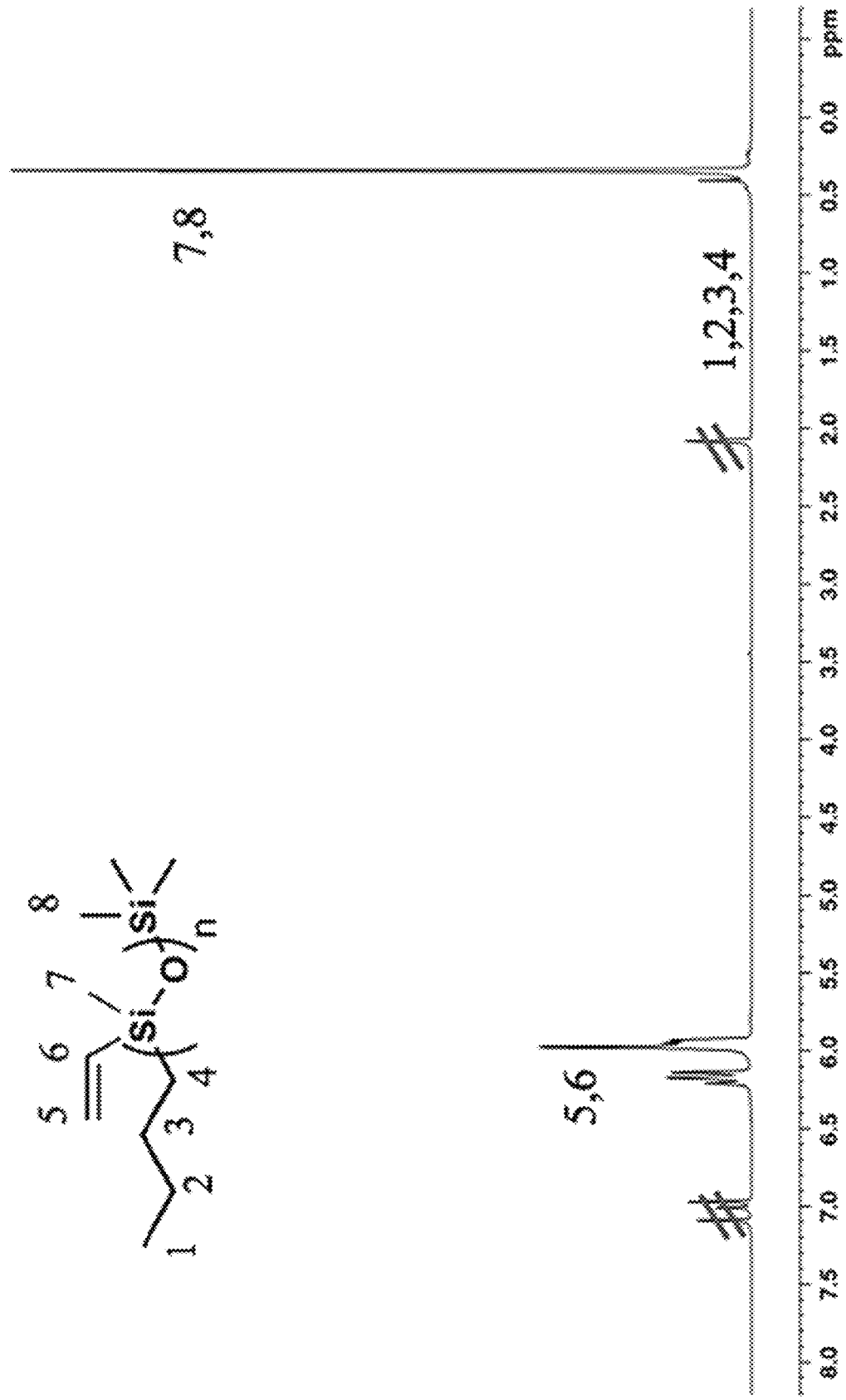
FIG. 2 is a graph showing $^1$H NMR spectra of PMVS ($d_8$-toluene, 500 MHz).
Figure 3:
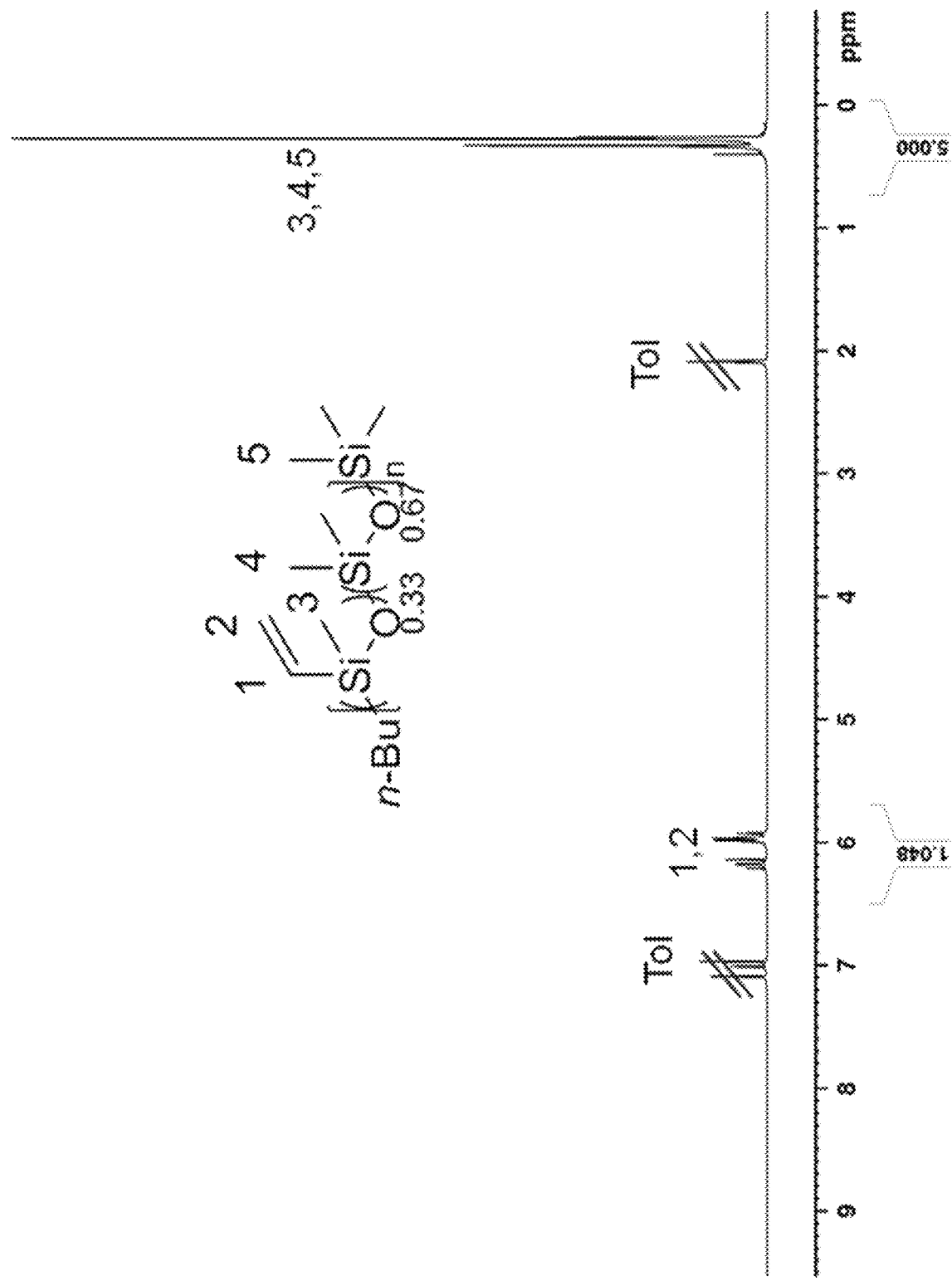
FIG. 3 is a graph showing $^1$H NMR spectra of PVD2$_{0.33}$-co-PDMS$_{0.67}$ (d8-toluene, 500 MHz).
Figure 4:
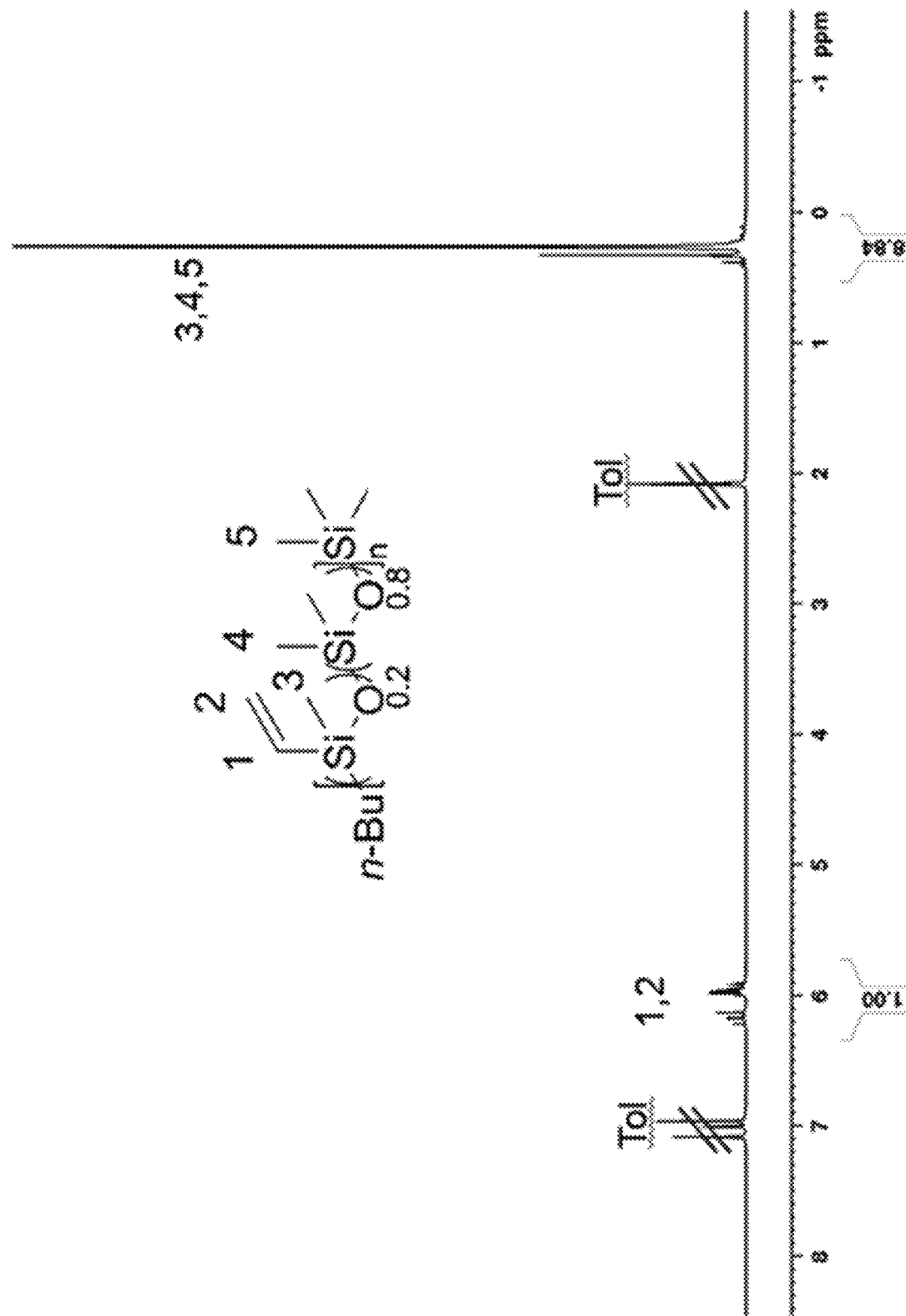
FIG. 4 is a graph showing $^1$H NMR of PVD2$_{0.2}$-co-PDMS$_{0.8}$ copolymer (d8-toluene, 500 MHz).

Before the present materials and methods are described, it is understood that this invention is not limited to the particular methodology, protocols, materials, and reagents described, as these may vary. It is also to be understood that the terminology used herein is for the purpose of describing particular embodiments only and is not intended to limit the scope of the present invention which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably.

Unless defined otherwise, all technical and scientific terms used herein have the same meanings as commonly understood by one of ordinary skill in the art. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Definitions

Unless defined otherwise, all technical and scientific terms used herein have the same meaning as commonly understood by one of ordinary skill in the art to which this invention belongs. As used herein the following terms have the following meanings.

The term "comprising" or "comprises," as used herein, is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about," when used before a numerical designation, e.g., temperature, time, amount, and concentration, including range, indicates approximations which may vary by (+) or (−) 10%, 5% or 1%.

The term "functional group," as used herein, refers to any of numerous combinations of atoms that form parts of chemical molecules, that undergo characteristic reactions themselves, and that influence the reactivity of the remainder of the molecule. Typical functional groups include, but are not limited to, hydroxyl, carboxyl, aldehyde, carbonyl, amino, azide, alkynyl, thiol and nitril. Potentially reactive functional groups include, for example, amines, carboxylic acids, alcohols, double bonds, and the like. Preferred functional groups are potentially reactive functional groups of amino acids such as amino groups or carboxyl groups.

The term "non-crushable," as used herein, refers to a material or a structure which cannot be easily or readily crushed. For example, a drug-coating material can be easily crushed if the material can be even partially fragmented by hand pressure using a solid surface, such as a spoon or pestle.

The term "crushing," as used herein, refers to preparing particles small enough to pass through a typical syringe needle. This typically means <500 microns. There is well-known unintended use of a drug that involves a person crushing a formulation with a hammer, by shaving, with a spoon, or with anything available.

In one embodiment, the term "non-crushable" means that when a drug-abuser uses those methods (or any methods of unintended use of a drug) the material would still be >500 microns or not be small enough to take up in a syringe for injection or for nasal snorting (i.e., insufflated through the nose) for any unintended use.

In one embodiment, the present invention relates to a non-crushable polymer within which a chemical or biological agent may be trapped or protected. In one embodiment, the chemical or biological agent may be trapped or covalently attached (bonded) within the non-crushable polymer through enzyme sensitive or responsive peptides. In one specific embodiment, the non-crushable polymer has low glass transition temperatures (Tg) (e.g., <−18° C.) so that it could not be easily crushed for unintended use. Because of enzyme sensitive peptides, the drug can be enzymatically released from the non-crushable polymer in the stomach or intestines for persons who take the pills as intended through an oral route.

The term "complex," as used herein, refers to a structure comprising molecules or substances which are interconnected to each other by any connective forces. In one embodiment, a complex of the present invention comprises a polymeric structure inter-connected by cross-linkers and the polymeric structure has at least one inner cavity for holding and protecting chemical or biological agents from releasing.

The term "cross-linking," as used herein, refers to an attachment of two chains of a polymer molecule by bridges, composed of either an element, a group, or a compound, that join certain atoms of the chains by chemical bonds.

The term "cross-linker," as used herein, refers to the element, group, or compound that effects cross-linking between polymer chains. In one embodiment, the cross-linkers comprise enzyme sensitive or responsive peptides. In one embodiment, the cross-linkers comprise other general acceptable linkers such as those in thiol-ene chemistry, those in click chemistry, those in oxime chemistry, those in alkyne/azide chemistry, those in supramolecular chemistry or others. In one embodiment, the cross-linkers comprise other general acceptable linkers such as dithiols or star polymers containing multiple thiols. For example, the present disclosure uses linear PEG dithiol or a multiarm PEG with a thiol at the end of each chain. The examples include 4-arm PEG tetrathiols. In one embodiment, the cross-linkers comprise a multiarm PEG with thiols at each end. In one embodiment, the cross-linkers comprise 4-arm PEG tetrathiol. In one embodiment, the cross-linkers comprise polyethylene glycol (PEG) dithiol. In one embodiment, the cross-linkers comprise both enzyme sensitive or responsive peptides and PEG dithiols or 4-arm PEG tetrathiol.

The term "PEG" or "polyethylene glycol," as used herein, refers to an oligomer or polymer or branched or star polymer of ethylene oxide.

The term "PEG dithiol," as used herein, refers to a PEG having two thiol groups at the ends of the PEG. In one embodiment, a PEG dithiol may be used as a cross-linker in the present invention.

The term "inner cavity," as used herein, refers to a hollow area within the polymer structure and the complex. This hollow area may have different shapes and sizes. In one embodiment, the inner cavity is large enough to hold a chemical or biological molecule, such as a drug.

The term "drug," "schedule drug," "controlled drug," "controlled pharmaceutical agent" or "controlled substance," as used herein, refers to a prescribed medication having the potential for abuse. In one embodiment, the drug refers to oxycodone or any other commonly prescribed opioid.

The term "abuse," as used herein, refers to use of a drug (e.g., an oxycodone) in an inappropriate or non-prescription amount or frequency.

The term "opioid," as used herein, refers to a natural (e.g., morphine), semi-synthetic (e.g., buprenorphine) or synthetic (e.g., meptazinol) drug that acts by binding to one or more of the opioid receptors in the brain, thus displacing an endogenous analgesic ligand, namely an enkephalin or endorphin, and having a therapeutically useful pain-relieving effect.

The term "polymer," as used herein, refers to a macromolecule or a polymer made from one or more different monomers, such as a copolymer, a terpolymer, a tetrapolymer, a pentapolymer etc., and may be any of a random, block, graft, sequential or gradient polymer. The term "polymer" may also include copolymers and polymers within its scope.

The term "elastomer," as used herein, refers to any polymer or combination of polymers consistent with the ASTM D1566 definition of "a material that is capable of recovering from large deformations, and can be, or already is, modified to a state in which it is essentially insoluble (but can swell) in boiling solvent." The term "elastomer" may be used interchangeably with the term "rubber." Preferred elastomers have a melting point that cannot be measured by differential scanning calorimetry (DSC) or if it can be measured by DSC is less than 20° C., or less than 0° C. Preferred elastomers may have a Tg less than −18° C. as measured by DSC.

The term "subject," or "patient," as used herein, refers to humans and other mammals, such as domestic animals (e.g., dogs and cats).

The term "siloxane," as used herein, refers to any chemical compound having a short repeating unit of silicon and oxygen atoms with organic side chains.

The term "polysiloxane," as used herein, refers to an extended siloxane repeat unit.

The term "active agent," "chemical agent" or "biological agent," as used herein, refers to an agent that may find use in the treatment, diagnosis and/or management of a disease state. In one embodiment, the active agent is a drug, such as oxycodone or any other commonly prescribed opioid.

The term "degraded" or "degradable," as used herein, refers to chemical bonds of a substance cleavable under certain conditions so that the substance may be decomposed. In one embodiment, the peptide bonds of enzyme sensitive or responsive peptides may be degradable under specific conditions so that a drug held within the complex or covalently attached to the complex may be released in the stomach or intestines for persons who take the pills as intended.

The term "monomer," as used herein, refers to any discrete chemical compound of any molecular weight.

The term "hydrophobic," as used herein, refers to a molecule or portion of a molecule that tends to repel, or not to combine with, or is incapable of dissolving in water.

The term "enzyme" and "enzymes," as used herein, refers generally to proteins that catalyze biochemical reactions. Enzymes may be proteins that generally enable chemical transformations of organic compounds. Enzymes may be powerful catalysts because they are highly specific.

Preferably the enzymes may be selected from the group consisting of lyases, hydrolases, oxidoreductases, transferases, isomerases, and ligases, and combinations thereof. In general, six classes or types of enzymes (as classified by the type of reaction that is catalyzed) may be recognized. Enzymes catalyzing reduction/oxidation or redox reactions may be referred to generally as EC 1 (Enzyme Class 1) Oxidoreductases. Enzymes catalyzing the transfer of specific radicals or groups may be referred to generally as EC2 (Enzyme Class 2) Transferases. Enzymes catalyzing hydrolysis may be referred to generally as EC 3 Hydrolases. Enzymes catalyzing removal from or addition to a substrate of specific chemical groups may be referred to generally as EC 4 Lyases. Enzymes catalyzing isomerization may be referred to generally as EC 5 Isomerases. Enzymes catalyzing combination or binding together of substrate units may be referred to generally as EC 6 Ligases. Hydrolase enzymes may include, but are not limited to, a lipase, a phosphatase, an amylase, a cellulase, a protease, a peptidase, a urease, or a deaminase.

Enzymes such as amylases and proteases break down large molecules (starch or proteins, respectively) into smaller ones, so they can be absorbed by the intestines. Starch molecules, for example, may be too large to be absorbed from the intestine, but enzymes hydrolyze the starch chains into smaller molecules such as maltose and eventually glucose, which can then be absorbed. Different enzymes may digest different food substances. In ruminants, which have herbivorous diets, microorganisms in the gut produce another enzyme, cellulase, to break down the cellulose cell walls of plant fiber.

The term "trypsin," as used herein, refers to a serine protease from the PA clan (Proteases of mixed nucleophile, superfamily A) superfamily. Trypsin can be found in the digestive system of many vertebrates, where it hydrolyses proteins. Trypsin may be formed in the small intestine when its proenzyme form, the trypsinogen produced by the pancreas, is activated. Trypsin can cleave peptide chains mainly at the carboxyl side of the amino acids lysine or arginine, except when either is followed by proline. It may be used for numerous biotechnological processes. The process may be commonly referred to as trypsin proteolysis or trypsinisation, and proteins that have been digested/treated with trypsin are said to have been trypsinized.

The term "chymotrypsin," as used herein, refers to a digestive enzyme component of pancreatic juice acting in the duodenum where it performs proteolysis, the breakdown of proteins and polypeptides. Chymotrypsin may preferentially cleave peptide amide bonds where the carboxyl side of the amide bond (the P1 position) is a large hydrophobic amino acid (tyrosine, tryptophan, and phenylalanine). These amino acids may contain an aromatic ring in their sidechain that fits into a 'hydrophobic pocket' (the S1 position) of the enzyme. It is activated in the presence of trypsin. The hydrophobic and shape complementarity between the peptide substrate P1 sidechain and the enzyme S1 binding cavity accounts for the substrate specificity of this enzyme. Chymotrypsin may also hydrolyze other amide bonds in peptides at slower rates, particularly those containing leucine and methionine at the P1 position. Structurally, it is the archetypal structure for its superfamily, the PA clan of proteases.

Chymotrypsin, a digestive protease, is produced in inactive form as chymotrypsinogen in the pancreas and transported in this form to the stomach where it is activated. This stops the enzyme from digesting the pancreas or other tissues before it enters the gut. This type of inactive precursor to an enzyme is known as a zymogen or proenzyme.

The term "unintended use," as used herein, refers to uses or occurrences unrelated to product design. For example, intentional extraction of residual drug from formulations that are meant to be taken orally for concentration of drug for injection or nasal infusion are all considered unintended use.

The term "Naltrexone," as used herein, refers to a medication (sold under the brand names REVIA and VIVITROL among others) primarily used to manage alcohol dependence and opioid dependence. It may also be called N-Cyclopropyl-methylnoroxymorphone, N-Cyclopropylmethyl-14-hydroxydihydro-morphinone, or 17-(Cyclopropylmethyl)-4, 5α-epoxy-3,14-dihydroxymorphinan-6-one. In opioid dependence, Naltrexone may not be started until people are detoxified. Naltrexone may be taken by mouth or by injection into a muscle. Effects may begin within 30 minutes. A decreased desire for opioids however may take a few weeks. In one embodiment, naltrexone of the present disclosure also includes any chemically modified naltrexone. For example, O-Methoxy naltrexone is naltrexone with a methyl position at the phenolic alcohol. Naltrexone and O-methoxy naltrexone are shown here as example compounds of the opioid class of drugs. Other opioids that are suitable for this invention include but are not limited to: oxycodone, morphine, fentanyl, hydrocodone, tapentadol, methadone, hydromorphone, meperidine, buprenorphine, codeine and naloxone.

The prescription names of them can be found in this link: http://www.rehabcenter.net/list-opioids-united-states/.

Applicants note that naloxone, naltrexone and methadone are opiate antagonists—given to addicts to help block effects of opioids. In the disclosure, Applicants utilized naltrexone as a model system for opioids that cause addiction like oxycodone. Applicants envision that the present disclosure may be applicable to other medicines or drugs.

The term "self-immolative linker," as used herein, refers to any linker molecule which cyclizes upon itself when an enzyme cleaves at the C-terminus of the lysine of the enzyme-responsive peptide-drug complex so that an unmodified drug is released. It is important to include a self-immolative linker in the complex because one does not need to modify a drug for the present invention. Many drugs may be applicable in the present invention and unmodified drugs could be released from a complex according to certain embodiments of the present invention. In one embodiment, the self-immolative linker is a methylaminoethylamine linker. Applicants envision that other self-immolative linker may also be used to release an unmodified drug from the complex of the present invention.

In one embodiment, a drug may be attached covalently to the complex without any self-immolative linker. In another embodiment, a drug may be attached covalently to the complex with one self-immolative linker so that an unmodified drug may be released. Example 9 and Scheme 9 (FIG. 26) show an exemplary self-immolative linker in one non-crushable cross-linked polymer for non-abusable formulation.

In one embodiment, the present disclosure reveals a single or dual-responsive peptide or method of using the peptide for controlled releasing a medication or a drug. In embodiment, the medication or a drug is from the opioid class of compounds.

In one embodiment, the present disclosure reveals a single or dual-responsive peptide or method of using the peptide for controlled releasing a drug such as opioid to prevent abuse of the drug.

The term "PDMS," as used herein, refers to polydimethylsiloxane.

The term "PEG," as used herein, refers to polyethylene glycol.

The term "Fmoc," as used herein, refers to fluorenylmethyloxycarbonyl.

The term "DIPEA," as used herein, refers to N,N-diisopropylethylamine.

The term "DMF," as used herein, refers to dimethylformamide.

The term "TFA," as used herein, refers to trifluoroacetic acid.

The term "DCM," as used herein, refers to dichloromethane.

The term "ESI-MS," as used herein, refers to electrospray ionization-mass spectrometry.

The term "HBTU," as used herein, refers to 2-(1H-benzotriazol-1-yl)-1,1,3,3-tetramethyluronium hexafluorophosphate.

The term "HPLC," as used herein, refers to high-performance liquid chromatography.

The term "DME," as used herein, refers to dimethoxyethylene glycol.

The term "MeCN," as used herein, refers to acetonitrile.

The term "DIEA," as used herein, refers to diisopropylethylamine.

The term "TIPS," as used herein, refers to triisopropylsilane.

The term "t-BOC" or "BOC," as used herein, refers to ter-butyloxycarbonyl.

The term "TEA," as used herein, refers to triethylamine.

The term "Ac," as used herein, refers to acetyl.

The term "HOBt," as used herein, refers to 1-hydroxybenzotriazole.

The term "PMVS," as used herein, refers to poly(methylvinylsiloxane).

The term "PVD2," as used herein, refers to polysiloxane with a vinyl group every three siloxane repeat units.

The term "HEPES," as used herein, refers to 4-(2-Hydroxyethyl)piperazine-1-ethanesulfonic acid.

The term "DMSO," as used herein, refers to dimethyl sulfoxide.

The term "EDTA," as used herein, refers to ethylenediaminetetraacetic acid.

The term "trityl," as used herein, refers to triphenylmethyl.

The term "TCEP," as used herein, refers to Tris(2-carboxyethyl)phosphine.

The term "KHMDS," as used herein, refers to potassium bis(trimethylsilyl)amide.

The term "OECD," as used herein, refers to Organization for Economic Cooperation and Development.

The term "ALT," as used herein, refers to alanine aminotransferase.

The term "AST," as used herein, refers to aspartate aminotransferase.

The term "BUN," as used herein, refers to blood urea nitrogen.

The term "Creat," as used herein, refers to creatinine.

The term "natural amino acid," as used herein, refers to any one of the 20 amino acids used for protein biosynthesis as well as other amino acids which can be incorporated into proteins during translation (including pyrrolysine and selenocysteine). The 20 natural amino acids include histidine, alanine, valine, glycine, leucine, isoleucine, aspartic acid, glutamic acid, serine, glutamine, asparagine, threonine, arginine, proline, phenylalanine, tyrosine, tryptophan, cysteine, methionine and lysine.

The term "non-natural amino acid," as used herein, refers to an organic compound that is not among those encoded by the standard genetic code, or incorporated into proteins during translation. Therefore, non-natural amino acids may include amino acids or analogs of amino acids, but are not limited to, the D-isostereomers of amino acids, the beta-amino-analogs of amino acids, citrulline, homocitrulline, homoarginine, hydroxyproline, homoproline, ornithine, 4-amino-phenylalanine, cyclohexylalanine, α-aminoisobutyric acid, N-methyl-alanine, N-methyl-glycine, norleucine, N-methyl-glutamic acid, tert-butylglycine, α-aminobutyric acid, tert-butylalanine, 2-aminoisobutyric acid, α-aminoisobutyric acid, 2-aminoindane-2-carboxylic acid, selenomethionine, dehydroalanine, lanthionine, γ-amino butyric acid, and derivatives thereof wherein the amine nitrogen has been mono- or di-alkylated.

The term "lysine," as used herein, refers to an α-amino acid that is used in the biosynthesis of proteins. Lysine may contain an α-amino group (which is in the protonated —$NH_3^+$ form under biological conditions), an α-carboxylic acid group (which is in the deprotonated —COO— form under biological conditions), and a side chain lysyl (($CH_2)_4NH_2$), classifying it as a charged (at physiological pH), aliphatic amino acid. Lysine may be essential in humans, meaning the body cannot synthesize it and thus it must be obtained from the diet.

The term "tamper-resistant," as used herein, encompasses both the ability to physically resist tampering, as well as resist tampering due, at least in part, to a deterrent effect. In one embodiment, the present enzymatically triggered drug release system or noncrushable pill formulations are tamper-resistant. A drug or medicine within the enzymatically triggered drug release system or noncrushable pill formulations would not be released until it reaches the desired location of the subject body. For example, the enzymatically triggered drug release system or noncrushable pill formulation is heat-resistant, acid or base-resistant or resistant to other harsh conditions so that one cannot tamper the system or formulation to release the drug.

The term "peptide," as used herein, encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to, N-terminus modification, C-terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C.A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), a-aza bonds (—NH—N(R)—CO—), wherein R is any alkyl, e.g., methyl, carba bonds (—$CH_2$—NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom. These modifications can occur at any of the bonds along the peptide chain and even at several (2-3) at the same time.

The term "amino acid" or "amino acids," as used herein throughout, is understood to include the 20 naturally occurring amino acids; those amino acids often modified post-translationally in vivo, including, for example, hydroxyproline, phosphoserine and phospho threonine; and other unusual amino acids including, but not limited to, 2-aminoadipic acid, hydroxylysine, isodesmosine, nor-valine, norleucine and ornithine. The term "amino acid" as used herein includes both D- and L-amino acids.

The term "protecting group," as used herein, refers to well-known functional groups which, when bound to a functional group, render the resulting protected functional group inert to the reaction conditions to be conducted on other portions of the compound and which, at the appropriate time, can be reacted to regenerate the original functionality. The identity of the protecting group is not critical and is selected to be compatible with the remainder of the molecule. In one embodiment, the protecting group is an "amino protecting group" which protects the amino functionality of amino acids during the reactions described herein. Examples of conventional amino protecting groups include, for instance, benzyl, acetyl, oxyacetyl, carboxybenzyl (Cbz), Boc, Fmoc, and the like. In another embodiment, the protecting group is a "hydroxy protecting group" which protects the hydroxyl functionality of amino acids. Examples of hydroxyl protecting groups include, for instance, benzyl, p-methoxybenzyl, p-nitrobenzyl, allyl, trityl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, Protective Groups in Organic Synthesis., 2d Ed., 1991, John Wiley & Sons, and McOmie Protective Groups in Organic Chemistry, 1975, Plenum Press.

In one embodiment, the protecting group is a "thiol protecting group" which protects the S—H functionality of the thiols during the reactions described herein. Examples of conventional thiol protecting groups include, for instance, thioether, thioester, disulfide, p-methoxybenzyl (Mob), trityl (Trt), acetamidomethyl (Acm), tert-butyl and triphenylmethyl groups or others.

The term "enzyme responsive peptide" "enzyme sensitive peptide" or "enzyme cleavable peptide," as used herein, refers to a peptide having one or more specific bonds that can be cleaved under an enzyme's digestion. In one embodiment, the bond[s] of enzyme responsive peptide may be cleaved by a protease. In one embodiment, the protease is selected from the group consisting of trypsin, chymotrypsin, papain and caspase 3 or any enzyme found in the stomach or intestine including but not limited to: gastric lipase, pepsin, aminopeptidase, carboxypeptidase, deoxyribonuclease, dipeptidase, elastase, enterokinase, lactase, maltase, pancreatic amylase, pancreatic lipase, sucrase, dextrinase, nucleosidases, phosphatases.

The term "dual-enzyme responsive peptide" or "dual-enzyme cleavable peptide," refers to a peptide having one or more specific bonds that can be cleaved only under a two enzymes' digestion process. In one embodiment, the enzyme is a protease. In one embodiment, the protease is selected from the group consisting of trypsin, chymotrypsin, papain and caspase 3. In one embodiment, the dual enzyme system is selected from the group consisting of trypsin/chymotrypsin, trypsin/papain, and trypsin/caspase 3, or any combination of enzymes found in the stomach or intestine including but not limited to: gastric lipase, pepsin, aminopeptidase, carboxypeptidase, deoxyribonuclease, dipeptidase, elastase, enterokinase, lactase, maltase, pancreatic amylase, pancreatic lipase, sucrase, dextrinase, nucleosidases, phosphatases.

The term "single enzyme-responsive peptide" or "single enzyme-cleavable peptide," as used herein, refers to a peptide having only one specific bond that can be cleaved only by a single enzyme's digestion process. In one embodiment, the single enzyme system is selected from the group consisting of trypsin, chymotrypsin, papain, caspase 3, and any enzyme found in the stomach or intestine including but not limited to: gastric lipase, pepsin, aminopeptidase, carboxypeptidase, chymotrypsin, trypsin, deoxyribonuclease, dipeptidase, elastase, enterokinase, lactase, maltase, pancreatic amylase, pancreatic lipase, sucrase, dextrinase, nucleosidases, and phosphatases.

The term "alkyl," as used herein, refers to both a saturated aliphatic branched or straight-chain monovalent hydrocarbon having the specified number of carbon atoms. Thus, "(C1-C6) alkyl" means a hydrocarbon having from 1-6 carbon atoms in a linear or branched arrangement. Examples of "(C1-C6) alkyl" include, for example, n-propyl, iso-propyl, n-butyl, iso-butyl, sec-butyl, t-butyl, -pentyl, -hexyl, 2-methylbutyl, 2-methylpentyl, 2-ethylbutyl, 3-methylpentyl, and 4-methylpentyl. Alkyl can be optionally substituted with halogen, —OH, oxo, (Ci-C6)alkyl, (C1-C6)alkoxy, (C1-C6) alkoxy(C1-C4)alkyl, aryl, heteroaryl, heterocyclyl, cycloalkyl, carbocyclyl, nitro, cyano, amino, acylamino, or carbamyl, —C(O)O(C1-C6)alkyl, or —C(O)(C1-C6)alkyl.

The term "alkenyl," as used herein, refers to a straight-chain or branched alkyl group having one or more carbon-carbon double bonds. Thus, "(C2-C6) alkenyl" means a hydrocarbon having 2-6 carbon atoms in a linear or branched arrangement having one or more double bonds. Examples of alkenyl groups include, but are not limited to, ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene).

The term "alkynyl," as used herein, refers to a straight-chain or branched alkyl group having one or more carbon-carbon triple bonds. Thus, "(C2-C6) alkynyl" means a hydrocarbon having 2-6 carbon atoms in a linear or branched arrangement having one or more triple bonds. Examples of alkynyl groups include, but are not limited to, ethynyl, propynyl, butynyl, pentynyl, and the like. The one or more carbon-carbon triple bonds can be internal (such as in 2-butyne) or terminal (such as in 1-butyne).

The term "alkoxy", as used herein, refers to an "alkyl-O—" group, wherein alkyl is defined above. Examples of alkoxy group include methoxy or ethoxy groups.

The terms "halogen" or "halo," as used herein, refer to fluorine, chlorine, bromine or iodine.

The term "aryl," as used herein, refers to an aromatic monocyclic or polycyclic (e.g., bicyclic or tricyclic) carbocyclic ring system. Thus, "(C6-C18) aryl" is a 6-18 membered monocylic or polycyclic system. Aryl systems include optionally substituted groups such as phenyl, biphenyl, naphthyl, phenanthryl, anthracenyl, pyrenyl, fluoranthyl or fluorenyl. An aryl can be optionally substituted. Examples of suitable substituents on an aryl include halogen, hydroxyl, (C1-C12) alkyl, (C2-C6) alkenyl, (C2-C6) alkynyl, (Ci-C6) haloalkyl, (C1-C3) alkylamino, (C1-C3) dialkylamino (C1-C6) alkoxy, (C6-C18) aryloxy, (C6-C18) arylamino, (C6-C18) aryl, (C6-C18) haloaryl, (5-12 atom) heteroaryl, —NO2, —CN, —OF3 and oxo.

In some embodiments, a (C6-C18) aryl is phenyl, indenyl, naphthyl, azulenyl, heptalenyl, biphenyl, indacenyl, acenaphthylenyl, fluorenyl, phenalenyl, phenanthrenyl, anthracenyl, cyclopentacyclooctenyl or benzocyclooctenyl. In some embodiments, a (C6-C18) aryl is phenyl, naphthalene, anthracene, 1H-phenalene, tetracene, and pentacene.

The term "heteroaryl," as used herein, refers aromatic groups containing one or more atoms is a heteroatom (O, S, or N). A heteroaryl group can be monocyclic or polycyclic, e.g., a monocyclic heteroaryl ring fused to one or more carbocyclic aromatic groups or other monocyclic heteroaryl groups. The heteroaryl groups of this invention can also include ring systems substituted with one or more oxo moieties. Examples of heteroaryl groups include, but are not limited to, thiophenyl, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl. In other embodiments, a 5-20-membered heteroaryl group is pyridyl, 1-oxo-pyridyl, furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, benzothienyl.

The term "haloalkyl," as used herein, includes an alkyl substituted with one or more F, CI, Br, or I, wherein alkyl is defined above.

The term "haloaryl," as used herein, includes an aryl substituted with one or more F, CI, Br, or I, wherein aryl is defined above.

The term "hetero," as used herein, refers to the replacement of at least one carbon atom member in a ring system with at least one heteroatom selected from N, S, or O.

"Hetero" also refers to the replacement of at least one carbon atom member in an acyclic system. A hetero ring system or a hetero acyclic system may have 1, 2, or 3 carbon atom members replaced by a heteroatom.

The terms "heterocyclyl" or "heterocyclic," as used herein, refer to a saturated or unsaturated group having a single ring or multiple condensed rings, from 1 to 10 carbon atoms and from 1 to 4 heteroatoms selected from nitrogen, sulfur or oxygen. In fused ring systems, one or more of the rings can be aryl or heteroaryl, provided that the point of attachment is at the heterocyclyl. Heterocyclyl can be unsubstituted or substituted in accordance with cycloalkyl.

The term "oxo," as used herein, refers to =O. When an oxo group is a substituent on a carbon atom, they form a carbonyl group (C(O)).

The term "thiol-ene reaction," as used herein, refers to an organic reaction between a thiol monomer and an ene monomer.

The term "ring-opening polymerization" or "ROP," as used herein, refers to a polymerization process in which polymerization proceeds as a result of ring opening of a cyclic compound as a monomer to synthetically yield a polymer.

The term "glass transition temperature" or "Tg," as used herein, refers to the temperature at which the amorphous material changes from a glassy solid state to a rubbery state. This temperature may be measured by standard techniques in the art, such as DSC (Differential Scanning calorimetry), e.g., according to the ASTM D3418-97 standard.

The term "gastrointestinal tract" or "GI tract," as used herein, refers to the entire digestive tract. In one embodiment, the term refers to part of the digestive tract formed by stomach and intestines.

The Invention

Needed in the art are non-crushable pill formulations which can prevent drug abuse.

The present invention discloses compositions or formulations and methods of using them for preventing drug abuse, e.g., preventing one from tampering with commercially available formulations of a medicine or a drug.

The present invention reveals an enzymatically triggered drug release system using a single or dual enzyme-responsive peptide-drug complex conjugated to polymers to hydrogel networks. In one embodiment, the enzymatically triggered drug release system includes a single enzyme-enzyme-responsive peptide-drug complex conjugated to a polymer network such as hydrogel networks. The enzymatically triggered drug release system requires one single enzyme's digestion to release the drug from the complex. In another embodiment, the enzymatically triggered drug release system includes a dual enzyme-enzyme-responsive peptide-drug complex conjugated to a polymer network such as hydrogel networks. The enzymatically triggered drug release system requires two enzyme's digestion to release the drug from the complex. For example, the peptide may first be prepared by masking the trypsin substrate, lysine, at the F-amine with a second enzyme substrate and incorporating a self-immolitive linker at the C-terminus. The peptide may then be conjugated to a drug or a medicine through either a linker such as a carbamate or a thionocarbamate linker.

In addition, the single or dual enzyme responsive peptide-drug complex may further include one or more cysteine moieties that allow for thiol-ene conjugation to a variety of host molecules ranging from polymers to hydrogel networks to form the enzymatically triggered drug release system.

Applicants' co-pending PCT application entitled "Dual enzyme-responsive peptides" includes detailed information of single, multiple or dual enzyme-responsive peptides. For example, the single, multiple or dual enzyme-responsive peptides may include one more free thiols (such as those from cysteine). Applicants not that a dual enzyme-responsive peptide can be used as a single enzyme-responsive peptide when the substrate of the second enzyme is exposed (unmasked). FIG. 11 shows some exemplary dual enzyme-responsive peptides including one or two free thiols. When the single or dual enzyme-responsive peptides include at least two free thiols, the single or dual enzyme-responsive peptides may be used as cross-linkers.

Figure 24:
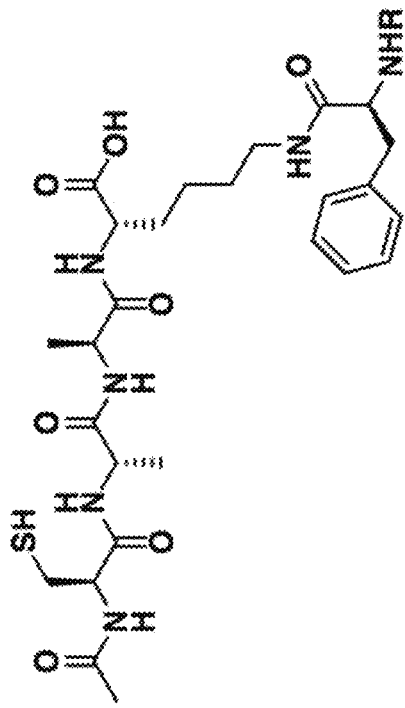
FIG. 24 is a set of chemical formulae showing other exemplary dual enzyme cleavable peptides according to certain embodiments of the present invention.
Figure 25:
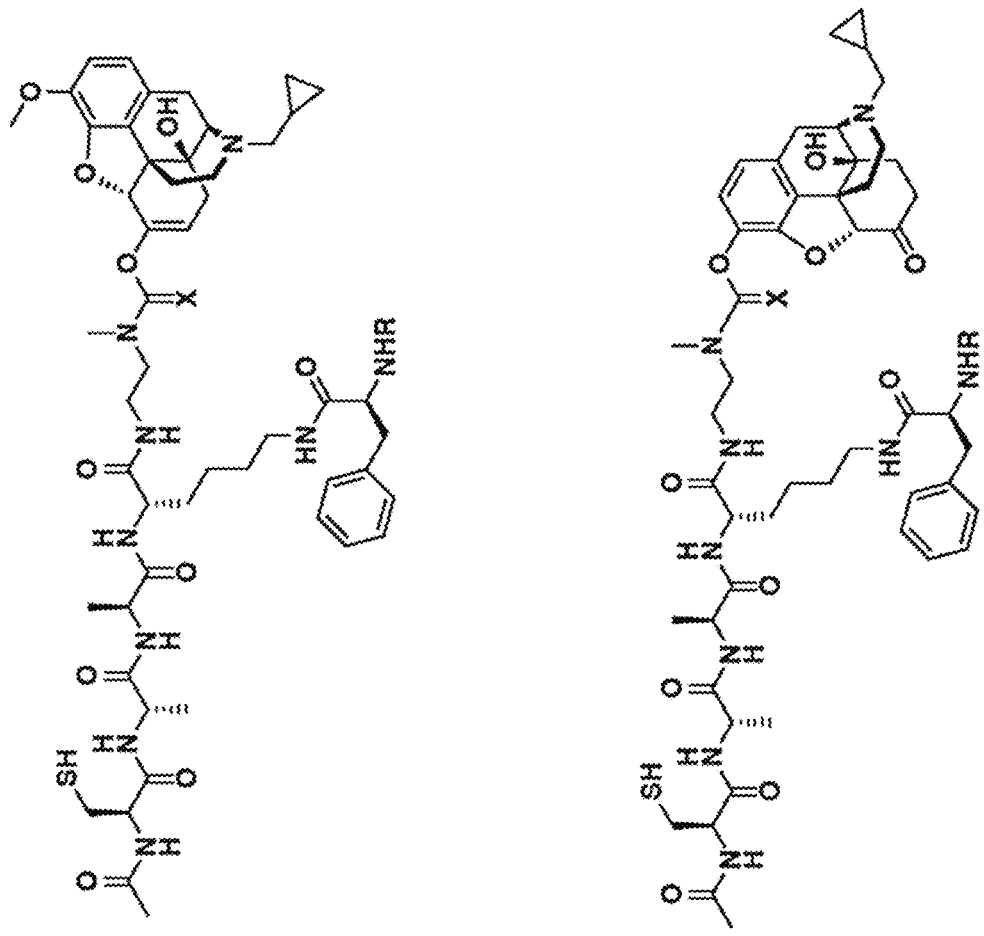
FIG. 25 is a set of chemical formulae showing other exemplary dual enzyme cleavable peptides conjugated to Naltrexone as an exemplary medication according to certain embodiments of the present invention.

FIGS. 24 and 25 show some additional examples of single or dual enzyme-responsive peptides including one free thiol.

For example, Naltrexone may be used as a model drug of the opioid family in conjugation with a dual enzyme-responsive peptide to form a complex, which can be conjugated to a polymer or copolymer such as PDMS (polydimethylsiloxane) copolymer containing 12% vinyl groups to form an enzymatically triggered drug release system. This system may be then crosslinked with a cross linker such as 4-arm polyethylene glycol (PEG) thiol forming a rigid crosslinked network resistive to mechanical stress under a variety of conditions. In one embodiment, the dual enzyme responsive peptide-drug complex may include at least one free linker such as free thiol to bond with a polymer or a copolymer. In another embodiment, the dual enzyme responsive peptide-drug complex may include at least two free linkers such as free thiols to bond with a polymer or a copolymer. Thus, in one embodiment, the dual enzyme responsive peptide-drug complex may be used as a cross-linker to form the enzymatically triggered drug release system.

In one embodiment, a drug or a medicine is covalently bonded with a dual enzyme-responsive peptide to form a complex, which is further conjugated with a polymer or copolymer or trapped in the inner cavities of cross-linked polymer to form the enzymatically triggered drug release system. In one specific embodiment, a single or dual-enzyme responsive peptide is covalently bonded to non-crushable formulation which is comprised of the polysiloxane with 4-arm PEG crosslinker. FIGS. 1-10 and 22 and the Examples include the detailed information of the exemplary enzymatically triggered drug release system.

In another embodiment, a drug or a medicine is not covalently bonded with a dual enzyme-responsive peptide or the enzymatically triggered drug release system. Instead, a drug or a medicine may be held or trapped in the inner cavities of the enzymatically triggered drug release system.

In one embodiment, the present invention relates to digestion of enzymes such as digestive enzymes. In one embodiment, the present invention relates to any enzyme found in the stomach or intestine including, but not limited to: gastric lipase, pepsin, aminopeptidase, carboxypeptidase, chymotrypsin, trypsin, deoxyribonuclease, dipeptidase, elastase, enterokinase, lactase, maltase, pancreatic amylase, pancreatic lipase, sucrase, dextrinase, nucleosidases, phosphatases.

For example, a drug or a medicine may be released from the enzymatically triggered drug release system only after digestion with specific enzymes.

In one embodiment, when a drug or a medicine is covalently bonded with a single enzyme-responsive peptide of the enzymatically triggered drug release system, digestion with one single enzyme is required to cleave the related bond to release the drug or the medicine. In one embodiment, when a drug or a medicine is covalently bonded with a dual enzyme-responsive peptide of the enzymatically triggered drug release system, digestion with enzymes is required to cleave the related bond to release the drug or the medicine. Applicants not that a dual enzyme-responsive peptide can be used as a single enzyme-responsive peptide when the substrate of the second enzyme is exposed (unmasked).

In another embodiment, when a drug or a medicine may be held or trapped in the inner cavities of the enzymatically triggered drug release system, digestion with enzymes is required to cleave the related bond(s) of the inner cavities to release the drug or the medicine.

In one aspect, the present invention discloses compositions or formulations including an enzymatically triggered drug release system and methods of using these compositions or formulations for preventing drug abuse, e.g., preventing one from tampering with commercially available formulations of a medicine or a drug.

In one embodiment, a drug or a medicine in the enzymatically triggered drug release system can only be released when the system is within certain parts of the subject's body, such as the digestive tract. For example, a drug or a medicine in the enzymatically triggered drug release system may only be released when the system is in the presence of digestive enzymes within certain parts of the subject's body.

The present invention discloses a non-crushable pill formulation comprising the enzymatically triggered drug release system for preventing illegal use of a drug or other controlled substance.

In one embodiment, the non-crushable pill formulation comprises a complex of a polymer backbone which forms an elastomer after being interconnected with cross-linkers. The elastomer is in a rubbery state at room temperature. The complex and the pill would not be crushed or liquefied at room temperature.

Further, a drug or other controlled substance may be covalently bonded to or trapped within (without covalently bonding with the complex) the non-crushable elastomers through enzyme responsive peptides as cross-linkers. In the absence of specific enzymes which are necessary for cleaving the peptide bonds of the enzyme responsive peptides, the drug or other control substance could not be released from the complex.

The drug or other control substance within the complex of the non-crushable pill formulation may be enzymatically released in the stomach or intestines for persons who take the pills as intended.

In one embodiment, the complex of the present invention may be used to prevent unintended use of a drug including illegal use of a drug.

In one embodiment, the complex comprises a polymer, the polymer forming a polymer backbone of the complex; cross-linkers, the cross-linkers connecting the polymer backbone through covalently bonding to form at least one inner cavity within the complex; and the drug, wherein the drug is trapped either covalently or non-covalently in at least one inner cavity within the complex, wherein the cross-linkers comprise an enzyme-responsive peptide or non-responsive cross-linker such as PEG, and wherein the drug is prevented from releasing outside of the complex.

In one embodiment, the polymer is selected from the group consisting of glass transition temperature below room temperature (less than 23° C.) such that they are in a rubbery state at room temperature. Examples of polymers with low glass transition temperatures include, but are not limited to, polysiloxanes, polyvinyl fluoride, polypropylene polyethylene, poly-3-hydroxybutyrate, polyoxymethylene, polyvinylidne fluoride, polyesters, and polycarbonates.

In one embodiment, the polymer forms an elastomer. In one embodiment, the polymer has a glass transition temperatures (Tg) lower than 23° C. The polymer has a glass transition temperatures (Tg) lower than 4° C. Preferably, the polymer that forms an elastomer has a glass transition temperature (Tg) lower than standard home freezer temperature of −18° C.

In one preferred embodiment, the elastomer is a polysiloxane. The polysiloxane have their typical glass transition temperatures (Tg) between −140° C. and −20° C., preferably between −140° C. and −70° C.). These polysiloxanes may be used as the polymer backbone of the complex according to some embodiments of the present invention.

In one embodiment, a drug is non-covalently encapsulated in the at least one inner cavity within the complex by a cross-linked elastomeric network. In another embodiment, the drug is covalently bonded with the cross-linked elastomeric complex, e.g., with covalent linkage to the polymer backbone or cross-linker. In one specific embodiment, a drug or medicine is covalently bound to the polymer backbone via a single or dual enzyme-responsive peptide linker and/or the cross-linker is not peptide but rather PEG. In another specific embodiment, a drug or medicine is covalently bound to the polymer backbone via a single or dual enzyme-responsive peptide linker and the cross-linker is not the single or dual enzyme-responsive peptide but rather another cross-linker such as PEG with dithiols.

In one embodiment, the polysiloxane backbones may be produced through anionic ring opening polymerization containing vinyl siloxane groups for cross-linking using known methods. The Examples show detail methods of making polysiloxane backbones. Applicants envision that many functional groups other than vinyl siloxane may be used for the present invention. Thus, this invention covers any functional group pendant from the backbone that can cross-link with the peptide by another functional group.

In one embodiment, the polysiloxane backbones may be interconnected by cross-linkers to form the complex. In one embodiment, the cross-linkers may comprise an enzyme-responsive peptide. For example, the cross-linkers may comprise a single or a dual enzyme-responsive peptide. FIGS. 1, 11, 24 and 25 show some examples of single or dual enzyme-responsive peptides.

In one embodiment, the single or dual enzyme-responsive peptide may include at least two thiols. In one embodiment, the single or dual enzyme-responsive peptide may include only two thiols. In another embodiment, the single or dual enzyme-responsive peptide may include at least one thiol. In one embodiment, the single or dual enzyme-responsive peptide may include only one thiol.

Example 10 demonstrates the use of a dual enzyme-responsive peptide with one free thiol in one polysiloxane-based cross-linked elastomeric network to prevent abuse of one exemplary drug, Naltrexone.

In one embodiment, the cross-linkers may comprise other known linkers such as those in thiol-ene chemistry, those in click chemistry, those in oxime chemistry, those in alkyne/azide chemistry, those in supramolecular chemistry and others.

In another embodiment, the cross-linkers may comprise other known linkers such as polymer dithiols including PEG dithiols or polymer multithiols including 4-arm star PEG tetrathiol. In one embodiment, the cross-linkers may comprise both an enzyme-responsive peptide and a PEG dithiol.

In one embodiment, the enzyme-responsive peptide may include at least one free thiol group. In another embodiment, the enzyme-responsive peptide may include two free thiol groups at two ends of the enzyme-responsive peptide. In one embodiment, the two free thiol groups do not have to be at the two ends of the enzyme-responsive peptide. The two free thiol groups may be anywhere along the chain so long as when the peptide is cleaved, the cross-link is broken.

In one embodiment, the enzyme-responsive peptide is a dual enzyme-responsive peptide. Applicants' co-pending PCT application entitled "dual-enzyme responsive peptides" includes detailed information of single, multiple or dual-enzyme responsive peptides. For example, the single, multiple or dual-enzyme responsive peptides may include one or more free thiols (such as those from cysteine).

In one specific embodiment, a dual enzyme-responsive peptide may comprise an amino acid having an α-amino group, an α-carboxylic acid group and an ε-amine group, wherein the α-amino group is covalently bonded with a second amino acid or a peptide, and the α-carboxylic acid is covalently bonded with a first group.

In one embodiment, the ε-amine is a free amine.

In one embodiment, the ε-amine group of the dual enzyme-responsive peptide may be further covalently bonded with a second group. In one embodiment, the second group is an enzyme substrate, such as a protease substrate. In one embodiment, the enzyme substrate is a protease substrate cleavable under digestion of an enzyme of chymotrypsin or other enzyme found in the stomach or intestine.

In one specific embodiment, the second group is an amino acid having a hydrophobic functional group. For example, the second group may be a tyrosine, a tryptophan, or a phenylalanine. In one embodiment, the second group is a phenylalanine.

In one embodiment, the amino acid within the dual enzyme-responsive peptide is a lysine.

In one embodiment, the second amino acid or the peptide comprises a free thiol group. In one embodiment, the peptide comprises a cysteine. Optionally, the first group of the dual enzyme-responsive peptide may also comprise a cysteine. Thus, the dual-enzyme responsive peptide may include two free thiol groups. Example 7 and FIG. 11 show some examples of the single or dual enzyme-responsive peptides with two free thiols as cross-linkers.

In another embodiment, the first group may comprise a drug or a medicine where the drug or the medicine is covalently bonded with the single or dual enzyme-responsive peptide. As such, the single or dual enzyme-responsive peptide may comprise only one free thiol. Example 7 and FIG. 11 show some examples of the single or dual enzyme-responsive peptides with one free thiol.

In one embodiment, the at least one inner cavity within the complex holds the drug in the complex and the drug is covalently attached to the cavity via an enzyme responsive peptide. In one embodiment, when the drug is not covalently bonded to an enzyme responsive peptide, at least one inner cavity within the complex holds the drug in the complex.

A dual enzyme-responsive peptide requires the digestion of two enzymes to cleave the bond between the α-carboxylic acid and the first group, thus releasing the drug. Alternatively, the dual enzyme-responsive peptide may requires the digestion of two enzymes to cleave the bond between the α-amino group and the second amino acid or the peptide to release a target active ingredient. For example, two enzymes selected from the enzyme pair group of trypsin/chymotrypsin or any two enzymes found in the stomach and intestine including, but not limited to, gastric lipase, pepsin, aminopeptidase, carboxypeptidase, chymotrypsin, trypsin, deoxyribonuclease, dipeptidase, elastase, enterokinase, lactase, maltase, pancreatic amylase, pancreatic lipase, sucrase, dextrinase, nucleosidases, phosphatases are necessary to release the drug from the complex.

In one embodiment, the enzyme responsive peptide is a single enzyme-responsive peptide. A single enzyme-responsive peptide requires only one enzyme to cleave the bond between the α-carboxylic acid and the first group to release the drug from the complex. Alternatively, a single enzyme-responsive peptide may require the digestion of one enzyme to cleave the bond between the α-amino group and the second amino acid or the peptide to release a target active ingredient.

For example, similar to the dual enzyme-responsive peptide, a single enzyme-responsive peptide may comprise an amino acid of lysine having an α-amino group, an α-carboxylic acid group and a free ε-amine group, wherein the α-amino group is covalently bonded with a second amino acid or a peptide, and the α-carboxylic acid is covalently bonded with a first group.

The single enzyme-responsive peptide may comprise two free thiol groups at the ends of the peptide to constitute a cross linker. For example, the plurality of amino acids may comprise a cysteine and the first group may also comprise a cysteine. Example 7 shows some examples of the single enzyme-responsive peptide with two free thiols as a cross-linker.

In one embodiment, the single enzyme-responsive peptide may comprise two free thiol groups. For example, the plurality of amino acids may comprise a cysteine and the first group may also comprise the drug, not a cysteine. Example 7 and FIG. 11 show some examples of the single-enzyme responsive peptide with one free thiol.

In one embodiment, the single enzyme-responsive peptide of the complex is cleavable under the digestion of an enzyme, such as a protease.

In one embodiment, the single enzyme-responsive peptide of the complex is cleavable under the digestion of an enzyme selected from the group consisting of trypsin, chymotrypsin, gastric lipase, pepsin, aminopeptidase, carboxypeptidase, chymotrypsin, trypsin, deoxyribonuclease, dipeptidase, elastase, enterokinase, lactase, maltase, pancreatic amylase, pancreatic lipase, sucrase, dextrinase, nucleosidases, phosphatasesare, or any enzyme found in the stomach or intestine. Example 7 shows some exemplary structures of single enzyme-responsive peptides which are digestible under either trpsin or chymotrypsin.

In one embodiment, the dual-enzyme responsive peptide of the complex is cleavable under the digestion of at least two enzymes selected from the group consisting of trypsin, chymotrypsin, gastric lipase, pepsin, aminopeptidase, carboxypeptidase, chymotrypsin, trypsin, deoxyribonuclease, dipeptidase, elastase, enterokinase, lactase, maltase, pancreatic amylase, pancreatic lipase, sucrase, dextrinase, nucleosidases, phosphatasesare, or any enzyme found in the stomach or intestine.

In one embodiment, the dual-enzyme responsive peptide of the complex is cleavable under the digestion of two enzymes selected from the group consisting of trypsin, chymotrypsin, gastric lipase, pepsin, aminopeptidase, carboxypeptidase, chymotrypsin, trypsin, deoxyribonuclease, dipeptidase, elastase, enterokinase, lactase, maltase, pancreatic amylase, pancreatic lipase, sucrase, dextrinase, nucleosidases, phosphatasesare, or any enzyme found in the stomach or intestine.

In one specific embodiment, the dual-enzyme responsive peptide of the complex is cleavable under the digestion of two enzymes of trypsin/chymotrypsin. Example 7 and FIGS. 11, 24 and 25 shows some exemplary structures of dual-enzyme responsive peptides which are digestible under trypsin/chymotrypsin.

In one embodiment, an alternative enzyme responsive peptide for the complex comprises an amino acid having an α-amino group, an α-carboxylic acid group and a hydrophobic group, wherein the α-amino group is covalently bonded with a second amino acid or a peptide, and the α-carboxylic acid is covalently bonded with a first group.

In one embodiment, the amino acid is selected from the group consisting of a tyrosine, a tryptophan, and a phenylalanine. In one embodiment, the amino acid is a modified tyrosine, tryptophan or phenylalanine including the amine modified with another amino acid or protecting group. In one embodiment, the amino acid is a modified phenylalanine including the amine modified with another amino acid or protecting group. In one preferred embodiment, the amino acid is a phenylalanine.

In one embodiment, the hydrophobic group is an aromatic group, such as a phenyl or its derivatives, a benzyl or its derivatives, an indole or its derivatives, or others. In one preferred embodiment, the hydrophobic group is a benzyl group.

In one embodiment, the alternative enzyme responsive peptide may comprise two free thiol groups at the ends of the peptide. For example, the peptide comprises a cysteine and the first group comprises a cysteine. Thus, the alternative enzyme responsive peptide with two free thiols may be used as cross-linkers for the complex. Example 7 shows some example of the alternative enzyme responsive peptides with two free thiols as cross-linkers.

In another embodiment, the alternative enzyme responsive peptide may comprise only one free thiol group. For example, the peptide comprises a cysteine and the first group comprises the drug. Example 7 shows some example of the alternative enzyme responsive peptides with one free thiol as cross-linkers.

In one embodiment, the alternative enzyme-responsive peptide is a single enzyme responsive peptide. A single enzyme is necessary to digest the bond between the α-carboxylic acid and the first group. Alternatively, a single enzyme responsive peptide may require the digestion of one enzyme to cleave the bond between the α-amino group and the second amino acid or the peptide to release a target active ingredient.

In one embodiment, the alternative enzyme responsive peptide is cleavable under the digestion of an enzyme selected from the group consisting of trypsin, chymotrypsin, gastric lipase, pepsin, aminopeptidase, carboxypeptidase, chymotrypsin, trypsin, deoxyribonuclease, dipeptidase, elastase, enterokinase, lactase, maltase, pancreatic amylase, pancreatic lipase, sucrase, dextrinase, nucleosidases, phosphatasesare, and any enzyme found in the stomach or intestine. In one specific embodiment, the alternative enzyme responsive peptide is cleavable under the digestion of chymotrypsin.

In one aspect, the present invention discloses compositions or formulations for controlled releasing of an active ingredient. The compositions or formulations comprise the complex having the enzyme responsive peptide as discussed above.

For example, a polymeric formulation for controlled releasing of an active ingredient may comprise at least one of enzyme responsive peptides as cross-linkers for the complex as discussed above.

For example, a polymeric formulation for controlled releasing of an active ingredient may comprise at least one enzyme responsive peptide as a linker between the drug and the complex as described above. In one preferred embodiment, the polymeric formulation for controlled releasing of an active ingredient may include one enzyme responsive peptide covalently cross-linked to the elastomer as a linker between drug and elastomer (e.g., covalently conjugated to the polysiloxane).

In one aspect, the present invention discloses a method for controlled releasing an active ingredient.

For example, one may produce a complex holding an active ingredient within the complex through polymer backbones (which forms an elastomer after being interconnected by cross linkers) and enzyme responsive peptides. Such a complex would not release the active ingredient unless the complex is present at a specific condition (e.g., specific acidic condition in the stomach or intestines of humans). Thus, the active ingredient may be transported through different conditions without being released until it reaches the targeted location of the subject. FIG. 1 and the Example show synthesis and design of siloxane elastomers with drug entrapped or covalently attached using a representative example dual-enzyme responsive peptide as the cross-linker.

In one embodiment, the elastomer backbones of the complex may be produced by using conventional methods. For example, the siloxane-based elastomer backbones can be synthesized via anionic ring opening polymerization containing vinyl siloxane groups for cross-linking. FIG. 1 and Examples show the detail synthesis and characterizations of some siloxane-based elastomer backbones.

In one embodiment, the drug was mixed with the starting materials of the elastomer backbone synthesis so that the drug can be physically trapped or covalently bound inside elastomeric polymer backbones. Applicants envision that the drug may also be added after the formation of the elastomeric polymer backbones according to certain embodiments of the present invention. In one embodiment, a peptide-drug complex may be first mixed with the polysiloxane and then cross-linked with cross-linker such as 4-arm PEG tetrathiol.

The polymer backbones of the complex may be further interconnected by cross-linkers. In one embodiment, the cross linkers may be enzyme responsive peptides, such as those functionalized with cysteine as discussed above. In another embodiment, the cross linkers may be other traditional linkers such as PEG dithiols or 4-arm star PEG tetra thiols.

In one embodiment, the elastomer backbones may be covalently cross-linked with either poly(ethylene glycol) (PEG) dithiol or 4-arm star PEG tetra thiols or enzyme degradable peptide sequences with two cysteines in the presence of the drug to result in a highly cross-linked network and the drug is entrapped within the network.

In another embodiment, the elastomer backbones may be covalently cross-linked with both poly(ethylene glycol) (PEG) dithiol and enzyme degradable peptide sequences with two cysteines in the presence of the drug to result in a highly cross-linked network and the drug is entrapped within the network.

In one embodiment, the drug may be physically trapped in the inner cavities of the elastomer backbones of the complex. FIG. 1 shows one example of the drug physically trapped inside of the elastomer backbones of the complex.

In another embodiment, the drug may be covalently attached to the polymer backbone through a peptide degradable linkage of the enzyme responsive peptide during the network formation. FIG. 1 shows one example of the drug covalently bonded with the enzyme responsive peptide of the complex.

In one embodiment, the elastomer backbones may be covalently cross-linked with both poly(ethylene glycol) (PEG) dithiol or 4-arm star PEG tetra thiol and/or enzyme degradable peptide sequences with two cysteines through conventional synthetic methods (such as a thiol-ene reaction). In one embodiment, poly(ethylene glycol) (PEG) dithiol or 4-arm star PEG tetra thiol may be used as the only cross-linkers.

In one embodiment, any of the cysteine-functionalized enzyme-responsive peptides as discussed above may be incorporated into the interconnected network of the complex during the crossing-linking process.

In one embodiment, any of the cysteine-functionalized enzyme-responsive peptides as discussed above may be first covalently bonded to the polymer and then the complex formed by the cross-linking process. In one specific embodiment, Applicants bind the drug peptide to the polysiloxane first and then subject that complex to the 4-arm PEG for cross-linking As such, many types of enzyme-responsive peptides with cysteine functionalization may be incorporated into the complex. Example 7 and FIGS. 11, 24 and 25 show some examples of dual or single enzyme-responsive peptides.

Further, these enzyme responsive peptides can act as a second layer of protection to prevent leaching of the drug such as an opioid. Thus, the complex may be used as a system to allow for controlled release of the drug under specifically designed conditions.

For example, when dual-enzyme responsive peptides are used, two different enzymes are required to release the drug from the complex. By modifying the enzyme responsive peptides, different enzymes may be needed to release the drug.

When a single-enzyme responsive peptide is used in the complex, only one single enzyme is necessary to release the drug.

By specifically designing the structures of enzyme responsive peptides, specific enzymes or combination of enzymes may be required to release the drug from the complex.

Further, a non-crushable elastomer is used as the backbone of the complex to prohibit a person from obtaining the drug from the complex by crushing the backbone. A drug in one non-crushable formulation can only be released when it reaches the targeted location of the subject.

For example, the siloxane elastomeric polymer backbones have a Tg of less than $-25°$ C. Applicants note that these types of polymers are already widely used in food products, cosmetics, and implants. Thus, they are bio-compatible.

Further, the elastomeric nature of the polymers chosen in the complex prevents the pill or the drug from being crushable at room temperature, upon heating the materials in the microwave, or upon cooling in home refrigerators and freezers. As such, the protection of the complex on the drug is not easily compromised by heat treatment, freezing treatment, shaving down with a razor, or other techniques often used by abusers to obtain a powder for nasal inhalation.

Even further, the protection of enzyme responsive peptides on the drug allows the complex to survive conventional extraction methods by the abuser such as those using aqueous or acidic solutions, like vinegar or lemon juice or, potentially, cola. The drug will be entrapped physically or covalently in an elastomeric network that is only selectively degraded in the presence of one or two specific enzymes.

In one specific embodiment, the present method provides a two-step safety system, combining physical barriers with enzyme degradation technology.

In one embodiment, the present complex with elastomer backbones and enzyme responsive peptide cross-linkers could be orally ingested to release the drug since the polymers will degrade in the presence of digestive enzymes.

Specifically, the complex with specifically designed enzyme responsive peptide cross-linkers would allow the drug to be released only in certain locations within the body of a subject, such as the stomach/intestines of a subject. As such, the present invention provides a system for preventing the unintended use of a drug.

In one embodiment, the present invention provides a tamper-resistant system or formulation for a drug or medicine. As discussed above, a drug or medicine within the enzymatically triggered drug release system or noncrushable pill formulations would not be released until it reaches the desired location of the subject body. In one embodiment, the enzymatically triggered drug release system or noncrushable pill formulation is heat-resistant, acid or base-resistant or resistant to other harsh conditions so that one cannot tamper the system or formulation to unintendedly release the drug.

The example as shown above uses a thiol-ene chemistry for cross-linking. Applicants envision that the present invention is also applicable to other chemistries of cross-linking such as click chemistry, oxime chemistry, alkyne/azide chemistry, supramolecular chemistry and others.

Applicants envision that the complex in the present invention may be combined with any other pharmaceutical formulations.

For example, a composition including the complex may further comprise a carrier, a diluent or filler, a binder, a sweetener, a flavoring agent, a solvent, a lubricant, or any other components suitable for a pharmaceutical formulation.

For example, the formulation and composition including the complex may further comprise a pharmaceutically acceptable solid or liquid filler, diluent or encapsulating material, pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials.

The formulation and composition including the complex may further comprise stabilization agents that stabilize the peptides or formulations. The formulation or the composition may be either in solid form or in liquid form.

The formulation or the composition may further comprise any additive that may also impart significant physical stability to dry, e.g., lyophilized peptides.

Various additional preparative components and methods, as well as specific formulation additives, are provided herein which yield formulations for peptides, wherein the peptide is stabilized in a substantially pure, unaggregated form using a solubilization agent. A range of components and additives are contemplated for use within these methods and formulations. Exemplary of these solubilization agents are cyclodextrins (CDs), which selectively bind hydrophobic side chains of polypeptides. These CDs have been found to bind to hydrophobic patches of proteins in a manner that significantly inhibits aggregation. This inhibition is selective with respect to both the CD and the protein involved. Such selective inhibition of peptide aggregation may provide additional advantages within the intranasal delivery methods and compositions of the invention.

EXAMPLES

Representative Peptide Synthesis:

Standard solid phase peptide synthesis conditions were used to synthesize the peptide cross-linker. 2-chlorotrityl chloride resin was loaded with Fmoc-Cysteine(Trityl) in the presence of a mild base, such as TEA. Fmoc-Lysine(Boc), Fmoc-Alanine, Fmoc-Alanine, and Fmoc-Cysteine(Trityl) were subsequently coupled to the loaded resin, and the amine terminus was acetylated prior to cleavage from the resin with TFA in DCM. 20% 4-methylpiperidine in dimethylformamide was used from Fmoc deprotection after each coupling step. The lysine side chain was modified by adding three equivalents Boc-Phe-4-nitrophenylester in the presence of three equivalents of a mild base, triethylamine and purified by precipitation into methanol. Subsequent Boc and Trityl deprotection was carried out using 2.5% TIPS, 2.5% water in trifluoroacetic acid (TFA), and the resulting peptide, generated as a TFA salt, was purified by precipitating into diethyl ether. Reverse phase HPLC was used to purify the peptide if precipitation did not remove all impurities. Expected [M+1]: 684.28 Da Observed [M+1]: 684.2968 Da Representative Dual Enzyme Assay:

Stock solutions of enzymes were prepared by dissolving trypsin (60 mg/ml) in 1 mM HCl and chymotrypsin (60 mg/ml) in pH 7.4 0.035M HEPES+0.1M NaCl.

The elastomer containing polysiloxane+dual-enzyme responsive cross-linker was placed in solution containing equal volumes trypsin and chymotrypsin solutions.

At pre-determined time points, the elastomer was removed from the enzyme solutions and non-crushable properties were evaluated. To determine release of physically entrapped drug compounds, enzyme solutions were analyzed via UV-Vis at pre-determined time points and resulting absorbance values were compared to a standard curve of drug compound in solution to quantitate drug release. Alternatively, release of drug compounds from elastomers was monitored via HPLC at pre-determined time points and again compared to a standard curve of drug compound in solution.

Example 1

Background

Abuse of opioid analgesic alkaloids such as oxycodone is a major societal problem. It is estimated that nearly a third of people who abuse drugs started with prescription medicines, 2.4 million Americans used prescription drugs recreationally in 2010 and 15,000 people in the U.S. alone died in 2009 because of overdose from prescription pain relievers; many more burdened hospitals and medical facilities.[1,2] Misuse of drugs like oxycodone is carried out by crushing the pills for immediate burst release, typically by nasal insufflation, or by liquefying the pills for intravenous injection. In both cases the immediate dosage is higher, causing euphoria, which perpetuates abuse. Thus, there is a strong impetus to develop formulations that prevent and deter misuse. For example, the U.S. Food and Drug Administration has made preventing abuse a priority, the Centers for Disease Control and Prevention have determined that prescription drug abuse is an epidemic, and the Obama administration released a Prescription Drug Abuse Prevention Plan in 2011.[2] Despite strong efforts, abusers have found ways around new non-crushable and non-dissolvable pills by dissolving in solutions found in the home or subjecting the pills to extreme temperatures in microwaves to melt the materials. We disclose in this invention a method to prevent abuse of drugs such as oxycodone, a commonly prescribed opioid, through the use of a non-crushable and non-dissolvable elastomeric polymer formulation. Oxycodone will be physically trapped or covalently bound inside elastomeric polymer micro particles too large to syringe via linkages that can only be degraded by enzymes in the stomach or intestine. We anticipate that the drug delivery vehicles described herein could replace current formulations for these patients since the drug itself is the same, and superior to current formulations in preventing misuse of the product.

Proposed Product/Solution

The disclosed invention should prevent unintended use of prescription drugs in two novel ways: (1) Pills will be formulated from elastomers that will not be able to be crushed or liquefied because they will be in a rubbery state at room temperature; unlike current formulations they will be non-crushable even when heated in the microwave or cooled. (2) Opioids will be covalently conjugated to or entrapped within the non-crushable elastomers via enzyme sensitive peptides, which acts as a second layer of protection to prevent leaching of the opioid. In both cases the drug would be enzymatically released in the stomach or intestines for persons who take the pills as intended.

Specifically, elastomers with low glass transition temperatures ($T_g$) such as those derived from polysiloxane (typically between −140° C. and −70° C.) are used for the polymer backbone. These low $T_g$ values make it so that it will be unlikely that addicts could freeze and then crush the formulation since standard home freezers are −18° C. These types of polymers are already widely used in food products, cosmetics, and implants.[3-6] The siloxane-based polymers are synthesized via anionic ring opening polymerization containing vinyl silane groups for cross-linking using reported methods. These polymers are covalently cross-linked with either poly(ethylene glycol) (PEG) dithiol, 4-arm star PEG tetra thiol, and/or enzyme degradable peptide sequences with two cysteines in the presence of the drug to result in a highly cross-linked network with the drug entrapped (FIG. 1). In addition, the drug can be covalently attached to the polymer backbone through a peptide degradable linkage before, during, or after the network formation (FIG. 1). In both cases, the cross-linking should occur by thiol-ene reaction between the vinyl group and the thiols. This modular cross-linking approach allows for the incorporation of cysteine-functionalized peptides, the sequences of which can be modified to install enzyme sensitivity to a wide range of enzymes as well as to multiple enzymes at the same time (see FIG. 1 for a representative example which requires two enzymes found in the small intestine to cleave).

Methods of Combating Opioid Abuse

There has been considerable effort on preventing widespread opioid abuse, which has resulted in several FDA approved and commercially available products that incorporate abuse-deterrent technologies (ADTs). Currently, there are three approaches used in the formulation of opioids for abuse prevention, including physical/chemical barriers, release of an antagonist, or release of a repellent. Inclusion of a physical or chemical barrier in the design aids in preventing abuse by averting intranasal consumption through crushing or intravenous delivery by dissolving the drug.[7,8] For example, Purdue Pharma has incorporated physical and chemical barriers in several of their opioid formulations, including OxyContin® OP and Hysingla™ ER. OxyContin OP has a unique formulation that features a non-crushable and non-dissolvable pill for the purpose of preventing abusers from receiving a high from immediate release of the drug. The pill contains oxycodone as well as large molecular weight (4,000 kDa) poly(ethylene glycol) for non-crushable properties.[9,10] Purdue also released a new formulation of hydrocodone, Hysingla™, in November 2014, and this is the first formulation to receive FDA labeling as abuse deterrent. Hysingla uses Resistec technology that renders the pills difficult to crush and forms a gel upon attempts at dissolving.[11,12] Opana, by Endo Pharmaceuticals, and Nucynta, by Ortho-McNeil-Janssen Pharmaceuticals, also use poly(ethylene glycol) as a physical barrier to crushing for formulations of oxymorphone and tapentadol respectively.[13] Despite strong efforts to prevent substance abuse through these designs, abusers have found ways to circumvent the deterrent,[14] such as microwaving the pills to melt them, freezing them, and then shaving them down with a razor. Incorporating elastomeric polymers with a Tg lower than −25° C. as in this invention (below the home freezer temperature) into the backbone would prevent these methods of abuse, while allowing for a truly non-crushable formulation. The polymers proposed all have Tg well below this temperature. And even if the addict could find a way to freeze the pill, the drug is further prevented from being active by enzymatic degradable tethers to the materials.

Another approach to deterring abuse of opioids such as oxycodone is incorporating an antagonist into the design. Two common antagonists to oxycodone are naltrexone and naloxone, which are commonly prescribed in opioid dependence treatments.[15-17] Oxytrex, a formulation by Pain Pharmaceuticals, combines oxycodone with naltrexone in a low dose to help prevent dependence and tolerance of the drug.[18,19] Purdue Pharma also designed a matrix containing varying ratios of oxycodone and naloxone or naltrexone.[20] When administered orally, the antagonists are released significantly slower than oxycodone, allowing for pain relief. However, when the matrix is crushed or tampered with, the antagonist is released immediately, preventing the abuser from obtaining a high. Although antagonists prevent abusers from gaining euphoria, they can have adverse effects such as nausea, seizures, pulmonary edema, irregular pulse for naloxone, and liver damage for naltrexone. Naltrexone could be used as a model drug for the present invention due to its adverse effect. Naloxone also has poor intranasal absorption, so its effects are only noticeable in intravenous or intramuscular administration and does not prevent intranasal abuse as readily.[21] Naltrexone and naloxone have been incorporated into other opioid ADT formulations, and are in FDA approved products such as Suboxone by Reckitt Benckiser, Embeda by Kind Pharmaceuticals, Opana by Endo Pharmaceuticals, and Exalgo by MNK.[22-25] Conjugation of oxycodone to an elastomeric polymer would prevent the need for an antidote and simplify formulation and safety, while still allowing for non-crushable/non-dissolvable properties.

The incorporation of enzyme degradable units can also help prevent substance abuse by preventing extraction of the drugs ex-vivo. Collegium Pharmaceuticals formulated a release design incorporating microparticles coated in polysaccharides or proteins known to be specifically cleaved by enzymes in the colon, small intestine, or stomach. This strategy also incorporates lipophilic counterions to decrease solubility in water making aqueous extraction of the drug from the microparticles difficult.[26] Bio-MD, developed by Signature Therapeutics also uses a peptide coating on opioids that requires the enzyme trypsin in the small intestine for degradation.[27] Enzyme release technologies have the potential to be a large milestone in ADT design by requiring enzymes found specifically in the digestive system for release of oxycodone, which prevents abusers from using typical methods of abuse such as crushing. The formulation should also prevent a high from intravenous administration or nasal ingestion. Our design is distinct from this because the peptides are covalently bound to a non-crushable elastomeric formulation. In addition, the elastomer incorporates peptides in a modular way wherein the peptides typically require two enzymes for drug release, thereby preventing extraction.

Incorporating components that promote undesirable symptoms into formulations has also been a route towards preventing abuse. For instance, compounds that produce irritation upon nasal ingestion and decrease abuse of opioids through excessive oral ingestion have been explored. Acura Pharmaceuticals integrated niacin into their opioid formulations to provide uncomfortable effects if large amounts were ingested.[28] Pfizer also incorporated niacin into their oxycodone formulation, Oxceta/Acurox, but Oxceta was not FDA approved until niacin was removed. In addition, these additional materials could cause problems for legitimate users. The enclosed invention does not require the use of an irritating substance.

Many of the current developments to prevent oxycodone abuse target one area of abuse such crush resistance, nasal ingestion, intravenous administration, extraction, etc. However, the market is lacking options that are truly abuse deterrent in all forms.

Advantages of the Present Invention

Abusers have shown themselves to be extremely resourceful and creative in overcoming abuse-deterrent technology and have strategies to abuse most current market formulations. The proposed technology uniquely combines a variety of abuse-deterrent approaches to remove the possibility of abuse. Unlike the abuse deterrent drugs on the market or in clinical trials, our approach will provide a two-step abuse-deterrent system, combining physical barriers to prevent crushing and dissolution with a unique enzymatic degradation technology. Current abuse deterrent technologies include polymers with a Tg above −25° C., allowing for tampering at low and high temperatures. The siloxane elastomeric polymers include a backbone with a Tg of less than −25° C., which will provide a material not easily compromised by heat treatment, freezing treatment, shaving down with a razor, or other techniques often used by abusers to obtain a powder for nasal inhalation.[29-31] In addition, the materials are cross-linked, meaning they will not melt after heating in a microwave, which is observed for high molecular weight PEG. While many current market technologies incorporate some physical barrier (such as non-crushable and non-dissolvable capsules), they can be easily circumvented. In our technology, the entire material is non-crushable.

Another major drawback to many opioid formulations is that addicts are able to extract oxycodone from the formulation using aqueous or acidic solutions, like vinegar or lemon juice or, potentially, cola. Therefore the second component of our system is an enzyme degradable peptide that will provide an additional layer of safety that will render the entire system extremely difficult to abuse. In our designs, oxycodone is entrapped in an elastomeric network that is selectively degraded in the presence of one or two enzymes. In our second formulation, oxycodone is covalently attached to an elastomeric backbone via enzymatically degradable linkages.

While enzymatically degradable peptide linkages have been used independently by companies such as Pharmaco-Fore Inc, in their prodrug, Bio-MD technology, they do not completely deactivate the drug, thus still allowing abusers to obtain a high as long as dosage is high enough.[32] Our approach of a two-step safety system, combining physical barriers with enzyme degradation technology, should afford a technology that addresses the concerns and pitfalls of each method of abuse independently. Furthermore, the proposed dual-enzyme system is a unique deterrent system.

Example 2

Preparation of Polysiloxane Polymers
Synthesis of PMVS

Scheme 1. Synthesis of PMVS polymer.

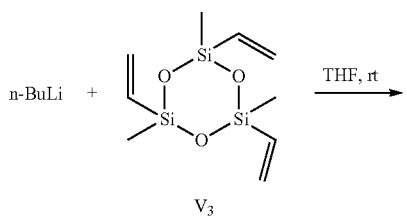

-continued

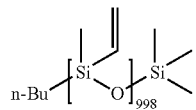

Inside a glove box equipped with inert gas, V3 (2.33 g) monomer was dissolved in 4.66 mL THF. n-BuLi (4.9 µL, 2.5 M in n-hexane) was added as initiator. The solution was stirred at 21° C. The polymerization was monitored. After 2 h, the polymerization was quenched by using chlorotrimethylsilane and the polymer was purified by precipitation in methanol from dichloromethane three times before drying under vacuum to yield PMVS. Number average molecular weight (Mn)=45,000 Da, molecular weight dispersity (Đ)=1.90.

Synthesis of PVD2

Scheme 2. Synthesis of PVD$_2$ Polymer

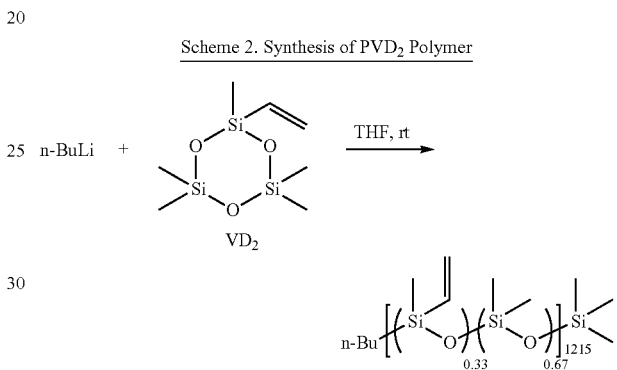

Inside a glove box equipped with inert gas, VD2 (0.5 g) monomer was dissolved in 1.0 mL THF. n-BuLi (9.2 µL, 0.31 M in n-hexane) was added as an initiator. The solution was stirred at 21° C. After 2 h, the polymerization was quenched with chlorotrimethylsilane, and the polymer was purified by precipitating into methanol from dichloromethane three times before drying under vacuum to yield PVD2. Mn=95,000 Da, Đ=1.21.

Synthesis of PMVS0.2-co-PDMS0.8

Scheme 3. Synthesis of PVD2$_{0.2}$-co-PDMS$_{0.8}$ copolymer.

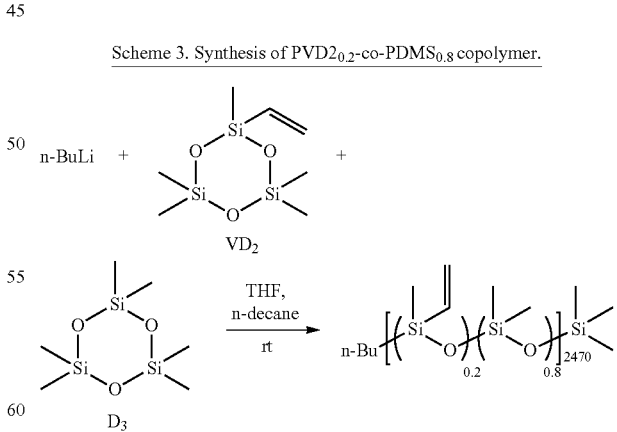

Inside a glove box equipped with inert gas, VD2 (0.1 g) and D3 (0.22 g) monomers were dissolved in 0.96 mL THF. n-Decane (0.1 mL) was added as an internal standard. n-BuLi (2.3 microliter, 0.31 M in n-hexane) was added as an initiator. The solution was allowed to stir at 21° C. and the polymerization was monitored using GC analysis. After 1.15 h, the polymerization was quenched by using chlorotrimethylsilane and the polymer was purified by precipitation in methanol for three times before dried under vacuum to yield PVD2$_{0.2}$-co-PDMS$_{0.8}$. Mn=185,000 Da, Đ=1.05.

Example 3

Preparation of Non-Crushable Elastomers Via Thiol-Ene Cross-Linking

Preparation of Elastomer Using PVD2 with Peptide and PEG Dithiol

Experimental Details

Scheme 4. Preparation of elastomer using PVD$_2$ with peptide and PEG dithiol as dual cross-linkers.

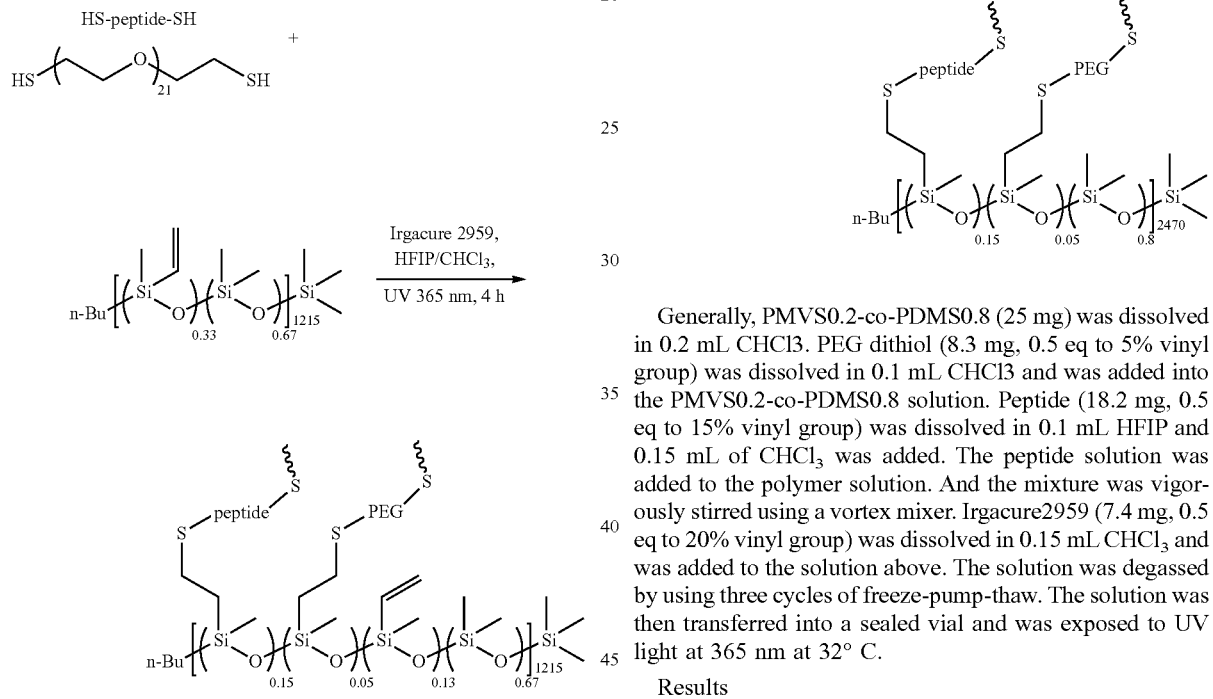

Generally, PVD2 (25 mg) was dissolved in 0.2 mL CHCl3. PEG dithiol (8.3 mg, 0.5 eq to 5% vinyl group) was dissolved in 0.1 mL CHCl3 and was added into the PVD2 solution. Peptide (18.2 mg, 0.5 eq to 15% vinyl group) was dissolved in 0.1 mL HFIP and 0.15 mL of CHCl3 was added. The peptide solution was added to the polymer solution, and the mixture was vigorously stirred using a vortex mixer. Irgacure2959 (7.4 mg, 0.5 eq to 20% vinyl group) was dissolved in 0.15 mL CHCl3 and was added to the solution above. The solution was degassed by using three cycles of freeze-pump-thaw. The solution was then transferred into a sealed vial and was exposed to UV light at 365 nm at 32° C.

Results

Figure 5:
FIG. 5 is a photo showing the picture of elastomer obtained from PMVS with PEG dithiol and peptide (20% cross-linking in total).

A gel was formed after the mixture was exposed to UV light at 365 nm for 4 h (FIG. 5). When the gel was dried by exposing the formulation to air, an elastomer was obtained (FIG. 6A) and showed non-crushable features over a hammer test (FIG. 6B).

Example 4

Preparation of Elastomer Using PMVS0.2-Co-PDMS0.8 with Peptide and PEG Dithiol

Experimental Details

Scheme 5. Preparation of elastomer using PMVS$_{0.2}$-co-PDMS$_{0.8}$ polymer with peptide and PEG dithiol as dual cross-linkers.

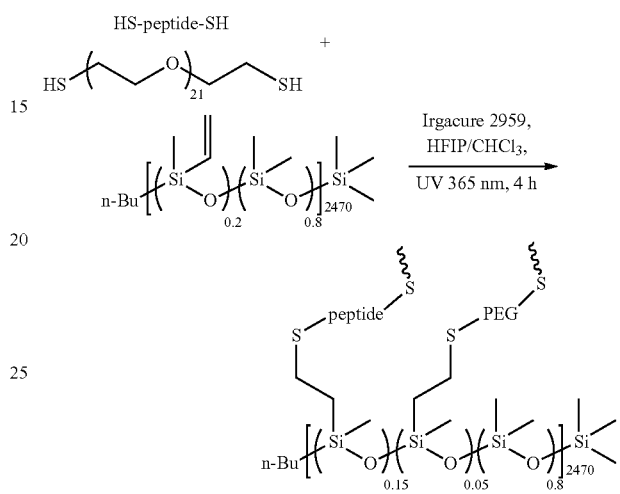

Generally, PMVS0.2-co-PDMS0.8 (25 mg) was dissolved in 0.2 mL CHCl3. PEG dithiol (8.3 mg, 0.5 eq to 5% vinyl group) was dissolved in 0.1 mL CHCl3 and was added into the PMVS0.2-co-PDMS0.8 solution. Peptide (18.2 mg, 0.5 eq to 15% vinyl group) was dissolved in 0.1 mL HFIP and 0.15 mL of CHCl$_3$ was added. The peptide solution was added to the polymer solution. And the mixture was vigorously stirred using a vortex mixer. Irgacure2959 (7.4 mg, 0.5 eq to 20% vinyl group) was dissolved in 0.15 mL CHCl$_3$ and was added to the solution above. The solution was degassed by using three cycles of freeze-pump-thaw. The solution was then transferred into a sealed vial and was exposed to UV light at 365 nm at 32° C.

Results

Figure 7:
FIG. 7 is a photo showing elastomer obtained from PMVS0.2-co-PDMS0.8 with PEG dithiol and peptide (20% cross-linking in total).

A gel was formed after the mixture was exposed to UV light at 365 nm for 4 h (FIG. 7). When the gel was dried by exposing the formulation to air, an elastomer was obtained (FIG. 8A) and showed non-crushable features over a hammer test (FIG. 8B).

Example 5

Preparation of Elastomer Using PMVS with Peptide

Scheme 6. Preparation of elastomer using PMVS with peptide as a cross-linker.

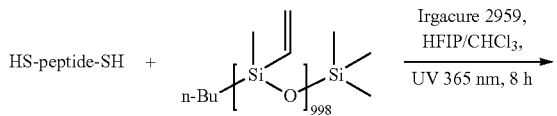

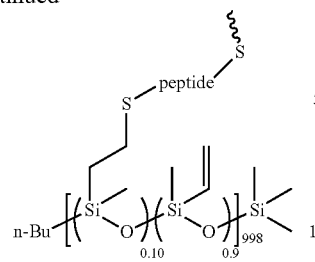

Generally, PMVS (50 mg) was dissolved in 0.3 mL CHCl3. Peptide (21 mg, 0.5 eq to 10% vinyl group) was dissolved in 0.15 mL HFIP and 0.2 mL of CHCl₃ was then added. The peptide solution was added to the polymer solution, and the mixture was vigorously stirred using a vortex mixer. Irgacure2959 (6.5 mg, 0.5 eq to 10% vinyl group) was dissolved in 0.25 mL CHCl₃ and was added to the solution above. The solution was degassed by using three cycles of freeze-pump-thaw. The solution was then transferred into a sealed vial and was exposed to UV light at 365 nm at 32° C.

Results

A gel was formed after the mixture was exposed to UV light at 365 nm for 8 h. When the gel was dried by exposing the formulation to air, an elastomer was obtained (FIG. 9A) and showed non-crushable features over a hammer test (FIG. 9B).

Example 6

Preparation of Drug-Loaded Elastomers Using PMVS with PEG Dithiol

Scheme 7. Preparation of elastomer using PMVS polymer and PEG dithiol with the encapsulation of naltrexone (model drug).

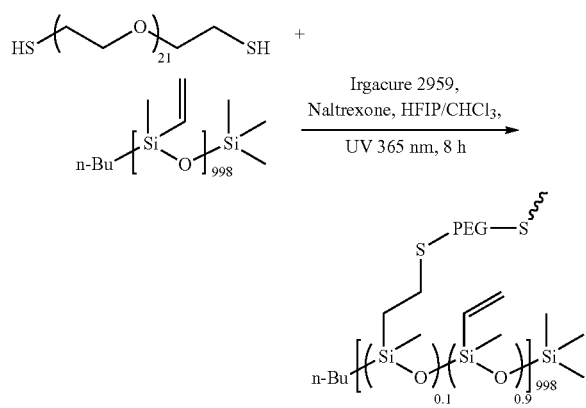

PMVS (50 mg) was dissolved in 0.2 mL chloroform. PEG dithiol (29 mg, 0.5 eq to 10% vinyl group) was dissolved in 0.2 mL THF and was added into the PMVS solution. Naltrexone (8.0 mg) was dissolved in 0.1 mL THF and added to the polymer solution. Irgacure2959 (5.0 mg, 0.5 eq to 20% vinyl group) was added. The mixture was vigorously stirred using a vortex mixer. The solution was degassed by using three cycles of freeze-pump-thaw. The solution was then transferred into a sealed vial and was exposed to UV light at 365 nm at 32° C. for 8 h.

Scheme 8. Preparation of elastomer using PMVS polymer and PEG dithiol cross-linker with the encapsulation of naltrexone HCl (model drug).

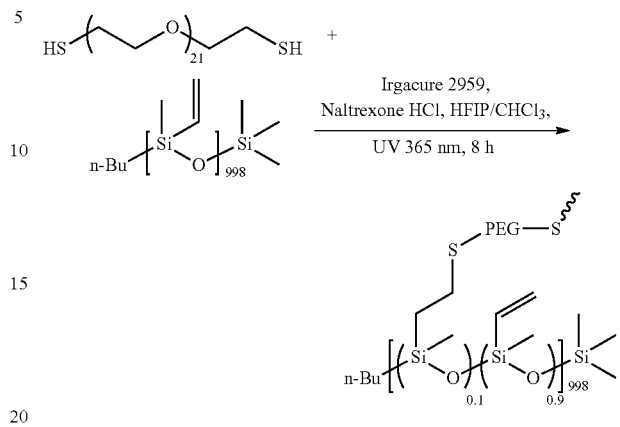

PMVS (50 mg) was dissolved in 0.20 mL chloroform. PEG dithiol (29 mg, 0.5 eq to 10% vinyl group) was dissolved in 0.20 mL THF and was added into the PMVS solution. Naltrexone HCl (8.0 mg) was dissolved in 0.1 mL HFIP and added to the PMVS/PEG dithiol solution. Upon this addition a fine precipitate formed, yet remained suspended in solution. This Naltrexone HCl/PMVS/PEG dithiol solution was added to the Irgacure2959 (5.0 mg, 0.5 eq to 20% vinyl group) initiator. The mixture was vigorously stirred using a vortex mixer. The solution was degassed for three cycles of freeze-pump-thaw. The solution was then transferred into a sealed vial and was exposed to UV light at 365 nm at 32° C. for 8 h.

Results

Elastomers were obtained in both cases: FIG. 10A (naltrexone encapsulated elastomer), FIG. 10B (natrexone HCl encapsulated elastomer)

Example 7

Example Peptides

FIG. 11 shows some exemplary peptides according to one embodiment of the present invention.

Example 8

The disclosed research prevents illegal use of prescription drugs in two novel ways: (1) Pills are formulated from biodegradable elastomers that will not be able to be crushed or liquefied because they are in a rubbery state at room temperature; unlike current formulations they will be non-crushable even when heated in the microwave or cooled. (2) Opioids can be covalently conjugated to or entrapped within the non-crushable elastomers as a second layer of protection to prevent leaching of the opioid. In both cases the drug needs to be enzymatically released in the stomach/intestines for persons who take the pills as intended.

Our model is unique from all other formulations for two reasons. First, the elastomeric nature of the polymers chosen prevents the pill from being crushable at room temperature, upon heating the materials in the microwave, or upon cooling in home refrigerators and freezers. Second, the material is distinct from all other enzymatically degradable opioid delivery systems in that it requires two enzymes found in the stomach or intestines to cleave the peptide linkages. The only enzyme degradable systems currently available for opioid release require one enzyme, typically trypsin. The peptide included in elastomeric systems involving either entrapment of opioid such as oxycodone or covalent attachment of opioid such as oxycodone.

Polysiloxane elastomers are used for the polymer backbone. These types of polymers are already widely used in food products, cosmetics, and implants. Siloxane based polymers are synthesized via anionic ring opening polymerization containing vinyl silane groups for cross-linking using reported methods. These polymers are covalently cross-linked with the dual enzyme degradable peptide in the presence of opioid such as oxycodone to result in a highly cross-linked network with opioid such as oxycodone entrapped. In addition, opioid such as oxycodone can be covalently attached to the polymer backbone through a peptide degradable linkage during the network formation. In both cases, the cross-linking is via thiol-ene reaction.

Polysiloxanes have low glass transitions temperatures (between −140° C. and −70° C. for the polysiloxanes) such that it will be unlikely that addicts could freeze them to enable crushing since standard home freezers are −18° C. Even if addicts could find access to liquid nitrogen, the covalently bound opioid such as oxycodone would not be released except for in the stomach/intenstines. In addition, the crosslinked material will not soften when microwaved: The materials will already be well above the glass transition temperature and further heating will not soften them due to the covalent cross-links.

These elastomeric particles could be orally ingested to release opioid such as oxycodone since the polymers will degrade in the presence of digestive enzymes. In this way, it should only be possible to release the drug in the stomach. The majority of drug formulations can be crushed allowing for illicit use of prescription drugs. We propose that this novel formulation will prevent abuse of drugs by this common method and will be utilized by the legitimate pain patient population. We anticipate that the impact of the drug will be to significantly decrease the generation of new addicts and the ability of current addicts to utilize prescription opioids such as oxycodone drugs. We believe there is significant demand for developing deterrent formulations for opioids such as oxycodone, morphine, fentanyl, hydrocodone, tapentadol, hydromorphone, meperidine, buprenorphine, and codeine, and what is learned in this research could be readily applied these other drugs increasing the market size for the formulation.

Example Experimental for Formation of Cross-Linked Elastomer

Generally, $PVD2_{0.2}$-co-$PDMS_{0.8}$ (25 mg) was dissolved in 0.2 mL $CHCl_3$. PEG dithiol (8.3 mg, 0.5 eq to 5% vinyl group) was dissolved in 0.1 mL $CHCl_3$ and was added into the $PVD2_{0.2}$-co-$PDMS_{0.8}$ solution. Peptide with 2 cysteines (18.2 mg, 0.5 eq to 15% vinyl group) was dissolved in 0.1 mL HFIP and 0.15 mL of CHCl3 was added. The peptide solution was added to the polymer solution. And the mixture was vigorously stirred using a vortex mixer. Irgacure2959 (7.4 mg, 0.5 eq to 20% vinyl group) was dissolved in 0.15 mL and was added to the solution above. The solution was degassed for three cycles of freeze-pump-thaw. The solution was then transferred into a sealed vial and was exposed to UV 365 nm at room temperature.

Results

A gel was formed after the mixture was exposed to UV 365 NM for 4 h. When the gel was dried in the air, an elastomer was obtained and showed non-crushable features over a hammer test. This invention would provide a better opioid abuse deterrent, as the pills would not be able to be crushed for use in a syringe, but would allow the drug to be fully released in the digestive tract of patients.

Abuse of opioid analgesic alkaloids such as oxycodone is a major societal problem. It is estimated that nearly a third of people who abuse drugs started with prescription medicines, 2.4 million Americans used prescription drugs recreationally in 2010 and 15,000 people in the U.S. alone died in 2009 because of overdose from prescription pain relievers; many more burdened hospitals and medical facilities. Thus, there is a strong impetus to develop formulations that prevent and deter misuse. For example, the U.S. Food and Drug Administration has made preventing abuse a priority, the Centers for Disease Control and Prevention have determined that prescription drug abuse is an epidemic, and the Obama administration released a Prescription Drug Abuse Prevention Plan in 2011. We prepared noncrushable and non-dissolvable elastomeric polymers to prevent abuse of opioids such as oxycodone. The oxycodone can be physically trapped or covalently bound inside elastomeric polymer micro particles that are too large to syringe via linkages that can only be degraded by enzymes in the stomach/intestine. The market space in which this product would operate is the legitimate prescription pain relief space: It is estimated that 207 million legally utilize pain medications with a market of $8.5 billion in 2012. The drug delivery vehicles described herein would replace current formulations for these patients since the drug itself is the same, and be superior to current formulations in preventing misuse of the product.

Misuse of drugs like oxycodone is carried out by crushing the pills for immediate burst release, typically by nasal insufflation, or by liquefying the pills for intravenous injection. In both cases the immediate dosage is higher, causing euphoria, which perpetuates abuse. While many pharmaceutical companies are working on or have distributed pills with technologies to prevent opioid abuse, very few of these opioids have an abuse deterrent label approved by the FDA. In addition, despite strong efforts, abusers have found ways around new non-crushable and non-dissolvable pills by dissolving in solutions found in the home or subjecting the pills to extreme temperatures in microwaves to melt the materials. New formulations of these opioids are needed that resist crushing at different temperatures and dissolving in household products. The customers of this invention are the patients that would be prescribed the opioid drugs. It would also serve US hospitals, insurance companies and the government by reducing the financial burden of overdose and drug misuse.

Abusers have shown themselves to be extremely resourceful and creative in overcoming abuse deterrent technology and have strategies to abuse most current market formulations. The proposed technology uniquely combines a variety of abuse-deterrent approaches to remove the possibility of abuse. Unlike the abuse deterrent drugs on the market or in clinical trials, our approach will provide a two-step abuse-deterrent system, combining physical barriers to prevent crushing and dissolution with a unique enzymatic degradation technology. Current abuse deterrent technologies include polymers with a glass transition temperature (Tg) above −25° C., allowing for tampering at low and high temperatures. The siloxane elastomeric polymers include a backbone with love Tg, which will provide a material not easily compromised by heat treatment, freezing treatment, shaving down with a razor, or other techniques often used by abusers to obtain a powder for nasal inhalation. In addition, the materials are cross-linked so unlike materials such as high molecular weight PEG, they will not flow after heating in a microwave. While many current market technologies incorporate some physical barrier (such as non-crushable and non-dissolvable capsules), they can be easily circumvented. In our technology, the entire material is non-crushable. We believe that our abuse-deterrent technology will prevent all current methods used by abusers to obtain a high.

Another major drawback to many opioid formulations is that addicts are able to extract oxycodone using aqueous or acidic solutions, like vinegar or lemon juice or potentially Coca Cola. Therefore the second component of our system is an enzyme degradable peptide that will provide an additional layer of safety that will render the entire system extremely difficult to abuse. In our designs, oxycodone will be entrapped in an elastomeric network that is selectively degraded in the presence of both chymotrypsin and trypsin. Both enzymes are required to cleave the material. In our second formulation, oxycodone will be covalently attached to an elastomeric backbone via enzymatically degradable linkages. In the presence of both enzymes the linkage will be degraded release oxycodone. Thus, addicts could not purchase trypsin or chymotrypsin from the grocery store to degrade the material.

While enzymatically degradable peptide linkages have been used independently by companies such as Pharmaco-Fore Inc, in their prodrug, Bio-MD technology, they do not completely deactivate the drug, thus still allowing abusers to obtain a high as long as dosage is high enough. Our approach of a two-step safety system, combining physical barriers with enzyme degradation technology, should afford a technology that addresses the concerns and pitfalls of each method of abuse independently. Furthermore, the proposed dual-enzyme system is a unique deterrent system.

The market for opioid pain relievers, including oxycodone, has rapidly grown in the past few years. The number of opioid prescriptions has grown from 76 million in 1991 to 207 million in 2013 and sales of opioid pain relievers totaled $8.5 billion in 2012 within the United States alone. Abuse of these analgesics has rapidly increased and is currently a major societal problem. Approximately 15,000 people in the US alone died in 2009 due to overdose of prescription pain reliever and 2.4 million Americans used prescription drugs recreationally in 2010. The total cost of prescription opioid abuse was estimated at $55.7 billion in 2007 and is much higher today. The CDC determined that deaths resulting from opioid abuse have tripled since 1999, and considers prescription substance abuse an epidemic.

Correspondingly, there is considerable interest in developing mechanisms to prevent abuse of opioid analgesics. In 2011, the Obama administration submitted a plan to curb prescription drug abuse, which includes provisions on expediting the development of abuse-deterrent formulations (ADF) of opioid pain relievers. Currently, there are many pharmaceutical firms working on ADFs, with the major players including Purdue Pharma, Pfizer, King Pharmaceuticals, Acura Pharmaceuticals, Collegium Pharmaceutical, and Pain Therapeutics. Despite research into abuse deterrent technologies, opioid abusers have found creative ways to circumvent current ADF approaches. Therefore, there is a need for further development of novel ADF technology.

There has been considerable effort on preventing widespread opioid abuse, which has resulted in several FDA approved, commercially available products that incorporate abuse-deterrent technologies (ADTs). Currently, there are three approaches that are used in the formulation of opioids for abuse prevention including physical/chemical barriers, release of an antagonist, or release of a repellent. Inclusion of a physical or chemical barrier in the design aids in preventing abuse by averting intranasal consumption through crushing or intravenous delivery by dissolving the drug. For example, Purdue Pharma has incorporated physical and chemical barriers in several of their opioid formulations, including OxyContin® OP and Hysingla™ ER. OxyContin OP has a unique formulation that features a non-crushable and non-dissolvable pill for the purpose of preventing abusers from receiving a high from immediate release of the drug. The pill contains oxycodone as well as large molecular weight (4,000 kDa) poly(ethylene glycol) for non-crushable properties. Purdue also released a new formulation of hydrocodone, Hysingla™, in November 2014, and this is the first formulation to receive FDA labeling as abuse deterrent. Hysingla uses Resistec technology that renders the pills difficult to crush and forms a gel upon attempts at dissolving. Opana, by Endo Pharmaceuticals, and Nucynta, by Ortho-McNiell-Janssen Pharmaceuticals, also use poly(ethylene glycol) as a physical barrier to crushing for formulations of oxymorphone and tapentadol respectively. Despite strong efforts to prevent substance abuse through these designs, abusers have found ways to circumvent the deterrent, such as microwaving the pills to melt them, freezing them, and then shaving them down with a razor. Incorporating elastomeric polymers with a glass transition temperature (Tg) lower than −25° C. (below the home freezer temperature) into the backbone would prevent these methods of abuse, while allowing for a truly non-crushable formulation. The polysiloxanes have Tg well below this temperature. And even if the addict could find a way to freeze the pill, the drug is further prevented from being active by enzymatic degradable tethers to the materials.

Another approach to deterring abuse of opioids such as oxycodone is incorporating an antagonist into the design. Two common antagonists to oxycodone are naltrexone and naloxone, which are commonly prescribed in opioid dependence treatments. Oxytrex, a formulation by Pain Pharmaceuticals, combines oxycodone with naltrexone in a low dose to help prevent dependence and tolerance of the drug. Purdue Pharma also designed a matrix containing varying ratios of oxycodone and naloxone or naltrexone. When administered orally, the antagonists are released significantly slower than oxycodone, allowing for pain relief. However, when the matrix is crushed or tampered with, the antagonist is released immediately, preventing the abuser from obtaining a high. Although antagonists prevent abusers from gaining euphoria, they can have adverse effects such as nausea, seizures, pulmonary edema, irregular pulse for naloxone, and liver damage for naltrexone. Naloxone also has poor intranasal absorption, so its effects are only noticeable in intravenous or intramuscular administration and does not prevent intranasal abuse as readily. Naltrexone and naloxone have been incorporated into other opioid ADT formulations, and are in FDA approved products such as Suboxone by Reckitt Benckiser, Embeda by Kind Pharmaceuticals, Opana by Endo Pharmaceuticals, and Exalgo by MNK. Conjugation/incorporation of oxycodone to an elastomeric polymer would prevent the need for an antidote and simplify formulation and safety, while still allowing for non-crushable/non-dissolvable properties.

The incorporation of enzyme degradable units can also help prevent substance abuse by preventing extraction of the drugs ex-vivo. Collegium Pharmaceuticals formulated a release design incorporating microparticles coated in polysaccharides or proteins known to be specifically cleaved by enzymes in the colon, small intestine, or stomach. This strategy also incorporates lipophilic counterions to decrease solubility in water making aqueous extraction of the drug from the microparticles difficult. Bio-MD, developed by Signature Therapeutics also uses a peptide coating on opioids that requires the enzyme trypsin in the small intestine for degradation. Enzyme release technologies have the potential to be a large milestone in ADT design by requiring enzymes found specifically in the digestive system for release of oxycodone, which prevents abusers from using typical methods of abuse such as crushing. The formulation should prevent a high from intravenous administration or nasal ingestion. However, distinct from this technology, our design requires two distinct enzymes to cleave in the stomach and is simultaneously non-crushable.

Incorporating components that promote undesirable symptoms into formulations has also been a route towards preventing abuse. For instance, compounds that produce irritation upon nasal ingestion and decrease abuse of opioids through excessive oral ingestion have been explored. Acura Pharmaceuticals integrated niacin into their opioid formulations to provide uncomfortable effects if large amounts were ingested. Pfizer also incorporated niacin into their oxycodone formulation, Oxceta/Acurox, but Oxceta was not FDA approved until niacin was removed. In addition, these additional materials could cause problems for legitimate users. Our proposed technology would not require the use of an irritating substance.

Many of the current developments to prevent oxycodone abuse target one area of abuse such as crush resistance, nasal ingestion, intravenous administration, extraction, etc. However, the market is lacking options that are truly abuse deterrent in all forms. Our technology addresses all of these areas of abuse with a simple and safe formulation.

Example 9

Noncrushable Cross-Linked Polymer for Non-Abusable Formulations

Figure 26:
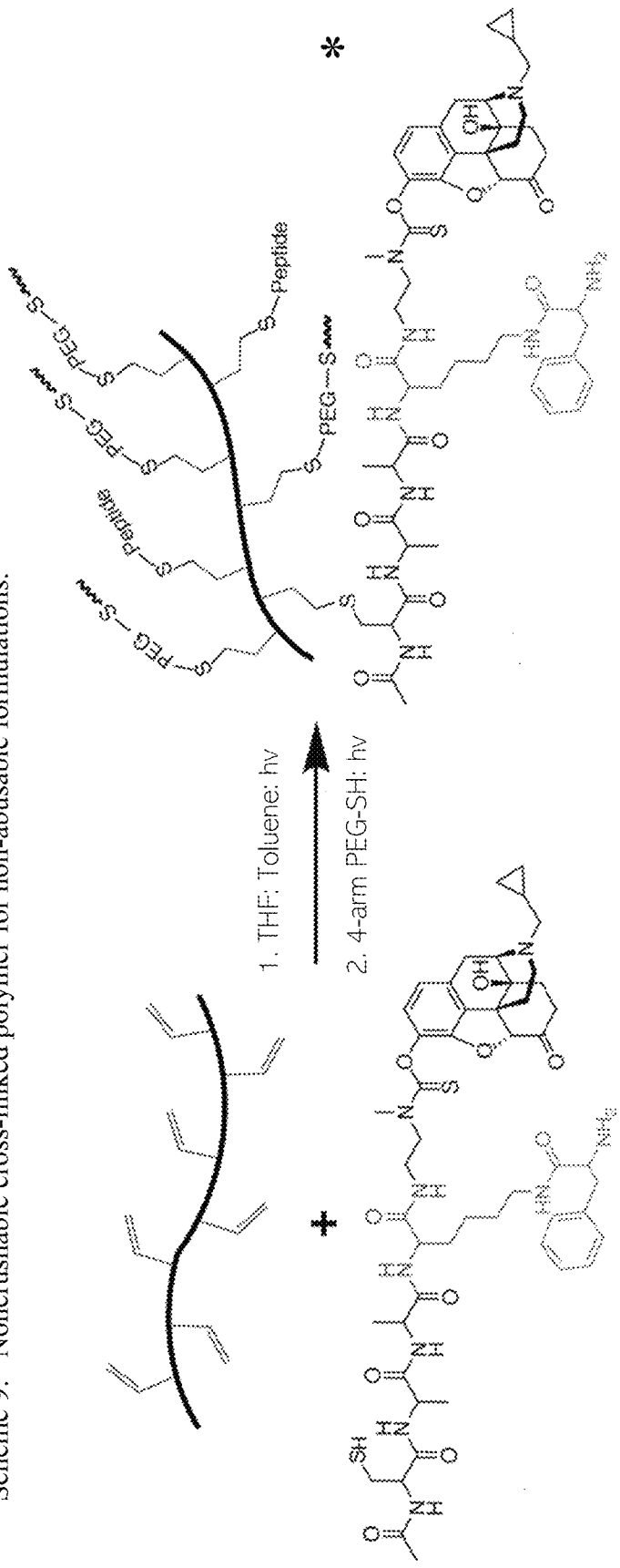
FIG. 26 illustrates a noncrushable cross-linked polymer for non-abusable formulations (Scheme 9). * indicates where FIG. 27 continues.
Figure 26:
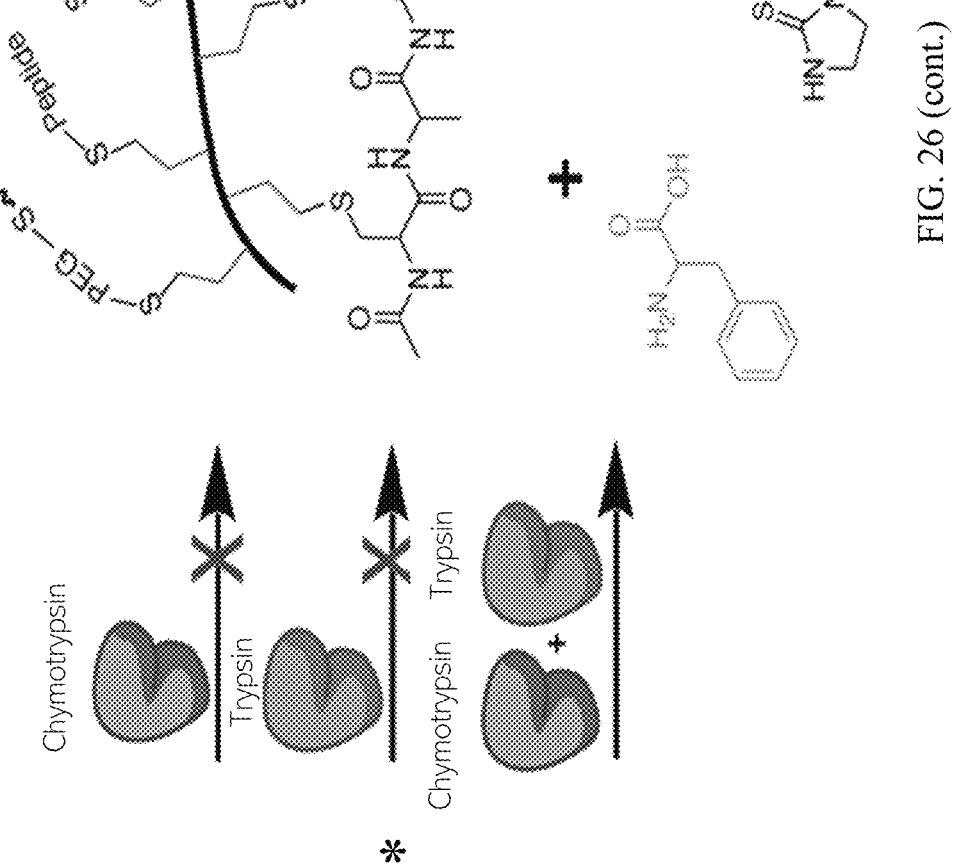

With abuse of prescription opioids so prevalent in society, a need has developed for non-abusable formulations. Many current methods of abuse include tampering with presently available formulations to increase the immediate dose to the user. To this end, we have developed an enzymatically triggered drug release system using a dual enzyme responsive peptide-drug conjugate resistant to "dose-dumping" coupled with a cross-linked polymer to resist crushing for nasal infusion. Specifically, the drug is linked to the noncrushable cross-linked polymer via a peptide linker that can only be cleaved by enzymes found in the small intestine. The peptide was prepared by masking the trypsin substrate, lysine, at the ε-amine with a second enzyme substrate and incorporating a self-immolative linker at the C-terminus. This was then conjugated to the drug through either a carbamate or thionocarbamate linker. The inclusion of a cysteine moiety allows for thiol-ene conjugation to siloxane polymers. As a proof of concept, Naltrexone was used as a model drug of the opioid family, which was conjugated to a polydimethylsiloxane (PDMS) copolymer containing 12% vinyl groups (FIG. 26). This material was then cross-linked with 4-arm polyethylene glycol (PEG-SH) forming a rigid cross-linked network resistive to mechanical stress under a variety of conditions (FIG. 26).

Peptide Synthesis

All peptides were prepared according to the scheme shown below. Peptides were prepared using standard Fmoc (fluorenylmethyloxycarbonyl) solid phase peptide synthesis using a 2-chlorotrityl resin (0.8 mmol/g loading). The N-terminus were acetylated prior to cleavage using 50 eq of acetic anhydride and N,N-diisopropylethylamine (DIPEA) in N,N-dimethylformamide (DMF). The peptides were then cleaved from resin using a 50:50 mixture of trifluoroacetic acid (TFA) and DCM, which maintains the trityl protecting groups while unmasking the ε-amine of the lysine. The peptide was characterized and confirmed utilizing electrospray ionization mass spectrometry (ESI-MS).

Scheme 10. Fmoc solid phase peptide synthesis forming the peptide used in all the following conjugations.

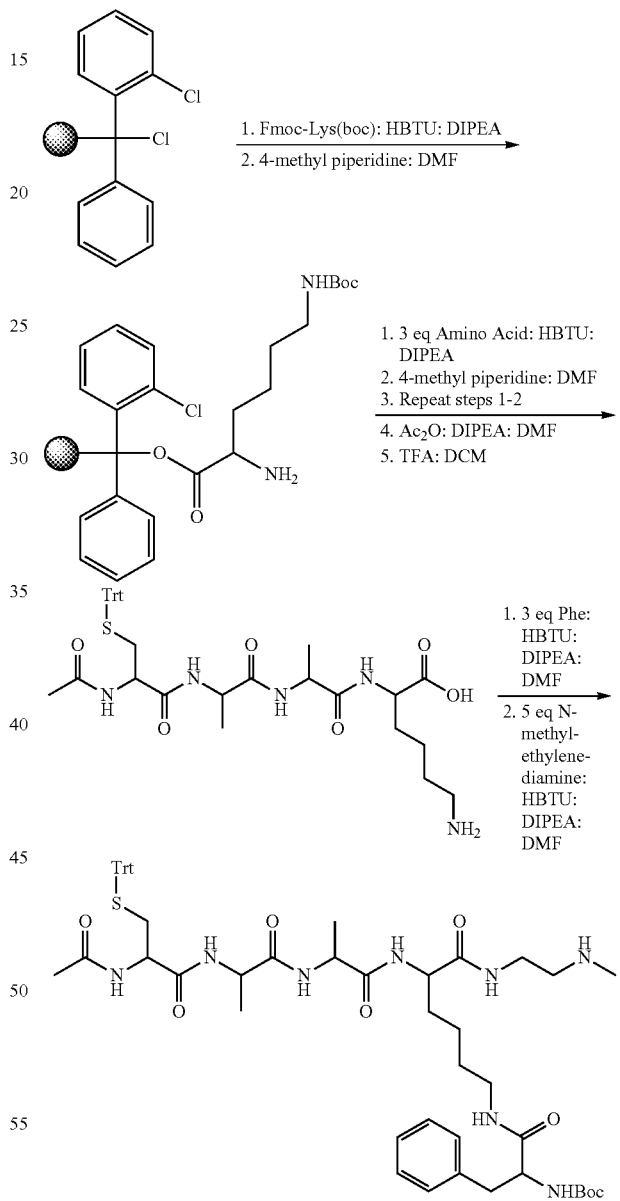

This ε-amine of the lysine was then masked using a solution-phase coupling reaction of the peptide with Boc-Phenylalanine (3 eq), N,N,N'N'-tetramethyl-O-(1-H-benzotriazol-1-yl)uranium hexafluorophosphate (HBTU) (3 eq), and DIPEA (5 eq). This material was then purified using high performance liquid chromatography (HPLC) equipped with a C18 column running a 70/30% to 5/95% H$_2$O/MeCN (acetonitrile) gradient with 0.1% TFA (trifluoroacetic acid)

over 20 minutes with a 5-minute isocratic hold at 95% MeCN (20 mL/min). ESI-MS was used to confirm product identity.

The N-methylethylenediamine was then added to the C-terminus through another solution phase coupling reaction. The peptide was combined with HBTU (1.5 eq) and DIPEA (5 eq) to activate this carboxyl group. The N-methylethylenediamine was then added dropwise (5 eq) to form the desired product shown below. This was purified using HPLC equipped with a C18 column running a 70/30% to 5/95% H₂O/MeCN gradient with 0.1% TFA over 20 minutes with a 5-minute isocratic hold at 95% MeCN (20 mL/min). ESI-MS was used to confirm product identity.

nocarbonate, respectively. This was done using either the free base of Naltrexone or the HCl salt. In a typical procedure, Naltrexone (1 eq), either as the freebase or HCl salt, was dissolved in dry dichloromethane under an Argon atmosphere with magnetic stirring. N,N-diisopropylethylamine (2.5 eq) was then added and stirred for 5 minutes before adding either 4-nitrophenylchloroformate or pentafluorophenyl chlorothionoformate (2 eq) to produce the corresponding carbonate or thionocarbonate, respectively. After 18 hours, the modified Naltrexone product was purified by flash column chromatography using a solvent system of 2-20% acetone in dichloromethane. Typical yields ranged from 83-87% and products were yellow/orange solids. The identities of the desired products were confirmed using 1H NMR, 13C NMR, and ESI-MS.

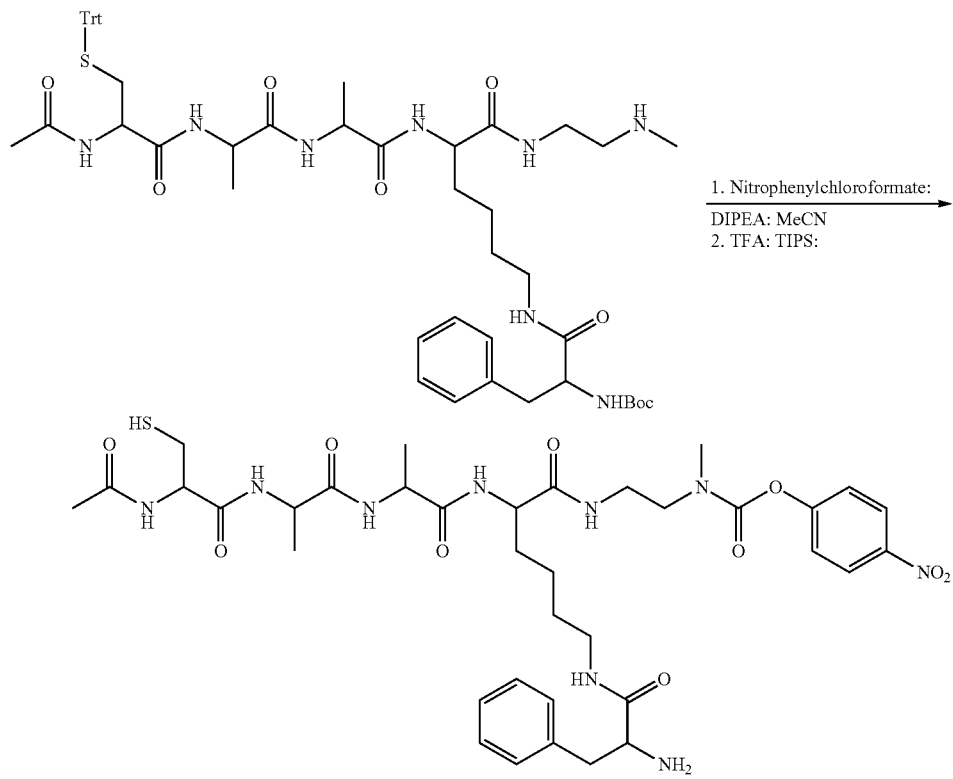

Scheme 11. Conjugation of nitrophenylchloroformate to the diamine C-terminus through a carbamate linker.

The diamine-conjugated peptide could then be attached to a colorimetric compound through a carbamate linker. This material allows for monitoring of enzymatic cleavage through the absorbance at 405 nm. The coupling was carried out in MeCN; followed by purification using HPLC equipped with a C18 column running a 70/30% to 5/95% H2O/MeCN gradient with 0.1% TFA over 18 minutes with a 5-minute isocratic hold at 95% MeCN (3 mL/min). ESI-MS was used to confirm product identity. The material was then deprotected using a solution of 95% TFA, 2.5% TIPS (triisopropylsilane), and 2.5% H₂O. The solution was then concentrated under vacuum and precipitated into cold ether to yield the deprotected peptide. ESI-MS was confirmed the product identity.

Preparation of Modified Naltrexone and Conjugation of Naltrexone to Peptide

The phenol of Naltrexone was modified using either 4-nitrophenylchloroformate or pentafluorophenyl chlorothionoformate to produce the corresponding carbonate or thio- Scheme 12. Synthesis of Naltrexone O-pentafluorophenyl carbonothioate (top) and Naltrexone 4-nitrophenyl carbonate (bottom).

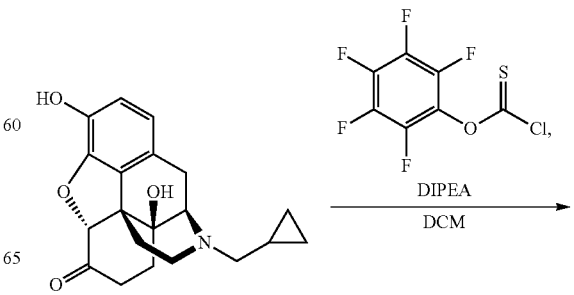

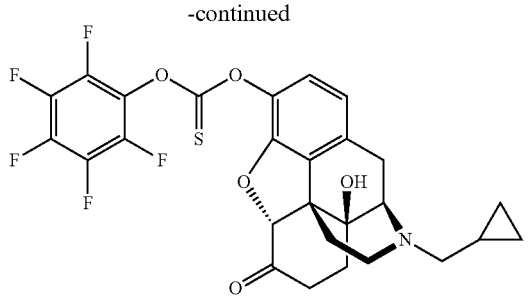

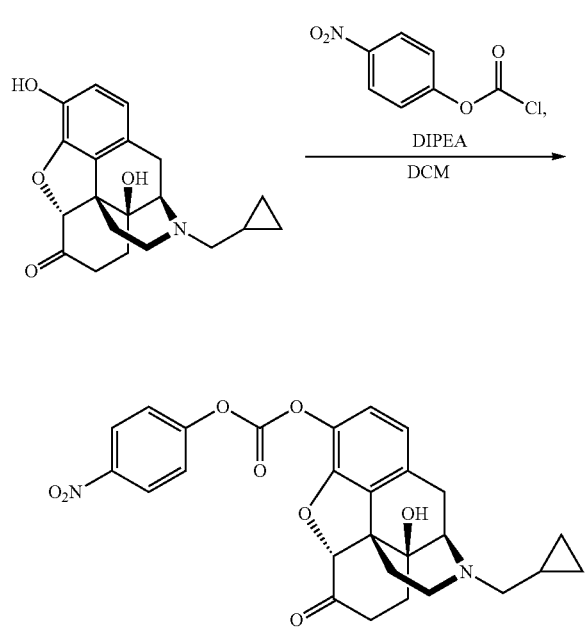

Figure 27:
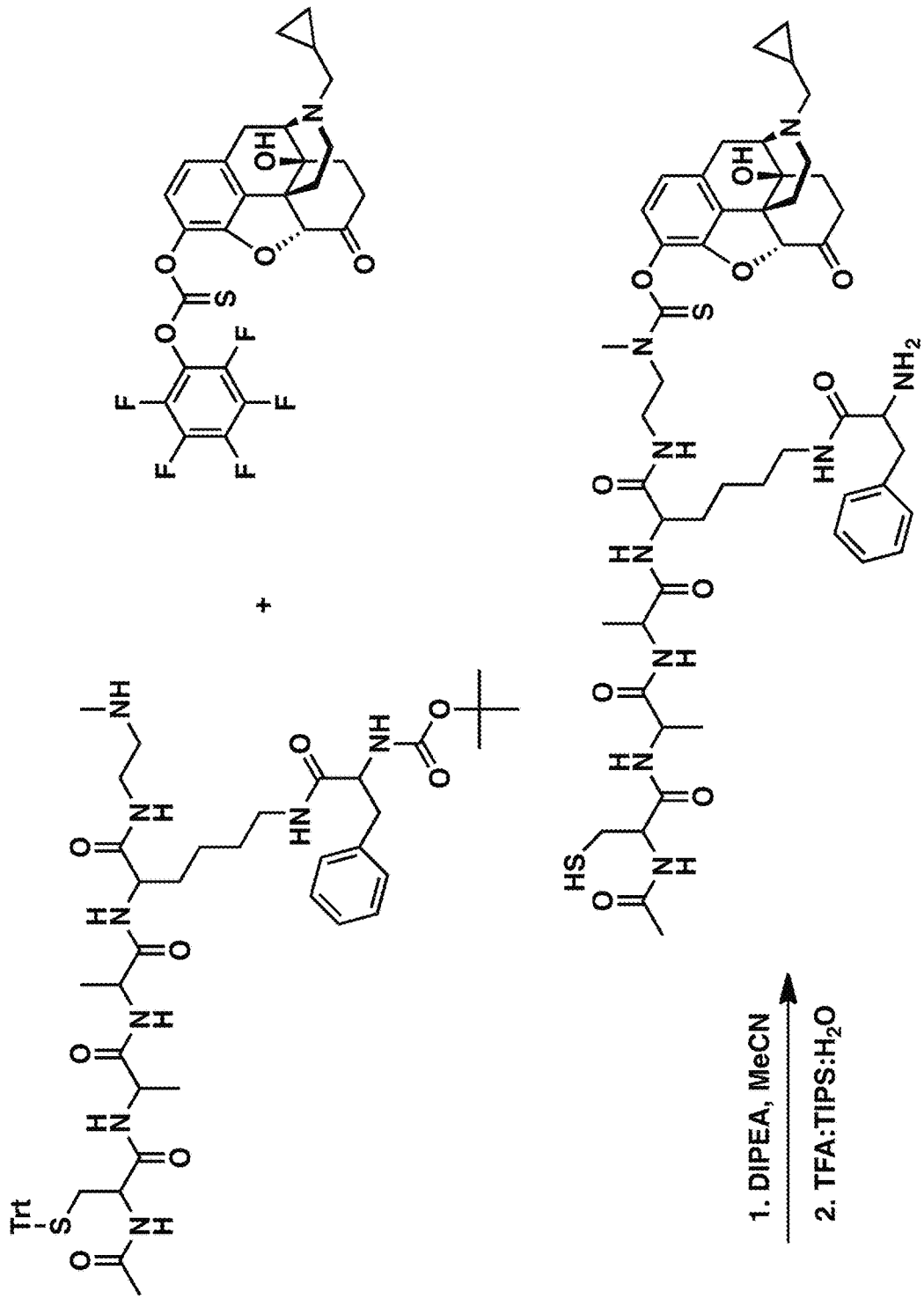
FIG. 27 illustrates synthesis of CAAK(F)-diamino-Naltrexone thionocarbamate and CAAK(F)-diamino-Naltrexone carbamate (Scheme 13).
Figure 27:
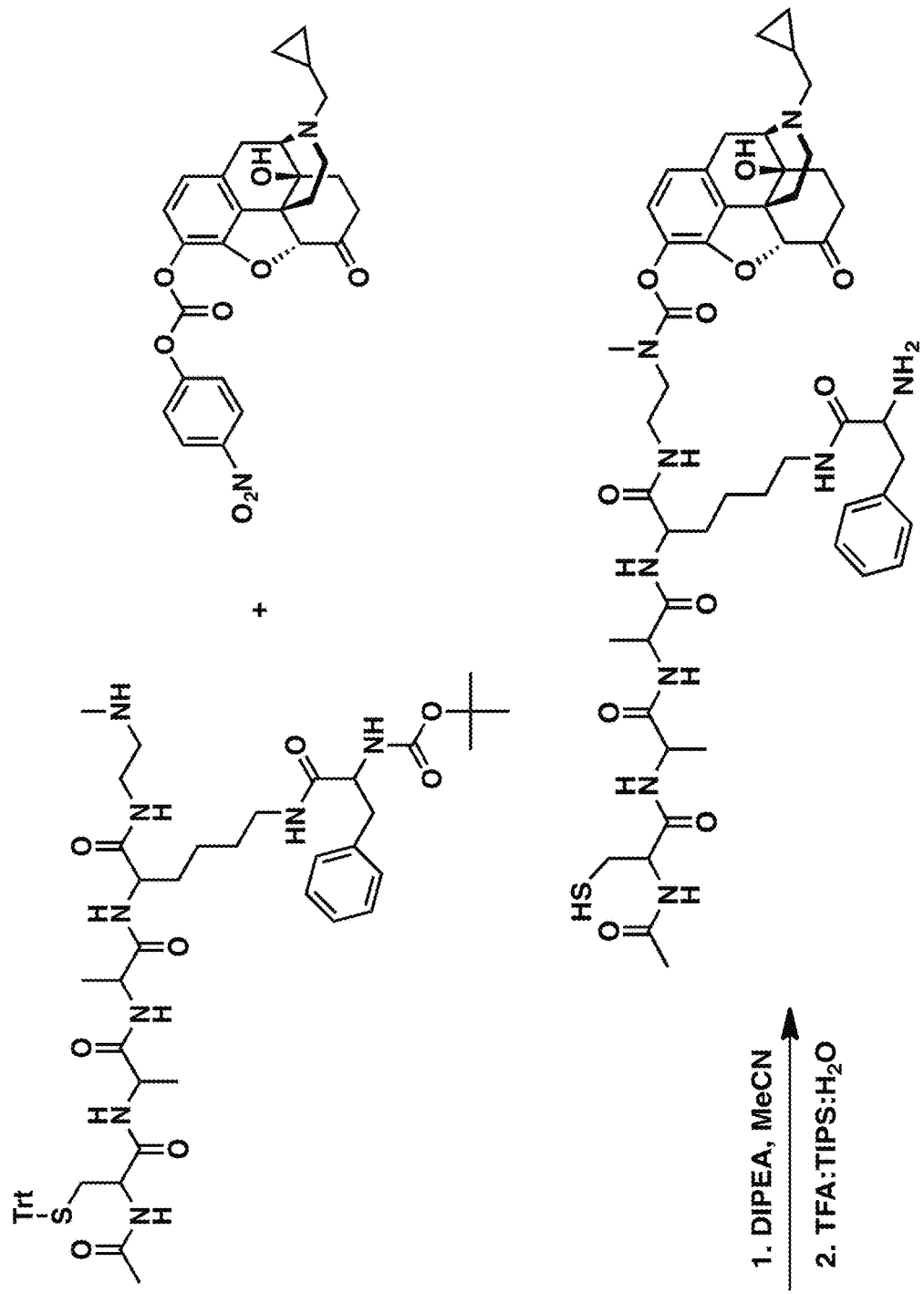

Each modified Naltrexone was then coupled onto the CAAK(F) peptide containing the C-terminal diamino linker by first dissolving the peptide in acetonitrile under magnetic stirring followed by addition of the modified Naltrexone (2 eq) and N,N-diisopropylethylamine (2.5 eq). After 3 hours, solvent was removed under vacuum and redissolved into a mixture of water and acetonitrile and purified by HPLC equipped with a C18 column running a 90/10% to 0/100% $H_2O$/MeCN gradient with 0.1% TFA over 15 minutes followed by a 5-minute isocratic hold at 100% MeCN with 0.1% TFA. Subsequent deprotection of the peptides was carried out using a solution of 95% TFA, 2.5% TIPS, and 2.5% H2O as shown in FIG. 27. The solutions were then concentrated under vacuum and precipitated into cold ether to produce the deprotected peptide. The desired products were collected and confirmed using ESI-MS.

Elastomer Synthesis

Figure 28:
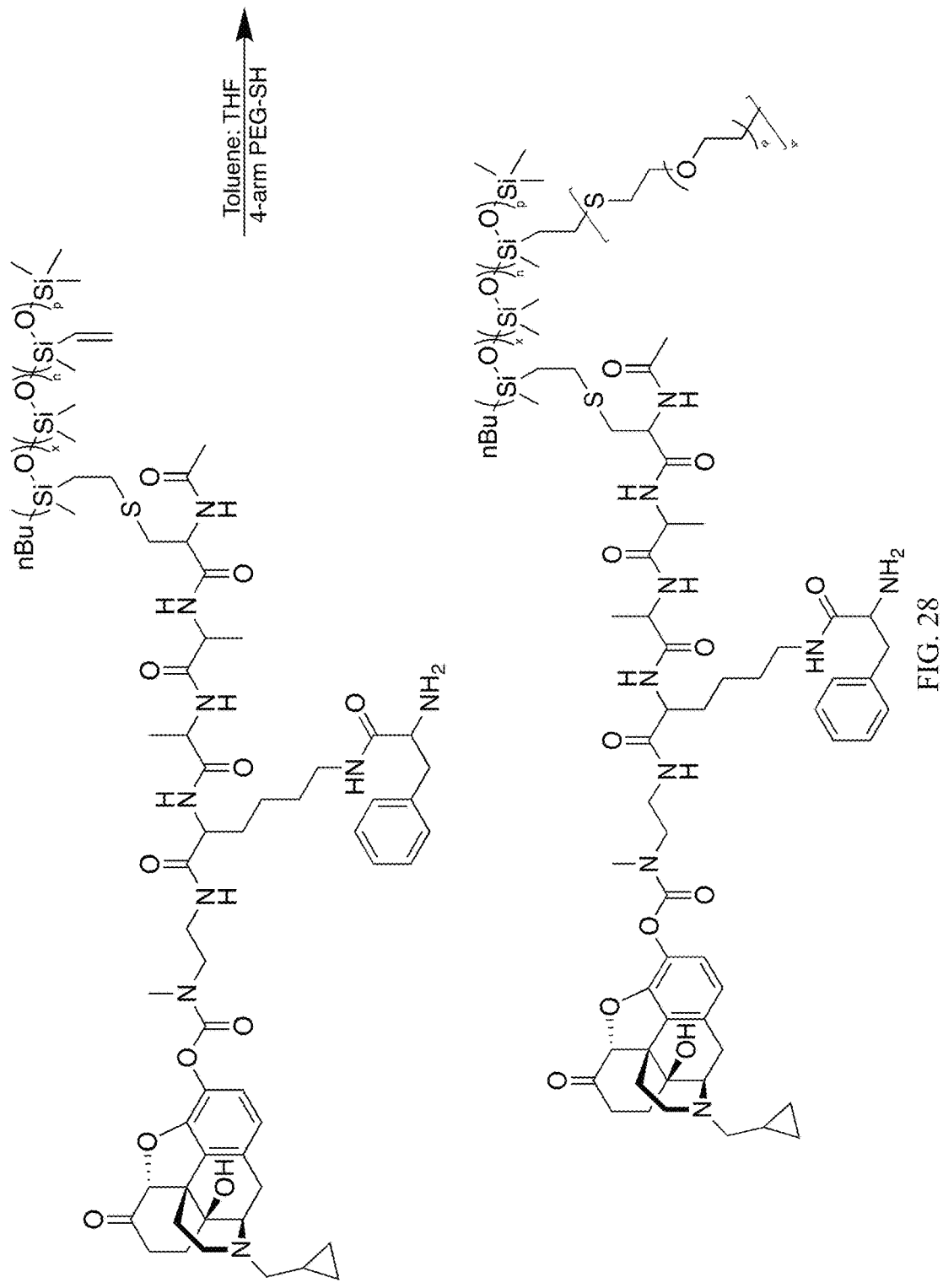
FIG. 28 illustrates crosslinking of the PDMS-CAAK(F)-diamino-Naltrexone-polysiloxane conjugate with 4-arm PEG-SH (Scheme 14).

The PDMS copolymer with 12% vinyl groups was dissolved in minimal toluene. Separately the peptide-Naltrexone conjugate (1 eq to vinyl groups) was combined with Irgacure 2959 (0.2 eq to vinyl groups) and dissolved in (1:2 parts toluene: tetrahydrofuran THF). The solution was then freeze-pump-thawed three times, sealed under argon, and irradiated under UV light (365 nm) for 50 minutes as shown in FIG. 28.

After the UV irradiation, the reaction was quenched by exposing it to oxygen. 4-arm PEG-SH (0.5 eq SH to every vinyl group) and Irgacure 2959 (0.1 eq to vinyl groups) was dissolved in minimal THF. This solution was then added to polymer-peptide conjugate and this was again freeze-pump-thawed three times, sealed under argon, and irradiated with UV light (365 nm) for an additional 90 minutes. This was then quenched by exposing to oxygen and the solvent was removed under vacuum, producing a rigid elastomer. The elastomer was tested on its resistance to mechanical stress (via crushing with a hammer and shaving with a razor) under various conditions. The elastomer remained noncrushable upon testing after it was cooled to 4° C. for 12/24 hours, cooled to −20° C. for 12/24 hours, heated to 260° C. for 15/30/60 minutes, and microwaved for up to 5 minutes.

Figure 12:
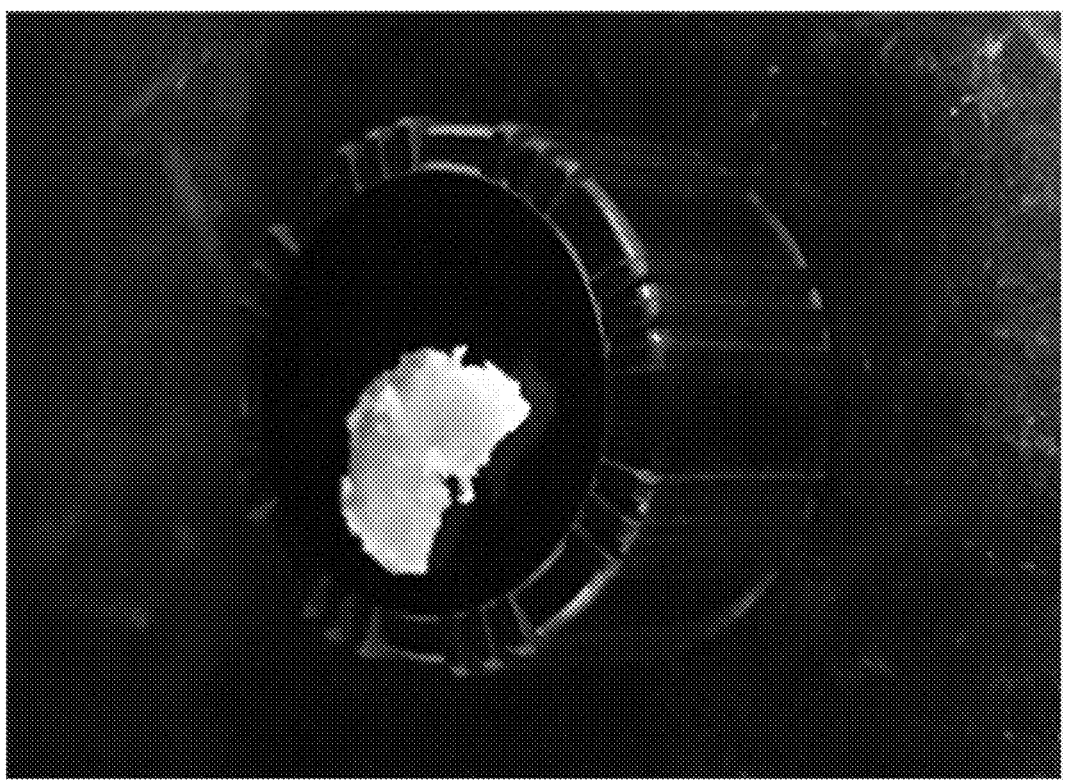
FIG. 12 is an image showing that elastomer containing CAAK(F)-diamino-Naltrexone conjugated onto PDMS cross-linked using 4-arm PEG-SH.

FIG. 12 shows an image of the Elastomer containing CAAK(F)-diamino-Naltrexone conjugated onto PDMS cross-linked using 4-arm PEG-SH.

Peptides Preparation and Characterization:

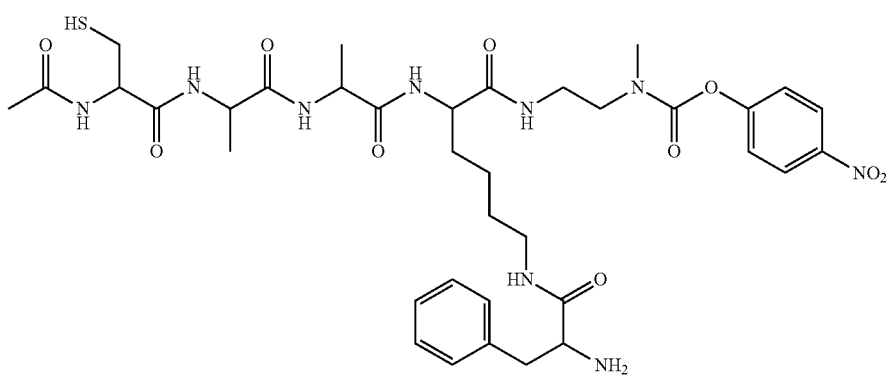

CAAK(F)-diamino-pNA
Calc. [M+]: 802.3573 Observed [M+]: 802.3361

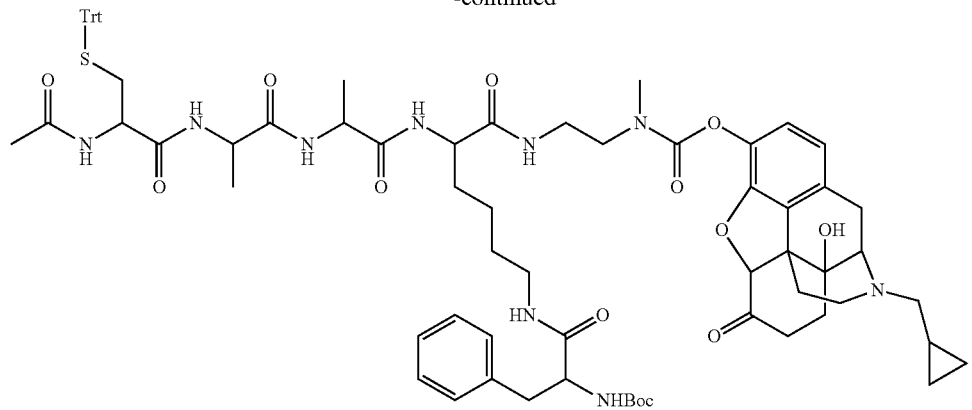

CAAK(F)-diamino-Naltrexone (carbamate-linked)
Calc. [M+]: 1368.6392 Observed [M+]: 1368.5975

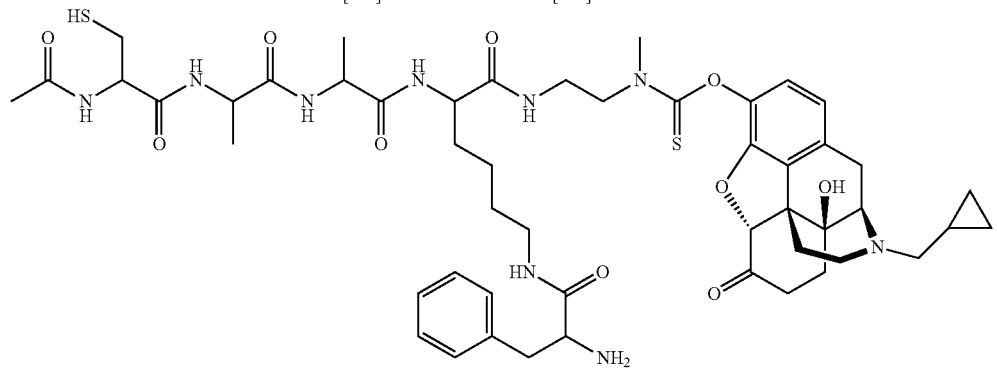

CAAK(F)-diamino-Naltrexone (thionocarbamate-linked)
Calc. [M+Na]: 1042.4492 Observed [M+Na]: 1042.4596 pNA Release Assay

A stock solution of the CAAK(F)-diamino-pNA was prepared in dimethyl sulfoxide (DMSO) to produce a 16.0 mg/mL solution. A 7.5 mg/mL stock solution of the trypsin was prepared in 50 mM NH4HCO3 buffer (pH=8.05). A 7.5 mg/mL stock solution of chymotrypsin was prepared in 50 mM NH4HCO3 buffer (pH=8.05).

A 96 well plate was used for monitoring the solutions at 405 nm using a plate reader. 20 μL of the peptide was combined with 62.0/66.6 μL of no enzyme, trypsin only, chymotrypsin only, or with both enzymes respectively. All solutions were diluted to a total volume of 200 μL using 50 mM NH4HCO3 (pH=8.05). Blanks were prepared by combining the enzymes with DMSO/buffer and their absorbances were subtracted from the cleavage conditions. Additionally, the residual signal from the peptide in the presence of no enzymes was also used as a blank and subtracted out from enzymatic conditions.

Figure 13:
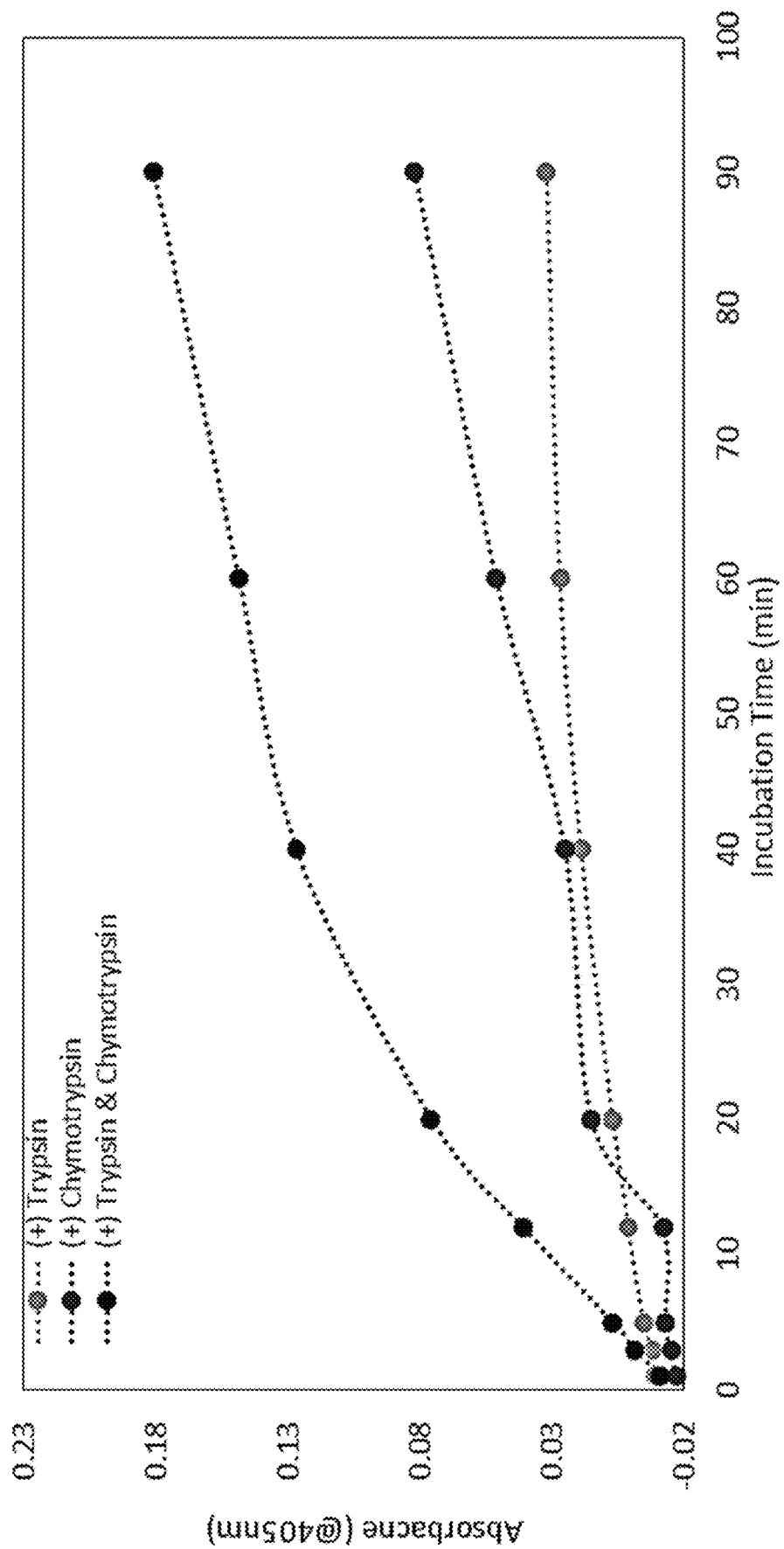
FIG. 13 is a graph showing that 2 mM CAAK(F)-diamino-pNA was incubated with trypsin and/or chymotrypsin for 90 minutes at 37° C. 55% of the theoretical pNA was released after 90 minutes of incubation.

FIG. 13 shows that 2 mM CAAK(F)-diamino-pNA was incubated with trypsin and/or chymotrypsin for 90 minutes at 37° C. 55% of the theoretical pNA was released after 90 minutes of incubation.

Naltrexone Release Assay

A stock solution of the peptide was prepared in DMSO to produce a 20.0 mg/mL solution. A 11.65 mg/mL stock solution of the trypsin was prepared in 50 mM NH4HCO3 buffer (pH=8.05). A 12.5 mg/mL stock solution of chymotrypsin was prepared in 50 mM NH4HCO3 buffer (pH=8.05).

50 μL of the peptide solution was combined with 100 μL of either/both enzymes into an Eppendorf low-bind tube and diluted to 500 μL with NH4HCO3 buffer (pH=8.05). Blanks were prepared by combining the enzymes with DMSO/buffer and their absorbances were subtracted from the cleavage conditions. The residual signal from the peptide in the presence of no enzymes was also used as a blank and subtracted out from enzymatic conditions. The solutions were placed in an incubator at 37° C. for the remainder of the experiment. Aliquots were removed from the sample over the course of the experiment. 50 μL aliquots were combined with 50 μL of a quenching solution (1 mg/mL TCEP, 2.5% TFA, 48.75% H2O, 48.75 MeCN) bringing the pH of the solution below the active range of the proteases while keeping the peptide reduced. These solutions were then filtered and run on a C18 analytical HPLC using a 70/30% to 5/95% H$_2$O/MeCN gradient with 0.1% TFA over 15 minutes with a 5-minute isocratic hold at 95% MeCN (3 mL/min). The cleavage was monitored by integrating the appearance of a peak at 5.8 min corresponding to the same retention time as Naltrexone run under identical conditions.

Figure 14:
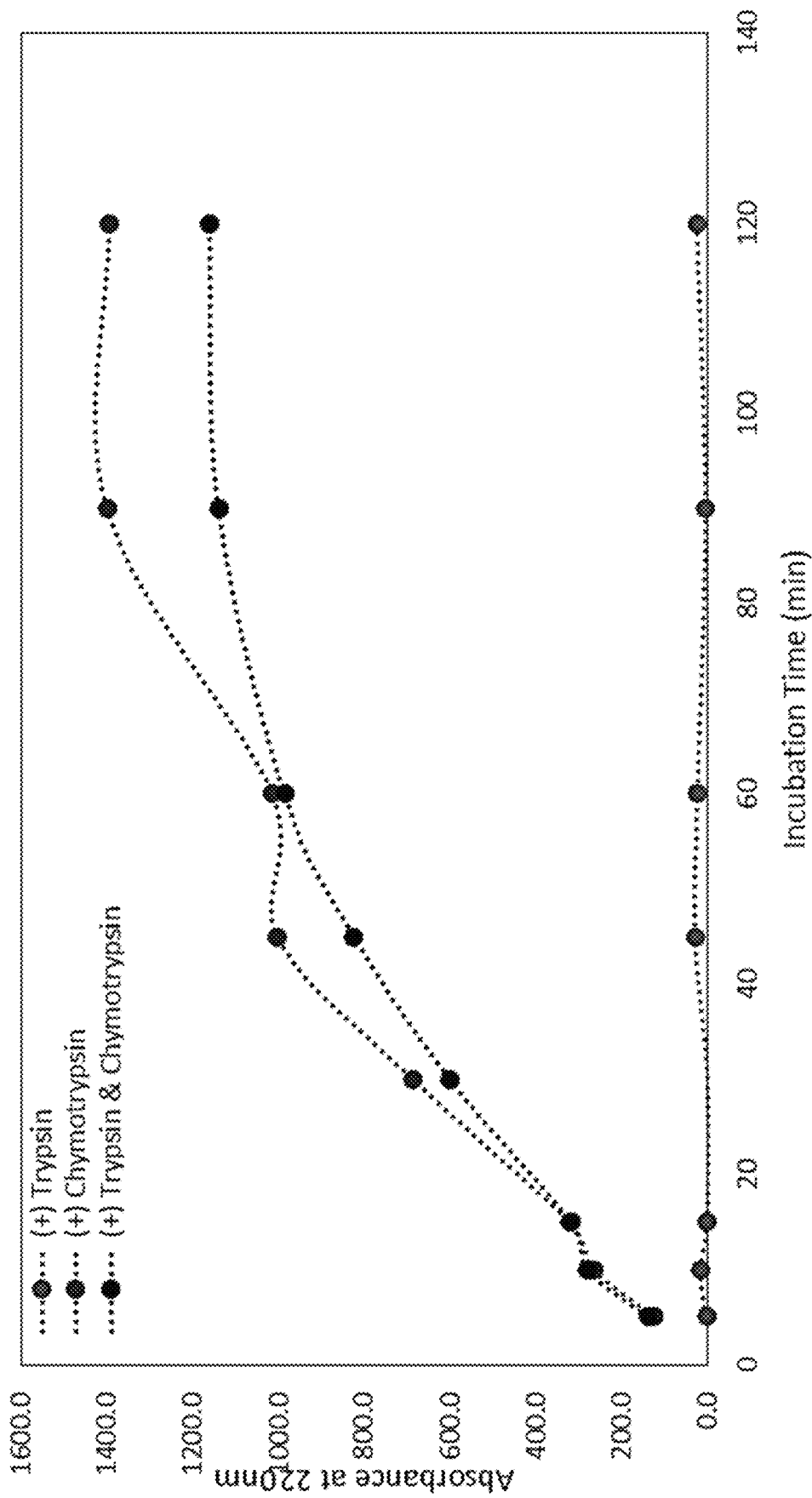
FIG. 14 is a graph showing that 2 mM CAAK(F)-diamino-Naltrexone (carbamate-linked) was incubated with trypsin and/or chymotrypsin for 120 minutes at 37° C.

FIG. 14 shows the results when 2 mM CAAK(F)-diamino-Naltrexone (carbamate-linked) was incubated with trypsin and/or chymotrypsin for 120 minutes at 37° C.

Figure 15:
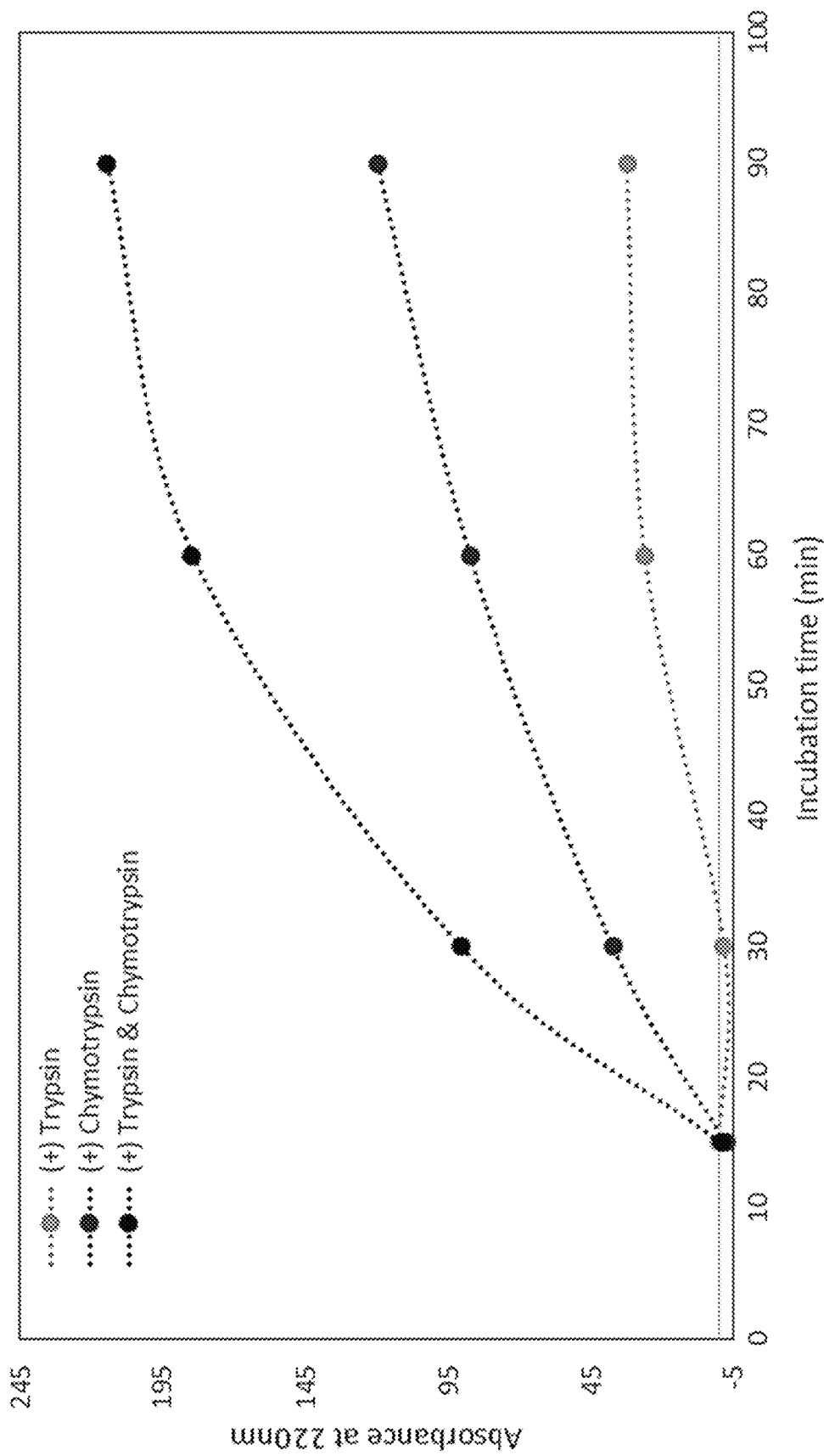
FIG. 15 is a graph showing that 2 mM CAAK(F)-diamino-Naltrexone (thionocarbamate-linked) was incubated with trypsin and/or chymotrypsin for 90 minutes at 37° C.

FIG. 15 shows the results when 2 mM CAAK(F)-diamino-Naltrexone (thionocarbamate-linked) was incubated with trypsin and/or chymotrypsin for 90 minutes at 37° C.

Example 10

Alternative Methods for Naltrexone Activation

Naltrexone Activation

The ketone of Naltrexone could only be modified after first protecting its phenol as a phenyl methyl ether. The phenol was methylated by dissolving Naltrexone (1 eq) in 10 ml DCM and then adding potassium carbonate (5 eq) followed by iodomethane (20 eq). The reaction was stirred for 18 hours and then diluted with DCM and washed several times with a mixture of water and saturated bicarbonate solution followed by drying over magnesium sulfate and concentration under vacuum. The product, 0-Me Naltrexone, was recovered in quantitative yield. The ketone of 0-Me Naltrexone was then modified by first dissolving potassium bis(trimethylsilyl)amide (KHMDS; 3 eq) in 5 ml of dry dimethoxyethylene glycol (DME) in an oven dried flask under Argon and then cooling the mixture to −78° C. in a dry ice/acetone bath. O-Me Naltrexone (1 eq) was added dropwise in 2 ml of dry DME and stirred at −78° C. for 30 minutes. Meanwhile, pentafluorophenyl chlorothionoformate (3 eq) was dissolved in a separate oven dried flask followed by boron trifluoride etherate (3 eq). The solution was then cooled to −78° C. in a dry ice/acetone bath for 15 minutes. Next, the solution containing O-Me Naltrexone was cannulated into the other flask and the entire mixture was allowed to stir at −78° C. for 30 minutes and then for 60 minutes after removal from the bath. The reaction was then concentrated under vacuum and redissolved in a minimal amount of DCM and precipitated three times in hexanes. Finally, the desired product was recovered by dissolving the remaining material in approximately 60% acetonitrile and purifying it by HPLC using a gradient of 40/60% to 5/95% $H_2O$/acetonitrile gradient with 0.1% TFA over 15 minutes followed by a 5-minute isocratic hold at 95% acetonitrile with 0.1% TFA. Typical yields were around 11% and so the reaction needs to be scaled. The identities of the desired products were confirmed using $^1H$ NMR, $^{13}C$ NMR, and ESI-MS.

Scheme 15. Synthesis of O—Me Naltrexone Enol Pentafluorophenylthionocarbonate.

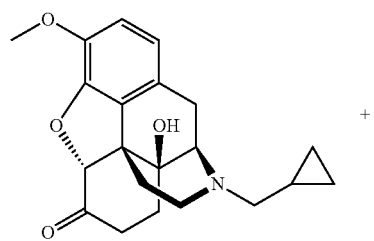

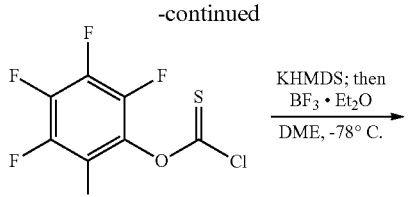

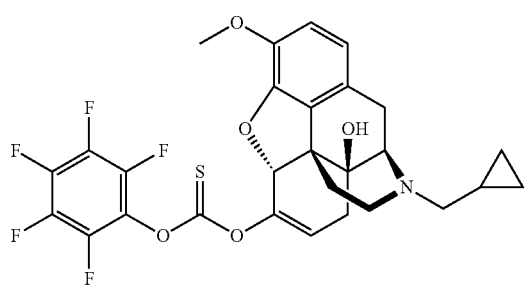

Naltrexone Conjugation to the Peptide

Each modified Naltrexone was then coupled onto the CAAK(F) peptide containing the C-terminal diamino linker by first dissolving the peptide in acetonitrile under magnetic stirring followed by addition of the modified Naltrexone (2 eq) and DIPEA (2.5 eq). After 3 hours, solvent was removed under vacuum and redissolved into a mixture of water and acetonitrile and purified by HPLC equipped with a C18 column running a 90/10% to 0/100% H2O/acetonitrile gradient with 0.1% TFA over 15 minutes followed by a 5-minute isocratic hold at 100% acetonitrile with 0.1% TFA. Subsequent deprotection of the peptides was carried out using a solution of 95% TFA, 2.5% TIPS, and 2.5% $H_2O$. This was then concentrated under vacuum and precipitated into cold ether to produce the deprotected peptide. The desired products were collected and confirmed using ESI-MS.

Scheme 16. Synthesis of CAAK(F)-diamino-Naltrexone enol thionocarbamate.

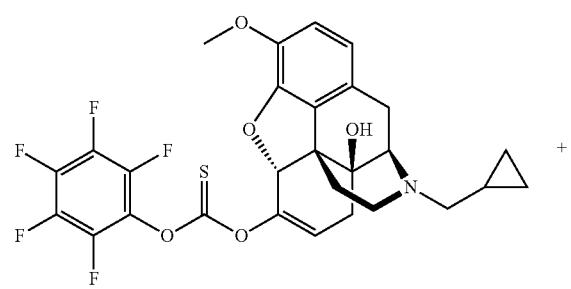

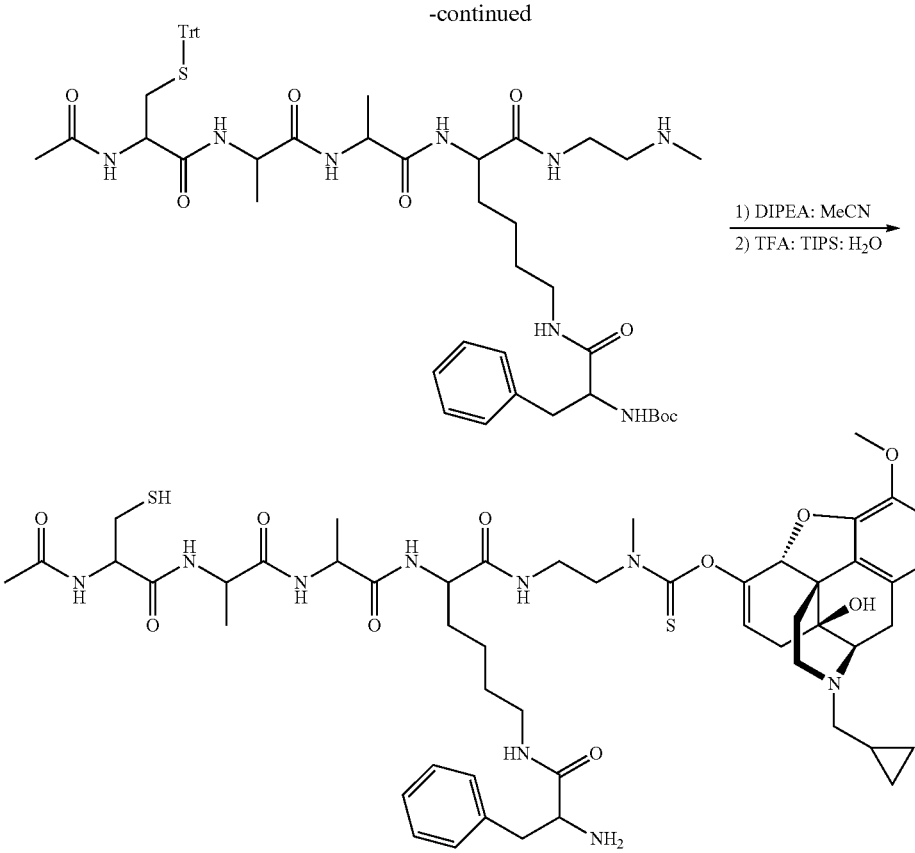

Stability Analysis

In order to determine the stability of the enzymatically cleavable covalent linkage between the dual-enzyme responsive peptide and Naltrexone, the drug conjugates (below) were synthesized and subjected to a range of different pH buffers that were chosen to emulate the pH range of typical household chemicals (pH 2-10).

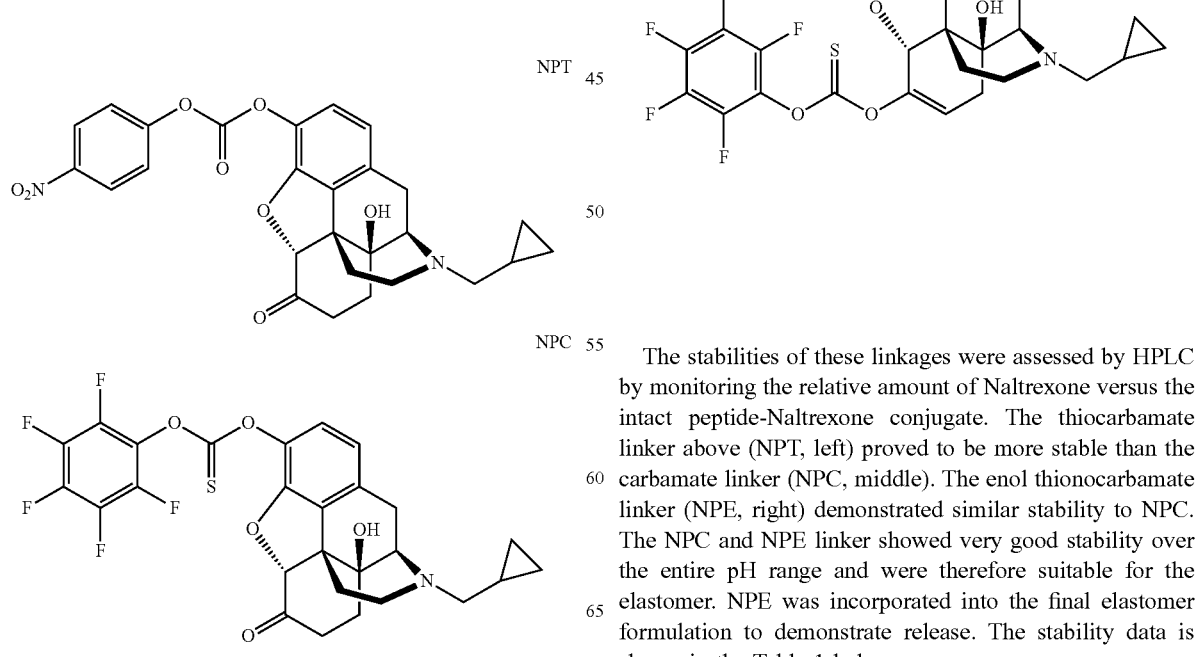

The stabilities of these linkages were assessed by HPLC by monitoring the relative amount of Naltrexone versus the intact peptide-Naltrexone conjugate. The thiocarbamate linker above (NPT, left) proved to be more stable than the carbamate linker (NPC, middle). The enol thionocarbamate linker (NPE, right) demonstrated similar stability to NPC. The NPC and NPE linker showed very good stability over the entire pH range and were therefore suitable for the elastomer. NPE was incorporated into the final elastomer formulation to demonstrate release. The stability data is shown in the Table 1 below.

TABLE 1

The stability data of NPT, NPC and NPE.

| Entry | Sample Name | Sample Retention Time (min) | Percent Degradation, t = 0.5 hr | Percent Degradation, t = 24 hr |
|---|---|---|---|---|
| 1 | Naltrexone | 5.908 | — | — |
| 2 | Naltrexone-Peptide Carbamate Linker (NPC) | 6.433 | 0 | 0 |
| 3 | NPC in pH 2 | 6.078/6.472 | 6.00 | 12.30 |
| 4 | NPC in pH 4 | 6.078/6.472 | 3.50 | 2.89 |
| 5 | NPC in pH 7 | 6.078/6.472 | 1.50 | 3.62 |
| 6 | NPC in pH 9 | 6.078/6.472 | 5.56 | 5.17 |
| 7 | NPC in pH 12 | 6.078/6.472 | 7.03 | 6.94 |
| 8 | Naltrexone-Peptide Thionocarbamate Linker (NPT) | 6.433 | 0.51 | 2.90 |
| 9 | NPT in pH 2 | 6.078/6.472 | 3.23 | 4.10 |
| 10 | NPT in pH 4 | 6.078/6.472 | 1.67 | 2.04 |
| 11 | NPT in pH 7 | 6.078/6.472 | 3.22 | 3.59 |
| 12 | NPT in pH 9 | 6.078/6.472 | 4.69 | 3.37 |
| 13 | NPT in pH 12 | 6.078/6.472 | 5.15 | 6.72 |
| 14 | O-Me Naltrexone | 6.688 | — | — |
| 15 | O-Me Naltrexone-Peptide Enol Thionocarbamate Linker (NPE) | 7.064 | 0 | 1.51 |
| 16 | NPE in pH 2 | 6.688/7.064 | 1.77 | 4.90 |
| 17 | NPE in pH 4 | 6.688/7.064 | 1.38 | 3.41 |
| 18 | NPE in pH 7 | 6.688/7.064 | 2.29 | 3.88 |
| 19 | NPE in pH 9 | 6.688/7.064 | 5.99 | 7.16 |
| 20 | NPE in pH 12 | 6.688/7.064 | 3.28 | 5.38 |

Elastomer Synthesis

The PDMS copolymer with 12% vinyl groups was dissolved in minimal toluene. Separately the peptide-Naltrexone conjugate (1 eq to vinyl groups) was combined with Irgacure 2959 (0.2 eq to vinyl groups) and dissolved in tetrahydrofuran (1:2 parts toluene:THF). The solution was then freeze-pump-thawed three times, sealed under argon, and irradiated under UV light (365 nm) for 50 minutes.

Scheme 17. Crosslinking of the PDMS-CAAK(F)-Naltrexone conjugate with 4-arm PEG-SH

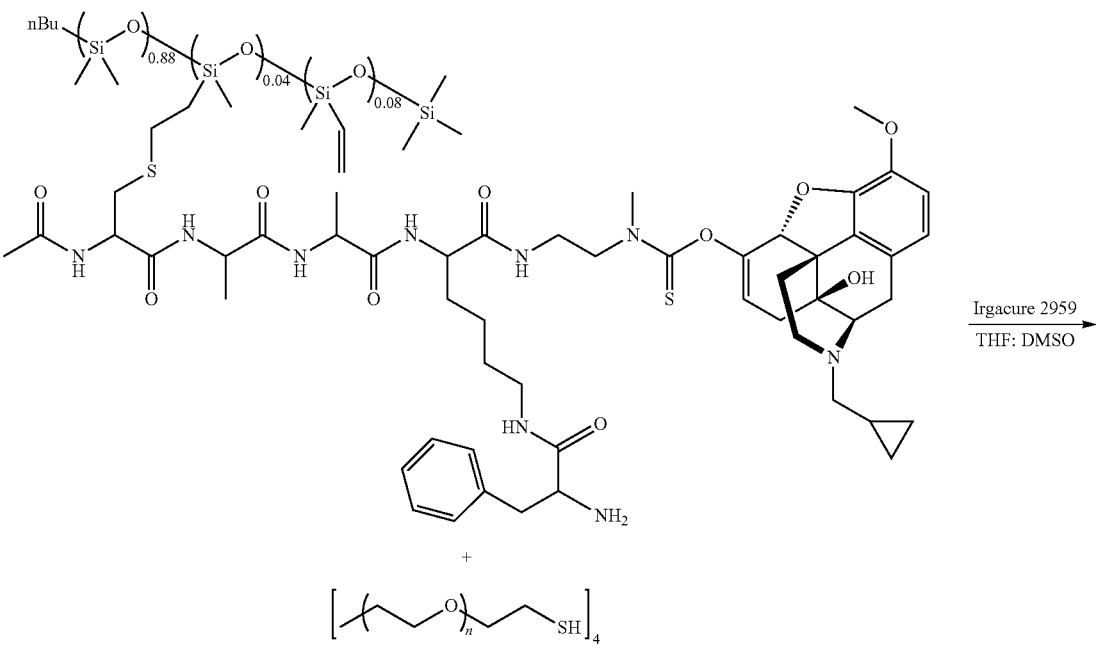

-continued

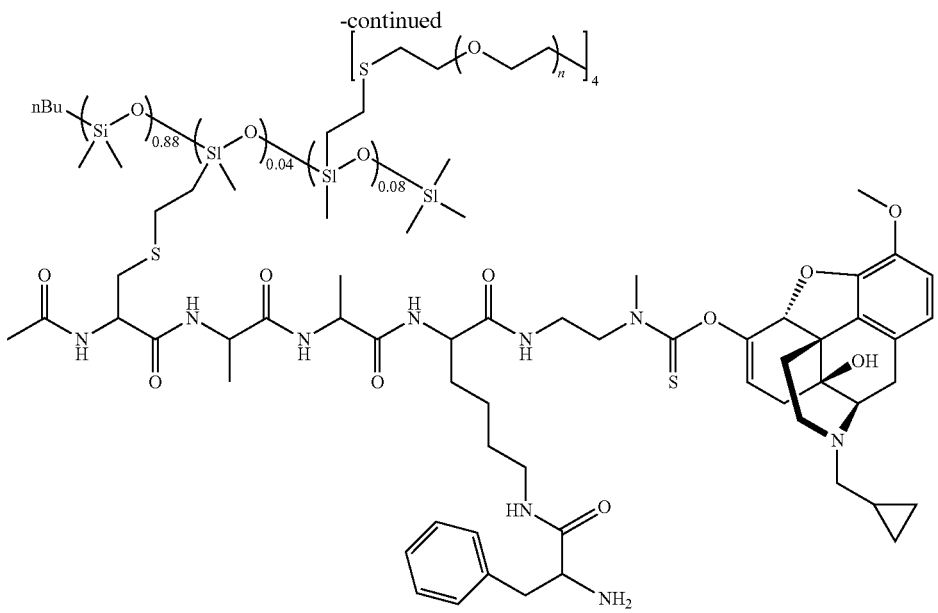

25

After the UV irradiation, the reaction was quenched by exposing it to oxygen. Excess peptide was removed through dialysis using a solution of methanol and dichloromethane (30:70). This material was collected, residual solvent was removed under vacuum and it was dissolved in THF. 4-arm PEG-SH (0.5 eq SH to every vinyl group) and Irgacure 2959 (0.1 eq to vinyl groups) was dissolved in minimal THF. This solution was then added to the polymer-peptide conjugate and this was again freeze-pump-thawed three times, sealed under argon, and irradiated with UV light (365 nm) for an additional 90 minutes. This was then quenched by exposing to oxygen and the solvent was removed under vacuum, producing a rigid elastomer. The elastomer was tested on its resistance to mechanical stress (via crushing with a hammer and shaving with a razor) under various conditions. The elastomer remained rigid upon testing after it was cooled to 4° C. for 12/24 hours, cooled to −20° C. for 12/24 hours, heated to 260° C. for 15/30/60 minutes, and microwaved for up to 5 minutes.

Figure 16:
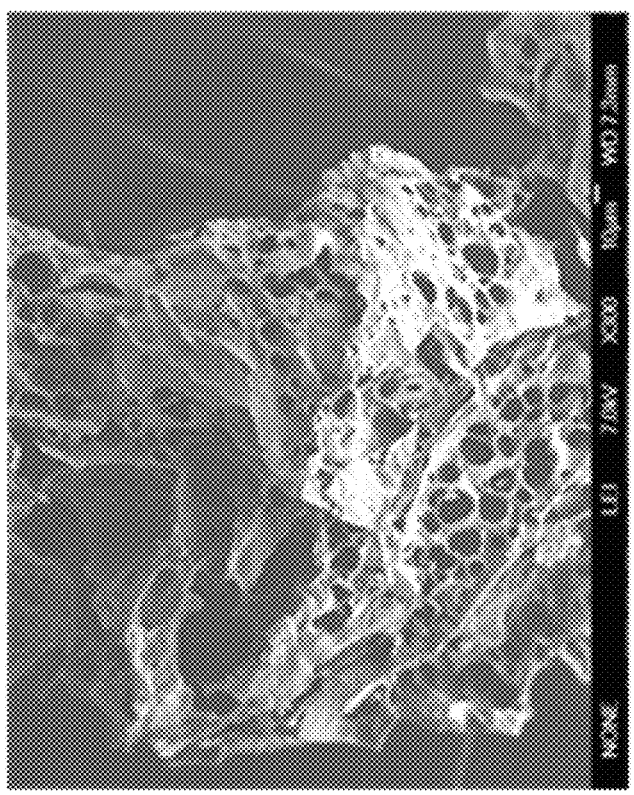
FIG. 16 are a table showing the physical stability of the elastomer containing CAAK(F)-diamino-Naltrexone conjugated onto PDMS crosslinked using 4-arm PEG-SH against a variety of stresses where "pass" means the material is still noncrushable after the treatment and SEM images of the final elastomer.

FIG. 16 shows that physical stability of the elastomer containing CAAK(F)-diamino-Naltrexone conjugated onto PDMS crosslinked using 4-arm PEG-SH against a variety of stresses and SEM images of final elastomer.

Enzyme-Triggered Naltrexone Release

Peptide/elastomer was dissolved in DMSO and diluted using NH$_4$HCO$_3$ buffer (pH=8.05). Four solutions were prepared by adding either; no protease, trypsin only, chymotrypsin only, or both proteases. The solutions were placed in an incubator at 37° C. for the remainder of the experiment. Aliquots were removed from the samples over the course of the experiment. These solutions were then filtered and run on a C18 analytical HPLC using a 70/30% to 5/95% H2O/acetonitrile gradient with 0.1% TFA over 15 minutes with a 5-minute isocratic hold at 95% acetonitrile (1.2 mL/min). The cleavage was monitored by integrating the appearance of the 0-Me Naltrexone peak at 9 min. Naltrexone appearance was confirmed using LCMS.

Figure 17:
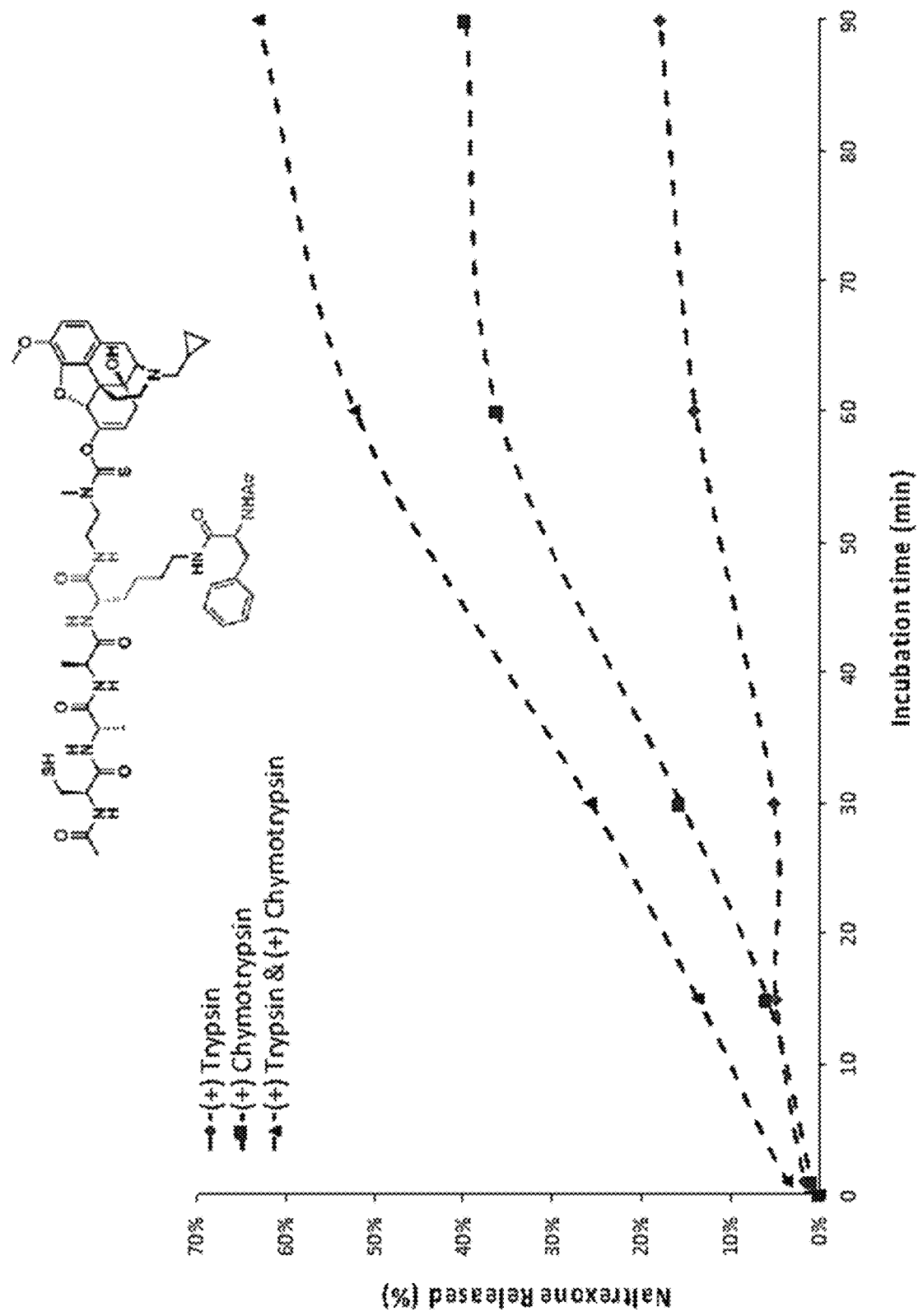
FIG. 17 is a graph showing that 2 mM CAAK(F)-diamino-Naltrexone (enol thionocarbamate-linked) was incubated with trypsin and/or chymotrypsin for 90 minutes at 37° C.

FIG. 17 shows the results when 2 mM CAAK(F)-di-amino-Naltrexone (enol thionocarbamate-linked) was incubated with trypsin and/or chymotrypsin for 90 minutes at 37° C.

Figure 18:
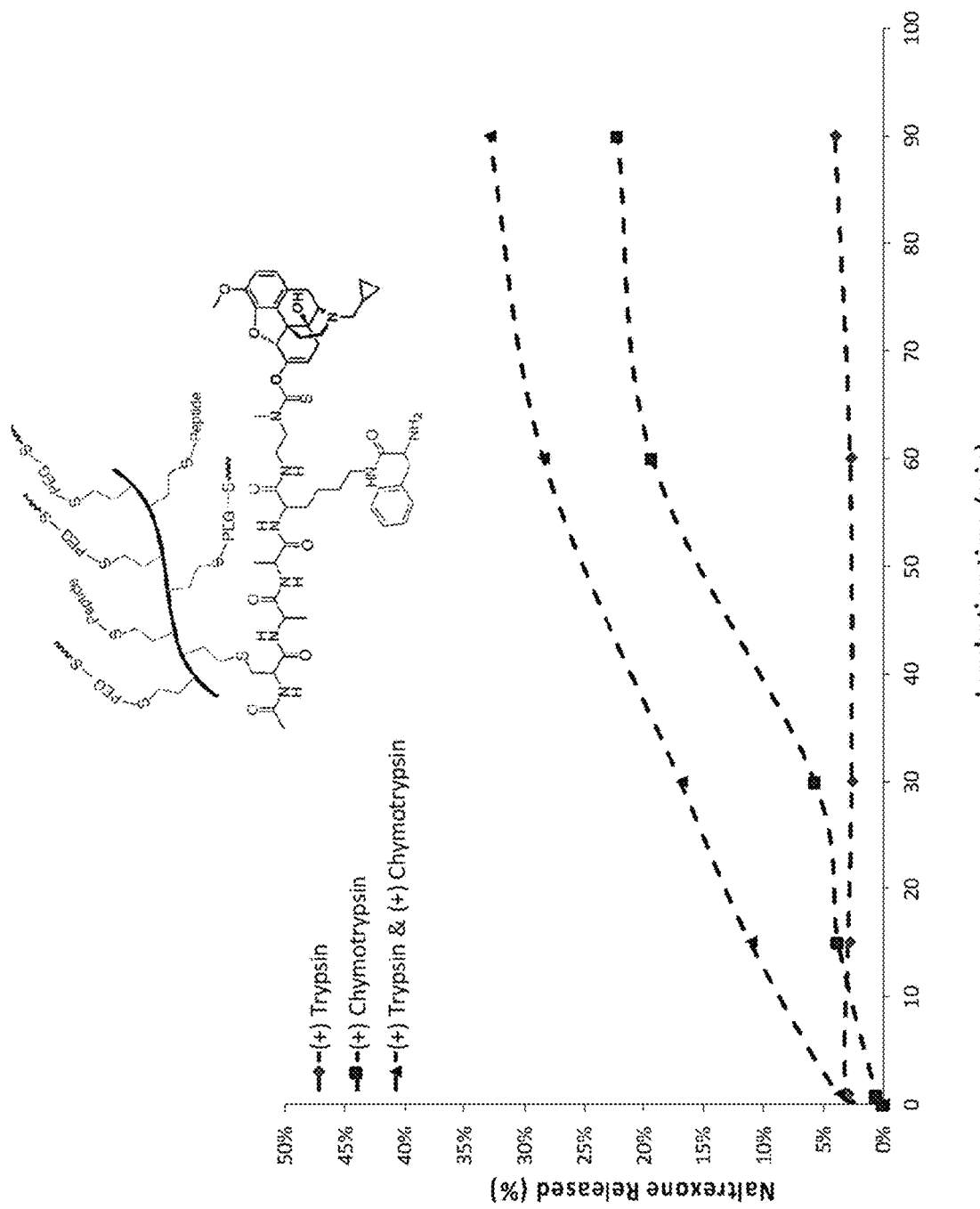
FIG. 18 is a graph showing that 2 mM Elastomer loaded with CAAK(F)-diamino-Naltrexone (enol thionocarbamate-linked) was incubated with trypsin and/or chymotrypsin for 90 minutes at 37° C.

FIG. 18 shows the results when 2 mM Elastomer loaded with CAAK(F)-diamino-Naltrexone (enol thionocarbamate-linked) was incubated with trypsin and/or chymotrypsin for 90 minutes at 37° C.

Unintended Naltrexone from Household Chemicals

The release of Naltrexone from Coca-Cola, Lemon Juice, and Vinegar was monitored using HPLC. Elastomer was incubated in the various substances with aliquots removed periodically over a 12-hour period and injected on a C18 column. There was no substantial release after incubation of the elastomer over a 12-hour time period. LCMS was run to confirm Naltrexone was not present in the 12-hour sample. The red box outlines the 0-Me Naltrexone peak, showing no presence across the 12-hour incubation period. The bottom trace shows injection of Naltrexone in the various substances to demonstrate where it would appear in HPLC if it was released.

Figure 19:
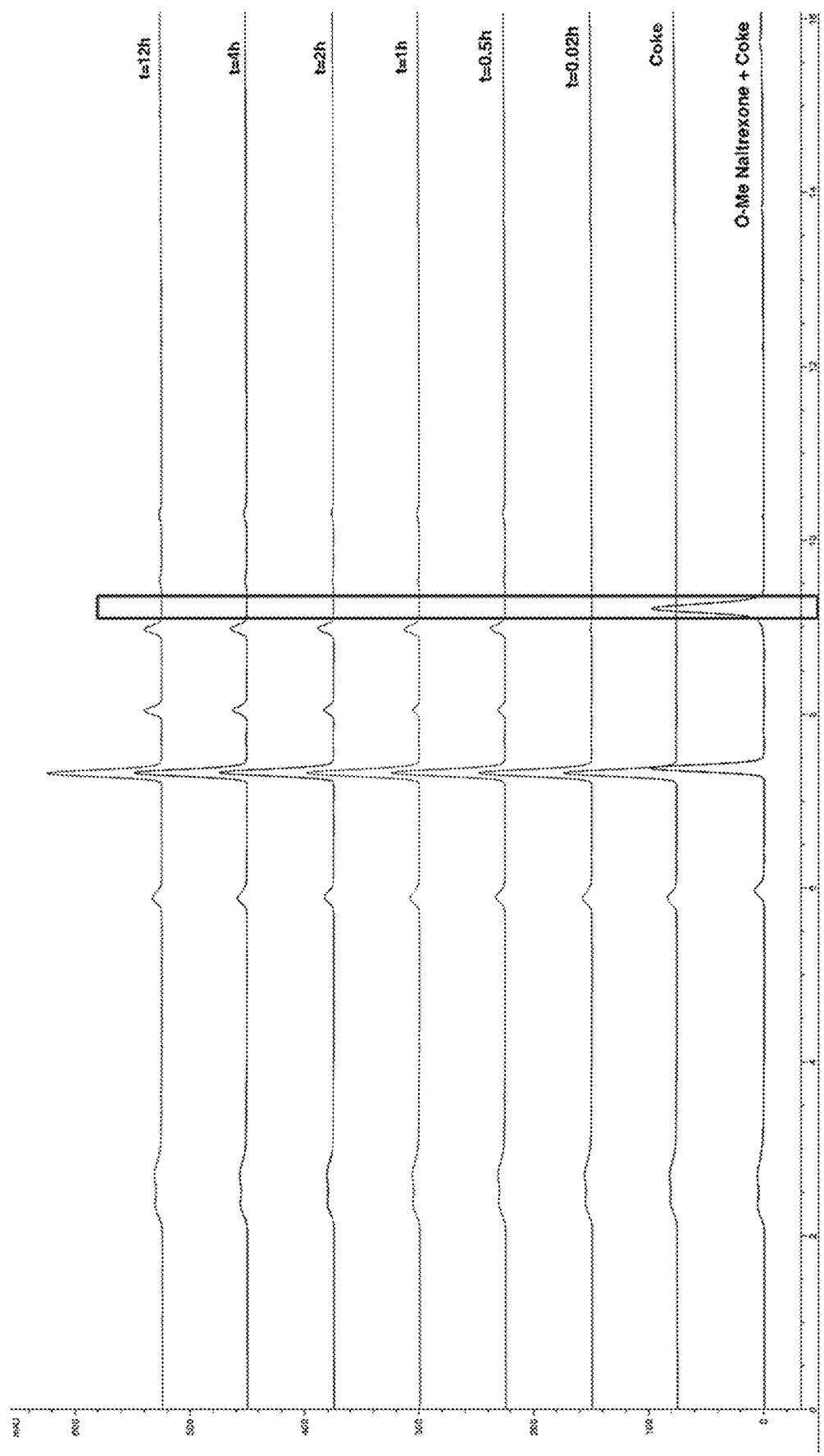
FIG. 19 is a graph showing the release study of Elastomer loaded with CAAK(F)-diamino-Naltrexone (enol thionocarbamate-linked) treated with coca-cola measuring aliquots at 0, 0.02, 0.5, 1, 2, 4, and 12 hours. No appearance of Naltrexone was confirmed by LCMS (indicated by red square) demonstrating no unintended release. The bottom trace is the Naltrexone in coca-cola control.

FIG. 19 shows the unintended release study from coca-cola measuring aliquots at 0, 0.02, 0.5, 1, 2, 4, and 12 hours. No appearance of Naltrexone was confirmed by LCMS.

Figure 20:
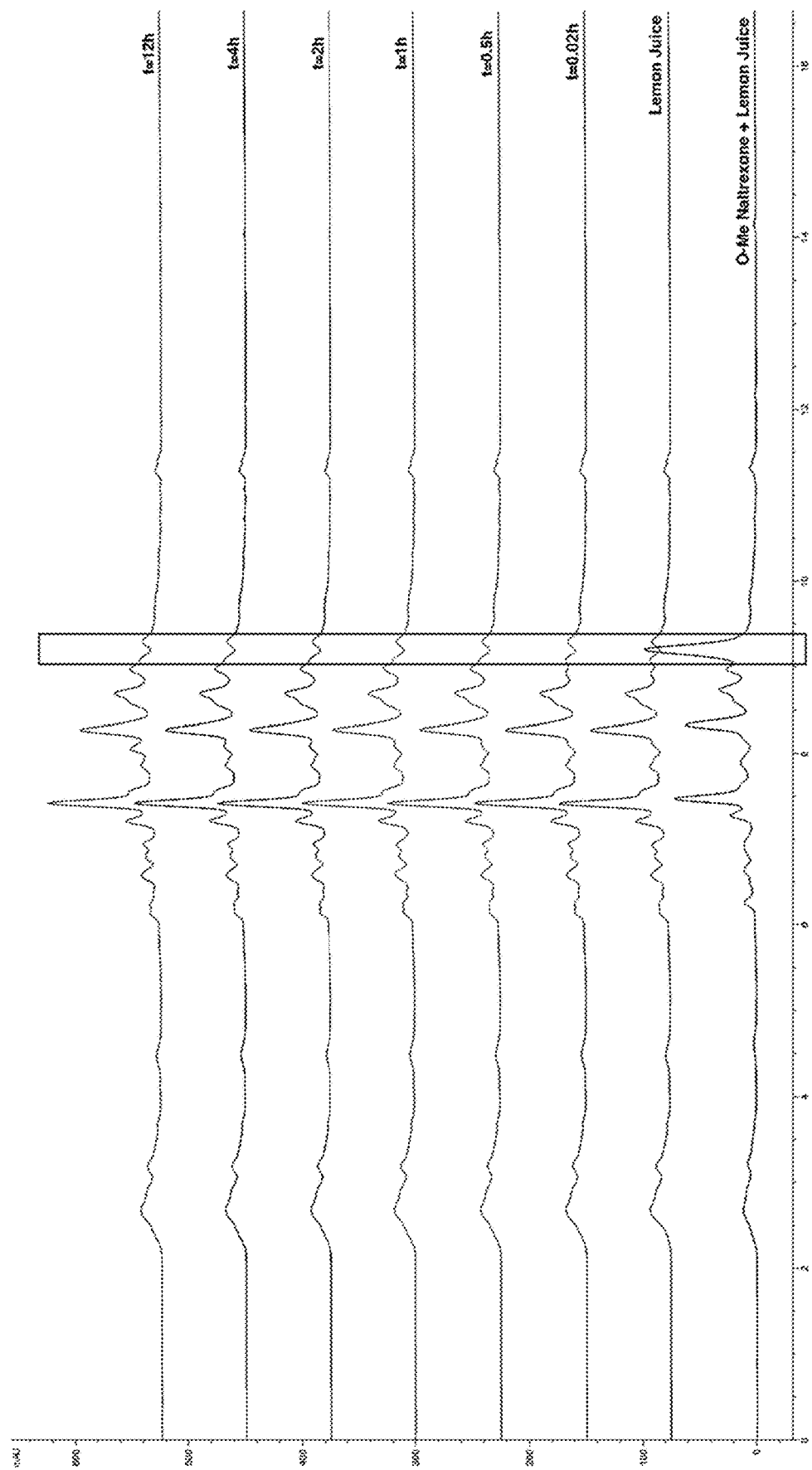
FIG. 20 is a graph showing the release study of Elastomer loaded with CAAK(F)-diamino-Naltrexone (enol thionocarbamate-linked) treated with Lemon-Juice measuring aliquots at 0, 0.02, 0.5, 1, 2, 4, and 12 hours. No appearance of Naltrexone was confirmed by LCMS (indicated by red square) demonstrating no unintended release. The bottom trace is the Naltrexone in lemon juice control.

FIG. 20 shows the unintended release study from Lemon-Juice measuring aliquots at 0, 0.02, 0.5, 1, 2, 4, and 12 hours. No appearance of Naltrexone was confirmed by LCMS.

Figure 21:
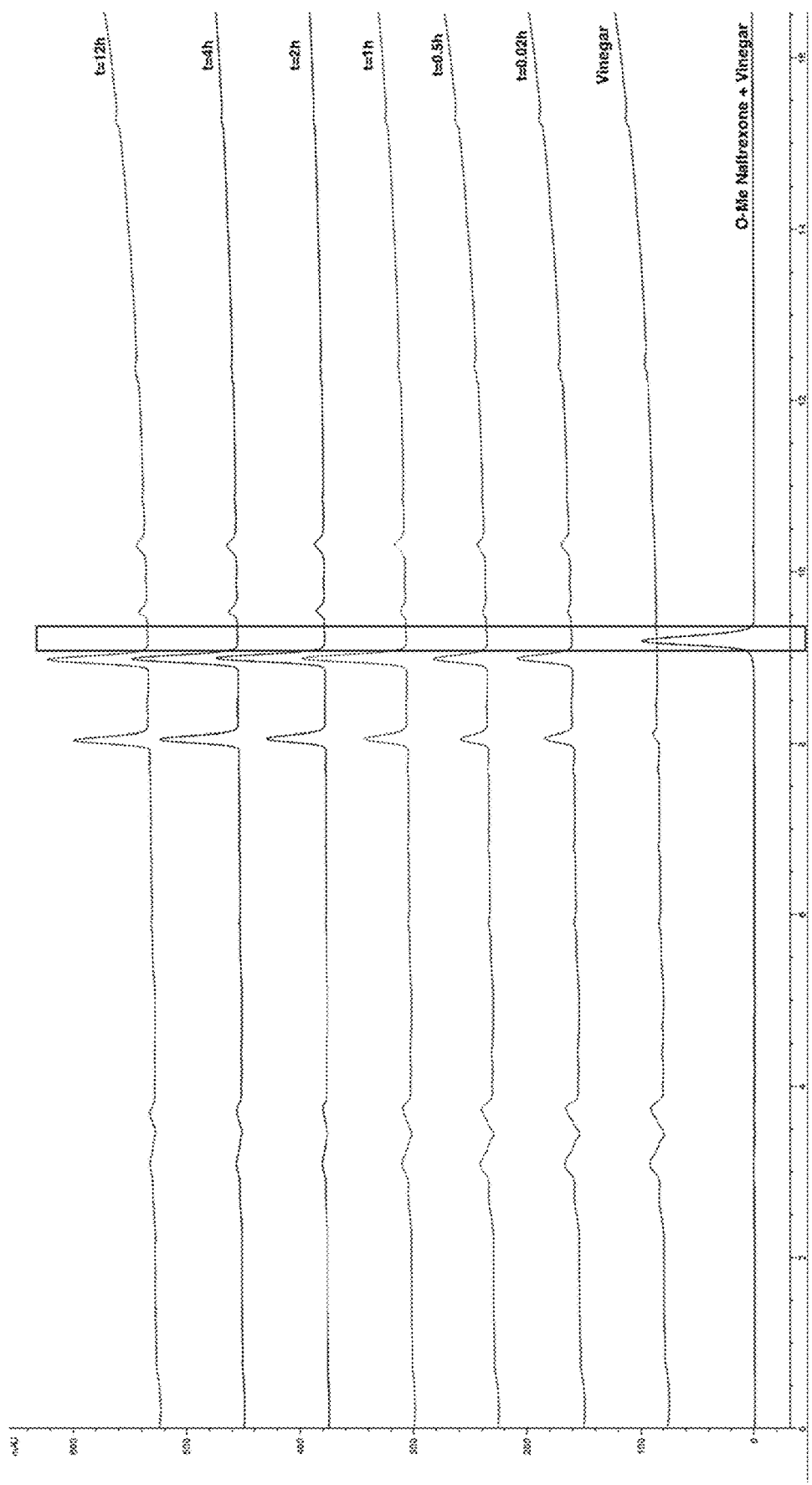
FIG. 21 is a graph showing the release study of Elastomer loaded with CAAK(F)-diamino-Naltrexone (enol thionocarbamate-linked) treated with Vinegar measuring aliquots at 0, 0.02, 0.5, 1, 2, 4, and 12 hours (indicated by red square) demonstrating no unintended release. No appearance of Naltrexone was confirmed by LCMS. The bottom trace is the Naltrexone in vinegar control.

FIG. 21 shows the unintended release study from Vinegar measuring aliquots at 0, 0.02, 0.5, 1, 2, 4, and 12 hours. No appearance of Naltrexone was confirmed by LCMS.

Animal Studies of Elastomer

LD50 of the elastomer was determined as greater than 5000 mg/kg according to the Organization for Economic Cooperation and Development (OECD) guideline. Briefly, the limit test at 5000 mg/kg dose was employed and the LD50 is determined to be greater than 5000 mg/kg after 3 animals survived over a 14-day observation. Sprague-Dawley rats (female, 4 weeks) were acclimated for 2 weeks prior to oral gavage of the elastomer (5000 mg/kg) suspended in phosphate-buffered saline. All rats survived the procedure for the full 14 days, after which they were euthanized.

Figure 22:
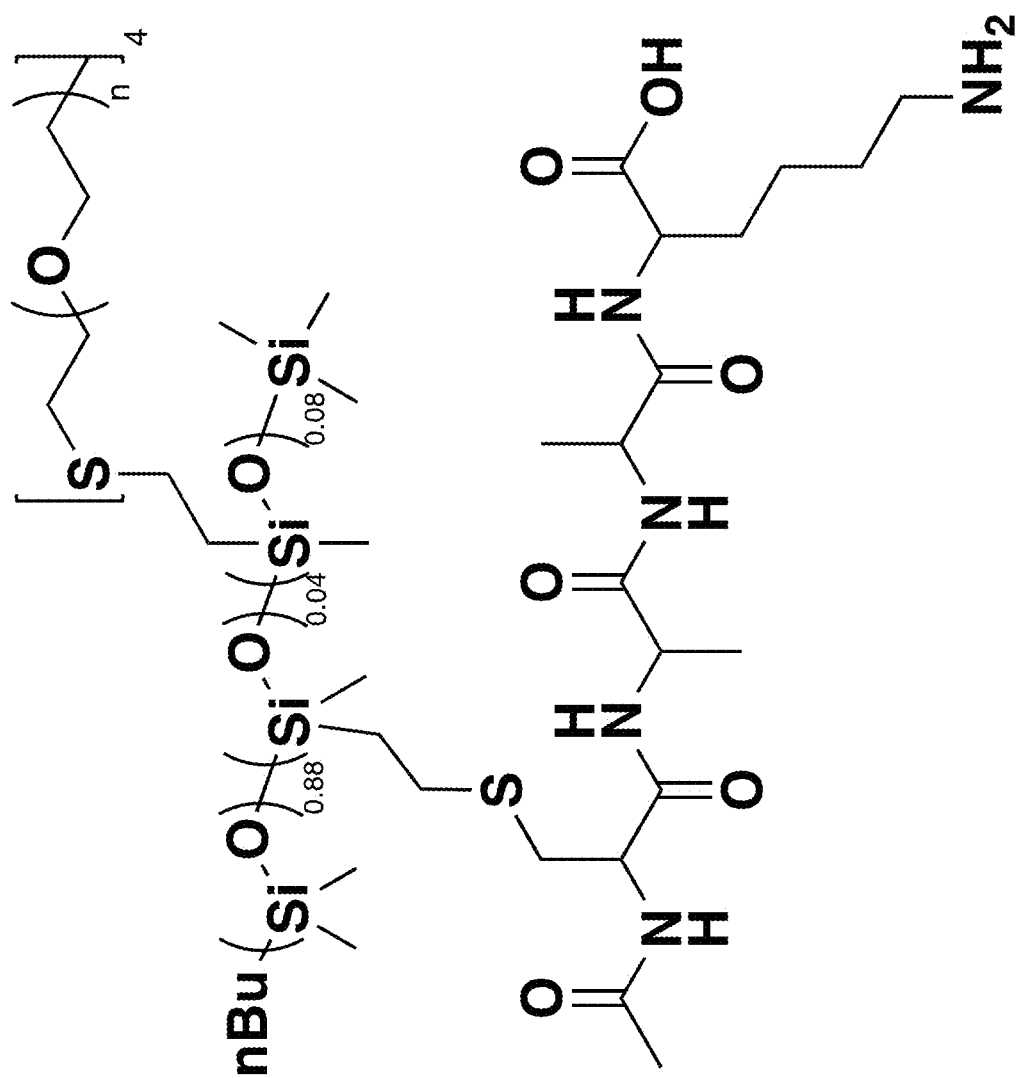
FIG. 22 is a formula showing the chemical structure of CAAK functionalized elastomer used for animal toxicity studies.

FIG. 22 show the chemical structure of CAAK functionalized elastomer used for animal toxicity studies.

Rat growth as measured by weight change is normal compared to the vendor data, showing that elastomers do not obstruct the GI tract. Note that one of the rats was slightly heavier than other rats prior to elastomer injection and grew faster, but it is within the natural weight variability and seems to stem from high liver enzyme value (see below for discussion).

Figure 23:
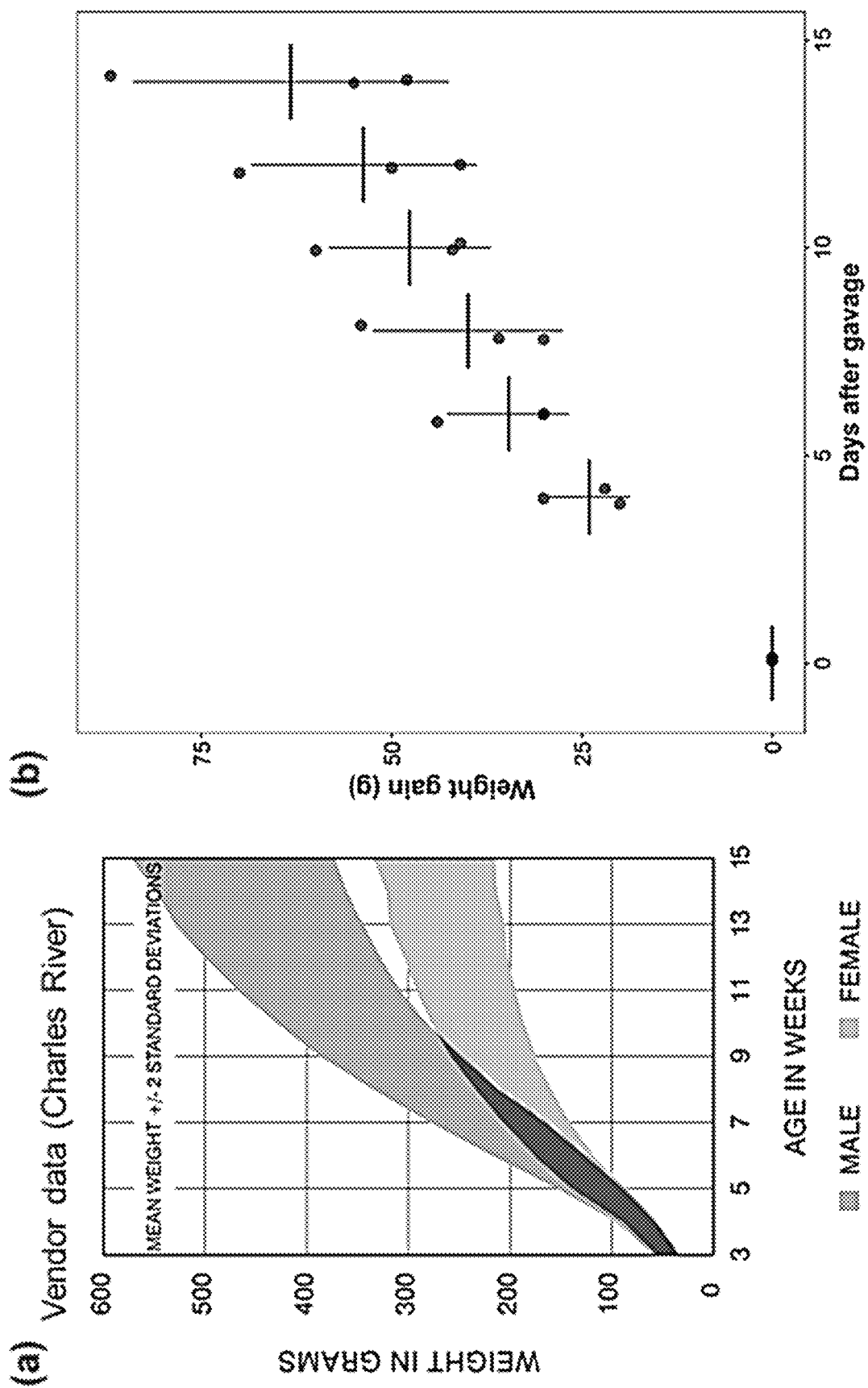
FIGS. 23A-B are a set of graphs showing the results when Rat weight change over time. (a) Normal rat growth curve provided by the vendor (Charles River), (b) weight gain after gavage (horizontal line: mean, vertical line: standard deviation).

FIG. 23 shows the results when Rat weight change over time. (a) Normal rat growth curve provided by the vendor (Charles River), (b) weight gain after gavage (horizontal line: mean, vertical line: standard deviation).

Blood was collected from rats after oral gavage to test for liver and kidney toxicity as well as blood cell counts. Because serum chemistry results are relatively more variable, a baseline measurement was taken prior to oral gavage and tested for alanine aminotransferase (ALT) and aspartate aminotransferase (AST) activities as indicators for liver toxicity, and blood urea nitrogen (BUN) and creatinine (Creat) as indicators for kidney toxicity (Table 2). The pre-gavage data has shown that the heavier rat has slightly elevated ALT level (1.3 std. dev. above mean). Given that elevated ALT levels have been associated with obesity, the slightly higher weight of this rat may be due to its naturally high ALT level prior to the study.

TABLE 2

Baseline serum chemistry results prior to oral gavage.

|  | ALT | AST | BUN | Creat |
|---|---|---|---|---|
| Rat 1 | 100 | 93 | 10 | 0.32 |
| Rat 2 | 67 | 112 | 9 | 0.43 |
| Rat 3 | 80 | 129 | 9 | 0.42 |
| Average | 82 ± 17 | 111 ± 18 | 9 ± 1 | 0.39 ± 0.06 |
| Normal | 57 ± 32 | 112 ± 65 | 13 ± 4 | 0.47 ± 0.10 |

ALT: alanine aminotransferase,
AST: aspartate aminotransferase,
BUN: blood urea nitrogen,
Creat: creatinine.
Normal values (mean ± standard deviation) are published by the vendor (Charles River).

The serum chemistry and blood counts conducted 14 days after oral gavage showed that the elastomer did not induce any noticeable changes in blood cells or liver/kidney function (Table 3).

TABLE 3

Serum chemistry and blood counts 14 days after oral gavage.

|  | Liver enzymes | | Kidney function | | Blood cell counts | |
|---|---|---|---|---|---|---|
|  | ALT | AST | BUN | Creat | WBC | RBC |
| Rat 1 | 70 | 82 | 16 | 0.43 | 8.9 | 7.04 |
| Rat 2 | 56 | 73 | 17 | 0.54 | 10.4 | 7.45 |
| Rat 3 | 63 | 87 | 18 | 0.54 | 8.8 | 8.21 |
| Average | 63 ± 7 | 81 ± 7 | 17 ± 1 | 0.50 ± 0.06 | 9.4 ± 0.90 | 7.57 ± 0.59 |
| Normal | 57 ± 32 | 112 ± 65 | 13 ± 4 | 0.47 ± 0.10 | 10.2 ± 3.7 | 7.37 ± 1.09 |

ALT: alanine aminotransferase,
AST: aspartate aminotransferase,
BUN: blood urea nitrogen,
Creat: creatinine,
WBC: white blood cell count,
RBC: red blood cell count.
Normal values (mean ± standard deviation) are published by the vendor (Charles River).

FIG. 24 shows other exemplary dual enzyme cleavable peptides according to certain embodiments of the present invention.

FIG. 25 shows other exemplary dual enzyme cleavable peptides conjugated to Naltrexone as an exemplary medication according to certain embodiments of the present invention. Naltrexone is used a model compound for opioids and X=S or O; R=H, Acetamide, Protecting Group, Amino Acid, and Peptide.

From the foregoing description, various modifications and changes in the compositions and methods of this invention will occur to those skilled in the art. All such modifications coming within the scope of the appended claims are intended to be included therein. Throughout the disclosure, naltrexone is used as a model system. Because of its structural similarity to many opioids of interest including oxycodone, Applicants envision that the present invention is applicable to all opioids.

All publications, including but not limited to patents and patent applications, cited in this specification are herein incorporated by reference as if each individual publication were specifically and individually indicated to be incorporated by reference herein as though fully set forth.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modification forms thereof as come within the scope of the following claims.

REFERENCES CITED (1) Administration, U. S. F. a. D. FDA's Efforts to Address the Misuse and Abuse of Opioids. [Online Early Access]. Published Online: 2013. http://www.fda.gov/Drugs/DrugSafety/InformationbyDrugClass/ucm337852.htm.
(2) Policy, O. o. N. D. C.
(3) Williams, I. G. a. R. *Biotechnology and Food Ingredients*; AVI: New York, N. Y., 1943.
(4) Frye, C. L.; Dow Corning Corp.
(5) Kilgour, J. A.; Van Valkenburg Powell, V.; Powell, V. V. V.; Van Valkenburg, V.; Girger, J. A.; Bayer, V. V. V.; Van Valkenburg, P. V.; General Electric Co; Momentive Performance Materials Inc.
(6) Park, J. H.; Bae, Y. H. *Journal of Biomedical Materials Research Part A* 2003, 64A, 309-319.
(7) Alexander, L.; Mannion, R. O.; Weingarten, B.; Fanelli, R. J.; Stiles, G. L. *Drug and Alcohol Dependence* 2014, 138, 1-6.
(8) Stanos, S. P.; Bruckenthal, P.; Barkin, R. L. *Mayo Clinic Proceedings* 2012, 87, 683-694.
(9) McKenna, W. H.; Mannion, R. O.; O'Donnell, E. P.; Huang, H. H.; Purdue Pharma LP; Purdue Pharmaceuticals LP: 2014.
(10) McKenna, W. H.; Mannion, R. O.; O'Donnell, E. P.; Huang, H. H. *Official Gazette of the United States Patent and Trademark Office Patents* 2014.
(11) *The Medical letter on drugs and therapeutics* 2015, 57, 71-72.
(12) Oshlack, B.; Huang, H.-P.; Masselink, J.; Tonelli, A. P.; Purdue Pharma LP: 2015.
(13) *The Medical letter on drugs and therapeutics* 2009, 51, 61-62.
(14) Cicero, T. J.; Ellis, M. S. *JAMA psychiatry* 2015, 72, 424-430.

(15) Orman, J. S.; Keating, G. M. *Drugs* 2009, 69, 577-607.
(16) van Dorp, E. L. A.; Yassen, A.; Dahan, A. *Expert Opinion on Drug Safety* 2007, 6, 125-132.
(17) Kunoe, N.; Lobmaier, P.; Vederhus, J. K.; Hjerkinn, B.; Hegstad, S.; Gossop, M.; Kristensen, O.; Waal, H. *Drug and Alcohol Dependence* 2010, 111, 166-169.
(18) Burns, L. H.; Leri, F.; Olmstead, M. C. In *Opiate Receptors and Antagonists: From Bench to Clinic*; Dean, R. L., Bilsky, E. J., Negus, S. S., Eds. 2009, p 247-261.
(19) Webster, L. R. *Expert Opinion on Investigational Drugs* 2007, 16, 1277-1283.
(20) Caruso, F. S.; Kao, H.-H.; Purdue Pharma LP: 2015.
(21) Dowling, J.; Isbister, G. K.; Kirkpatrick, C. M. J.; Naidoo, D.; Graudins, A. *Therapeutic Drug Monitoring* 2008, 30, 490-496.
(22) *The Medical letter on drugs and therapeutics* 2011, 53, 62-63.
(23) Finch, J. W.; Kamien, J. B.; Amass, L. *Journal of Addiction Medicine* 2007, 1, 104-110.
(24) Hale, M. E.; Ahdieh, H.; Ma, T.; Rauck, R.; Oxymorphone, E. R. S. G. *Journal of Pain* 2007, 8, 175-184.
(25) Munshi, O. *Journal of Pain* 2013,14, S11-S11.
(26) Rariy, R. V.; Fleming, A. B.; Hirsh, J. C.; Saim, S.; Varanasi, R. K.; Collegium Pharmaceutical Inc: 2014.
(27) Jenkins, T. E.; Husfeld, C. O.; Jenkins T E; Husfeld C O; Signature Therapeutics Inc.
(28) Raffa, R. B.; Pergolizzi, J. V., Jr. *Drugs* 2010, 70, 1657-1675.
(29) Wang, Y.; Huang, Z.; Zhang, L.; Mei, Q. *Journal of Wuhan University of Technology-Materials Science Edition* 2006, 21, 92-94.
(30) Jovanovic, J. D.; Govedarica, M. N.; Dvornic, P. R.; Popovic, I. G. *Polymer Degradation and Stability* 1998, 61, 87-93.
(31) Besancon, B. M.; Soles, C. L.; Green, P. F. *Physical Review Letters* 2006, 97.
(32) Pharmaceuticals, S. Bio-MD™ Opioids: Abuse-Resistant Opioids. [Online Early Access]. http://www.signaturerx.com/view.cfm/59/Abuse-Resistant-Opioids.

We claim:

1. A complex for preventing unintended use of a drug, the complex comprising:
an enzyme responsive peptide;
a polymer, the polymer forming a polymer backbone of the complex;
cross-linkers, the cross-linkers connecting the polymer backbone through covalently bonding to form at least one inner cavity within the complex; and
the drug, the drug being trapped either covalently or non-covalently in the at least one inner cavity within the complex,
wherein the drug is protected from releasing outside of the complex and
wherein the enzyme responsive peptide comprises an amino acid having an α-amino group, an α-carboxylic acid group and an ε-amine group covalently bonded with an enzyme substrate comprising phenylalanine, tyrosine, or tryptophan, wherein the α-amino group is covalently bonded with a second amino acid or a peptide, and the α-carboxylic acid is covalently bonded with a first group.

2. The complex of claim 1, wherein the polymer forms an elastomer.

3. The complex of claim 1, wherein the polymer is a polysiloxane.

4. The complex of claim 1, wherein the drug is non-covalently encapsulated in the at least one inner cavity within the complex by a cross-linked elastomeric network.

5. The complex of claim 1, wherein the cross-linkers further comprise a polymer dithiol or a polymer multithiol.

6. The complex of claim 5, wherein the polymer dithiol is a polyethylene glycol (PEG) dithiol or the polymer multithiol is a PEG multithiol.

7. The complex of claim 1, wherein the second amino acid or the peptide comprises a free thiol group.

8. The complex of claim 1, wherein the first group comprises a free thiol group.

9. The complex of claim 1, wherein the first group comprises the drug.

10. The complex of claim 1, wherein the first group comprises the drug attached to the complex through a self-immolative linker.

11. The complex of claim 1, wherein the enzyme responsive peptide requires digestion by at least one enzyme to cleave the bond between the α-carboxylic acid and the first group or the bond between the α-amino group and the second amino acid or the peptide.

12. The complex of claim 1, wherein the enzyme responsive peptide requires digestion by two separate enzymes to cleave the bond between the α-carboxylic acid and the first group.

13. The complex of claim 1, wherein the enzyme responsive peptide is cleavable under the digestion of two enzymes selected from the group consisting of trypsin, chymotrypsin, gastric lipase, pepsin, aminopeptidase, carboxypeptidase, deoxyribonuclease, dipeptidase, elastase, enterokinase, lactase, maltase, pancreatic amylase, pancreatic lipase, sucrase, dextrinase, nucleosidases, phosphatases, and any other enzyme found in the stomach or intestine.

14. The complex of claim 1, wherein amino acid has the hydrophobic group and the hydrophobic group is an aromatic group.

15. The complex of claim 1, wherein the amino acid is phenylalanine.

16. The complex of claim 1, wherein the enzyme responsive peptide is cleavable under the digestion of an enzyme selected from the group consisting of trypsin, chymotrypsin, gastric lipase, pepsin, aminopeptidase, carboxypeptidase, chymotrypsin, trypsin, deoxyribonuclease, dipeptidase, elastase, enterokinase, lactase, maltase, pancreatic amylase, pancreatic lipase, sucrase, dextrinase, nucleosidases, phosphatases, and any other enzyme found in the stomach or intestine.

17. The complex of claim 1, wherein the enzyme responsive peptide comprises

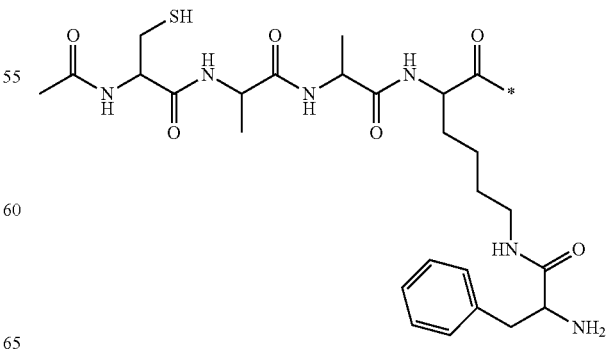

and the first group is attached at point *.

18. A polymeric formulation for controlled releasing of an active ingredient, the formulation comprising the complex of claim 1.

* * * * *